United States Patent
Wright et al.

(10) Patent No.: US 6,610,539 B1
(45) Date of Patent: Aug. 26, 2003

(54) ANTISENSE OLIGONUCLEOTIDE SEQUENCES AS INHIBITORS OF MICROORGANISMS

(75) Inventors: Jim A. Wright, Toronto (CA); Aiping H. Young, Toronto (CA); Dominique Dugourd, Toronto (CA)

(73) Assignee: GeneSense Technologies, Inc., Toronto (CA)

(*) Notice: Subject to any disclaimer, the term of this patent is extended or adjusted under 35 U.S.C. 154(b) by 0 days.

(21) Appl. No.: 09/112,580

(22) Filed: Jul. 9, 1998

Related U.S. Application Data

(60) Provisional application No. 60/052,160, filed on Jul. 10, 1997.

(51) Int. Cl.[7] .................. C07H 21/04; C12N 15/00; A61K 48/00
(52) U.S. Cl. .................. 435/375; 435/6; 435/325; 435/243; 435/252.3; 435/252.33; 435/252.35; 536/23.1; 536/24.5; 514/44
(58) Field of Search .................. 435/6, 69.1, 91.1, 435/91.31, 440, 471, 183, 325, 375, 243, 252.3, 252.33, 252.35; 536/23.1, 24.3, 24.32, 24.33, 24.5; 514/44

(56) References Cited

U.S. PATENT DOCUMENTS 5,248,670 A * 9/1993 Draper et al. .................. 514/44
5,834,279 A * 11/1998 Rubin et al. .................. 435/189
5,891,678 A * 4/1999 O'Dwyer et al. .......... 435/69.3

FOREIGN PATENT DOCUMENTS

EP 0894857 A * 2/1999

OTHER PUBLICATIONS

Branch, A.D. TIBS, vol. 23, Feb. 1998, pp. 45–50.*
Stein, C.A. Nature Biotechnology, vol. 17, Aug. 1999, pp. 751–752.*
Flanagan, W.M. et al. Nature Biotechnology, vol. 17, Jan. 1999, 48–52.*
Crooke, S.T. Chapter 1, in ANTISENSE RESEARCH, AND APPLICATION (ed. Stanley Crooke), Springer–Verlag, New York, 1998, pp. 1–50.*
Barker, R.H., Jr. et al. Proc. Natl. Acad. Sci. USA, vol. 93, pp. 514–518, Jan. 1996.*

* cited by examiner

*Primary Examiner*—Sean McGarry
(74) *Attorney, Agent, or Firm*—Greenberg Traurig, LLP; Michel Morency; John M. Garvey

(57) ABSTRACT

This invention relates to antisense oligonucleotides which modulate the expression of the ribonucleotide reductase or the secA genes in microorganisms. This invention is also related to methods of using such oligonucleotides in inhibiting the growth of microorganisms. These antisense oligonucleotides are particularly useful in treating pathological conditions in mammals which are mediated by the growth of microorganisms.

21 Claims, 49 Drawing Sheets

```
   1 atgaatcaga atctgctggt gacaaagcgc gacggtagca gacggcgcat cagagcgcac caatctcgac
  61 aaatccatc gcgttctgga ttgggcggca gaaggactgc ataacgtttc gattcccag
 121 gtcgagctgc gctcccacat tcagtttat gacggtatca gacctctga catccacgaa
 181 accattatca aggctgccgc agacctgatc tcccgtgatg cgccggatta tcagtatctc
 241 gccgcgcgcc tggcgatctt ccacctgcgt aaaaagcct acggccagtt tgagccgcct
 301 gcgctgtacg accacgtggt gaaaatggtc gagatgggca aatacgataa tcatctgctg
 361 gaagactaca cggaagaaga gttcaagcag atggacacct ttatcgatca cgacgtgat
 421 atgaccttct cttatgctgc cgttaagcag ctggaaggca atatctggt acagaaccgc
 481 gtgaccggcg aaatctatga gagcgcccaa ttccttata agcgttgc cgcgtgcttg
 541 ttctcgaact accgcgtga aacgcgcctg caatatgtga agcgttttta cgacgcggtt
 601 tccacattta aatttcgct gccgacgcca atcatgtccg gcgtgcgtac cccgactcgt
 661 cagttcaget cctgcgtact gatcgagtgc ggtgacagcc tggattccat caacgccacc
 721 tccagcgcga ttgttaaata cgtttcccag cgtgccggga tcggcatcaa cgccgggcgt
 781 attcgtgcgc tgggtagccc gattcgcggt ggtgaagcgt tccataccgg ctgcattccg
 841 ttctacaaac atttccagac agcggtgtgg tcctgctctc agggcggtgt gcgcggcggt
 901 gcggcaacgc tgttctaccc gatgtggcat ctggaagtgg aaagcctgct ggtgttgaaa
 961 aacaaccgtg gtgtggaagg caaccgcgtg cgtcatatgg actacgggt acaaatcaac
1021 aaactgatgt ataccgtct gctgaaaggt gaagatatca ccctgttcag cccgtccgac
1081 gtaccggggc ataccgacgc gttcttcgcc gatcaggaag agtttgaacg tctgtatacc
1141 aatatgaga aagacgacag catccgcaag cagcgtgtga aagccgttga gctgttctcg
1201 ctgatgatgc aggaacgtgc gtctaccggt cgtatctata ttcagaacgt tgaccactgc
1261 aataccata gcccgtttga tccggccatc gtcagtctaa gtcagtgcaa cctgtgcctg
1321 gagatagccc tgccgaccaa accgctgaac gacgtcaacg acgagaacgg tgaaatcgcg

FIG. 1A
```

```
1381 ctgtgtacgc tgtctgcttt caacctgggc gcaattaata acctggatga actggaagag
1441 ctggcaattc tggcggttcg tgcacttgac gcgctgctgg attatcagga ttacccgatc
1501 ccggccgcca aacgtggagc gatgggtcgt cgtacgctgg gtattggtgt gatcaacttc
1561 gcttactacc tggcgaacga cggtaaacgc tactccgacg gcagcgccaa caacctgacg
1621 cataaaacct tcgaagccat tcagtattac ctgctgaaag cctctaatga gctggcgaaa
1681 gagcaaggcg cgtgcccgtg gtttaacgaa accacttacg cgaaagggat cctgccgatc
1741 gatacctata agaagatct ggataccatc gctaatgagc cgctgcatta cgactgggaa
1801 gctctgcgtg agtcaatcaa aacgcacggt ctgcgtaact ccacgcttc tgctctgatg
1861 ccgtccgaga cttcttcgca gatctctaac gccactaacg gtattgaacc gccgcgcggt
1921 tacgtcagca tcaaagcgtc gaaagacggt gctgctgtgg aaatgccgg aggtggtgcc ggactacgag
1981 cacctgcacg acgcctatga gctgctgtgg atttatcgat gtaacgatgg gtaacgatgg ttatctgcaa
2041 ctggtgggta tcatgcagaa aaaagtgccg cagtcgatct ctgccaacac caactacgat
2101 ccgtcacgct tcccgtcagg acactgccg atgcagcagt tgctgaaaga cctgctcacc
2161 gcctacaaat tcggggtcaa aacactgtat tatcagaaca cccgtgacgg cgctgaaaga cgctgaagac
2221 gcacagacg atctggtgcc gtcaatccag gacgatggct gcgaaagcgg gcgaaagcgg cgcatgtaag
2281 atctga
```

*FIG. 1B*

```
7381  ctggtgccgt caatccagga cgatggctgc gaaagcggcg catgtaagat ctgatattga
7441  gatgccggat gcggcgtaaa cgccttatcc ggcctacggc tcggtttgta ggcctgataa
7501  gacgcgccag cgtcgcatca ggctccgggt gccggatgca gcgtgaacgc cttatccggc
7561  ctacggctcg gatttgtagg cctgataaga cgcgccagcg tgcatcagg cacaggatgc
7621  ggcgtaaaat gccttatccg gcattaaact cccaacagga cacactcatg gcatatacca
7681  ccttttcaca gacgaaaaat gatcagctca aagaaccgat gttctttggt cagccggtca
7741  acgtgctcg ctacgatcag caaaaatatg acatcttcga aaagctgatc gaaaagcagc
7801  tctcttct ctggcgtccg gaagaagttg acgtctcccg cgaccgtata gattaccagg
7861  cgctgccgga gcacgaaaaa cacatctta tcagcaacct gaaatatcag acgctgctgg
7921  attccattca gggtcgtagc ccgaacgtgg cgctattgcc gcttatttct attccggaac
7981  tggaaacctg ggtcgaaacc tgggcgttct cagaaacgat tcattcccgt tcctatactc
8041  atatcattcg taatatcgtt aacgatccgt ctgttgtgtt tgacgatatc gtcaccaacg
8101  agcagatcca gaaacgtgcg gaaggatct ccagctatta cgatgagctg atcgaaatga
8161  ccagctactg gcatctgctg ggcgaaggta cccacaccgt taacggtaaa actgtgaccg
8221  ttagcctgcg cgagctgaag aaaaactgt atctctgcct gatgagcgtt aacgcgctgg
8281  aagcgattcg tttctacgtc agctttgctt gttccttcgc atttgcagaa cgcgaattga
8341  tggaaggcaa cgccaaaatt attcgcctga ttgcccgcga cgaagcctg cacctgaccg
```

FIG. 2A

```
8401 gcacccagca tatgctgaat ctgctgcgca gcggcgcgga cgatcctgag atgcggaaa
8461 ttgccgaaga gtgtaagcag gagtgctatg acctgttgt tcaggcagct caacaggaga
8521 aagactgggc ggattatctg ttccgcgacg gttcgatgat tggtctgaat aaagacattc
8581 tctgccagta cgttgaatac atcaccaata tccgtatgca ggcagtcggt ttggatctgc
8641 cgttccagac gcgctccaac ccgatcccgt ggatcaaacac ttggctggtg tctgataacg
8701 tgcaggttgc tccgcaggaa gtggaagtca gttcttatct ggtcgggcag attgactcgg
8761 aagtggacac cgacgatttg agtaacttcc agctctgatg gcccgcgtta ccctgcgcat
8821 cactgccaca caactgctgt gccaggatga acaccttcc cttctggcgg cgctggaatc
8881 ccacaatgtg gcggttgagt accagtgtcg cgaaggttac tgcggctcct gtcgcacacg
```

FIG. 2B

```
 301  gtgaacgtcg atctggtgcc ggatgcagcg gatacgctcc gggcgcaagg atttcgtcaa
 361  ttaccggtgg tgatggcggg cgatttgagc tggtctggct tccgcccgga catgattaac
 421  cgtctgcacc cgacacccca cgcggcaaac gcatgagcgc gctcgtctac ttctccagca
 481  gctctgaaaa tacgcaacgc tttatgcagc gtctggggct gcctgccacg cgtattccgc
 541  tcaatgagcg ggagcgaatt caggtagacg aaccgtacat tctggttgtg ccgtcatacg
 601  gcggcggcgg gatggccggt gcggtgccgc gacaggtgat ccgcttttta aatgatgaac
 661  acaaccgggc gcgcattcgc ggcgttatcg cctccggtaa tgcaatttc ggcgatgcct
 721  ggggatgcgc tggcgatgtg atagcacaaa aatgcggcgt cccctggctg taccgctttg
 781  agctcatggg cacacaaacg gacatcgata atgtccgaaa aggagtaaat gaattttggc
 841  aacaactacc ccggagcgcg taatgcagga aaccatggat taccacgccc tgaacgcgat
 901  gctgaatctt tacgataaag caggccatat tcagttcgac aaggaccagc aggcgatcga
 961  cgccttcttt gccacccacg tccgcccgca ttccgtgacg tttgccagcc agcatgaacg
1021  tctggggacg ctggttcggg aagggtatta cgatgacgcc gtcctcgcgc gttacgaccg
1081  cgccttcgtc cttcgcctgt tcgagcacgc ccatgccagc ggctttcgct tccagacgtt
1141  tcttggcgcc tggaagttct ataccagtta cacgctgaaa accttcgacg gcaaacgtta
1201  tctggaacac tttgaagatc gggtgacaat ggtgacaat ggtggcgttg acgctggcgc agggtgacga
1261  aacgctggcc acccaactga ccgatgaaat gctttctggt cgctttcagc ccgctaccc
1321  gactttttta aattgcggca aacagcagcg tggggaactg gtctcctgct tcctgctccg
1381  tatcgaagac aacatggagt cgatcgggcg ggcggtgaat tcggcgctgc aactctccaa
1441  acgcgggcgc ggcgtcgcgt tttactctc caatctgcgc gaggcgggcg cgccgatcaa
1501  acgcattgag aatcagtctt ccggcgtgat ccggtgatg aaaatgctgg agacgcgtt
1561  ttcgtatgcc aaccaacttg gcgcgcgcca ggggccggc gcggtttatc tccatgcgca
1621  ccatccggat attctgcgtt ttctggatac caaacgagaa aacgctgacg aaaaaatccg
```

FIG. 3A

```
1681  gatcaaaacg ctctctctcg gcgtggtgat ccggatatc accttccggc tggcgaaaga
1741  aaacgcgcaa atggcgctct tttcgccta tgacatacaa cgacgctacg gcaaaccgtt
1801  tggcgatatc gccattagcg aacggtacga tgaattaatt gccgatccgc acgtgcgcaa
1861  aacctatatt aacgcccgtg acttttttca aacactggcg gagattcagt tcgaatccgg
1921  gtatccctac atcatgtttg aagatacggt aaaccgcgcg aatcccattg ctggtcgcat
1981  taatatgagc aacctgtgct cagaaatttt acaggtcaat agcgcttccc gttacgacga
2041  taaccttgac tataccacca tcgggcatga acaggtcaat atctcggct cgctgaatat
2101  cgctcacgtc atggattcac cggacattgg ccgtaccgta gaaaccgcta ttcgcggcct
2161  gacggcggtg tcggacatga gccatatacg cagcgtgccc tcaatagccg ccggtaatgc
2221  cgcctctcat gccatcggtc gccatgcat gaatctgcat ggctatctgg cgagggaagg
2281  tattgcctac ggttcgccgg aggcgttgga tttcaccaat ctctattttt acaccattac
2341  ctggcatgcc gtgcatactt caatgcggct agcccgcgaa cgcggcaaaa ccttcgccgg
2401  atttgcgcag tcgcgctatg ccagcggcgca ctattttacg cagtatttac aggacgactg
2461  gcaaccgaaa acagcgaaag tggctaaagc tcgcgacga agcggcatta cgctgccac
2521  acgagaaatg tggccgccga ccggttcgat tgtgatgcgc tatggcatct ataaccaaaa
2581  tttgcaggcg gtgccgcaaa ttgagattcg caaagaggc aaaaccgggc cctgtgtatta
2641  tcatccgatt gtttatgacca atgaaaacct ggacatgtat caggatgctt acgatatcgg
2701  ccccgcgccg tttatgacca atgaaaacct ggacatgtat caggatgctt acgatatcgg
2761  tccggaaaaa attattgata cctatgccga ggccacgcgc cacgtcgatc aagggctgtc
2821  gctcacctg ttttttcccg ataccgccac gaccccgcct atcaacaagg cgcagatcta
2881  tgcctggcga aaagtatta gtccctgta ttacatccgg cttcgccagt tggcgctgga
2941  aggtactgaa attgaaggct gcgtatcctg cgcgctataa ggaaagccat atgaaattat
3001  ctcgtattag cgccatcaac tggaacaaga tccaggacga caaagatctg gaggtatgga
```

FIG. 3B

```
3061 accggctgac cagtaacttc tggctgccgg aaaaagtgcc gttatcgaat gatattccgg
3121 cctggcagac gctgagcgcc gccgaaacagc agctcaccat tcgcgtgttt acggactta
3181 cgctgctcga cactatccag aacatcgcag gcgcgccgtc gttaatggca gatgccatca
3241 cgccgcatga agaggcagtg ctgtcgaaca tcagctttat ggaagcggta cacgcccgct
3301 cttacagttc tattttctcc acgctgtgcc agacgaaaga ggttgatgcc gcctacgcct
3361 ggagcgaaga aaacccaccg cttcagcgta aggcgacagat tatttagct cattacgtca
3421 gcgatgaacc gctaaagaaa aagattgcca gcgtcttttt agagtcttt ctgttctatt
3481 ccggcttctg gttgccgatg tatttctcca gccgcggtaa gctcacgaac actgccgacc
3541 tgattcgttt aatcattcgc gatgaagcgg ttcacggtta ttatattggc tataagtatc
3601 agatagcgct acaaaaacta tcggcaatcg agcgtgaaga gttaagctt ttcgcgctgg
3661 atttgttgat ggaactgtac gacaacgaaa tccgctacac agaagcgtta tatgcggaaa
3721 ccggctgggt taacgacgtc gacaaacttct tgtgctacaa cgtgaatccc gccttaatga
3781 acctggtta tgaggcgtta tttccgccgg agatggcaga cgtgaatcca cgcaatcttg
3841 ccgcgctctc gccgaatgcc gacgaaaacc atgatttctt ttccggctca ggttcatctt
3901 atgtgatggg gaaaacagtc gaaaccgaag acgaagactg gaattttaa ccttacgggc
3961 atgggaaata acgttacatt tcccatcaata ttattcaag caatagggag tcaaatcgcg
4021 caaatattac aacatgtcct acactctctc cgagtgacat tattcacctg gattccccca
4081 attcaggtgg atttttgctg gttgttccaa aaaatatctc ttcctcccca ttcgcgttca
4141 gccttatat catgggaaat cacagccgat agcacctcgc aatatcatg ccagaagcaa
4201 attcagggtt gtctcagatt ctgagtatgt agcttgtagaa aaaggtaact atttctatca
4261 gttaacatat cgacataagt aaataacagg aatcattcta ttgcatggca attaaattag
4321 aagtgaagaa tctgtataaa atatttggag agcatccgca gcgtgccttc aaatatattg
4381 aaaagggact atcgaaagag caaatactgg aaaaaacggg gctatcgctt ggcgttaaag
```

FIG. 3C

```
4441 acgccagtct ggccattgaa gaaggcgaga tatttgtcat catggatta tccggctcgg
4501 gtaaatccac aatggtacgc cttctcaatc gcctgattga acccacccgc ggacaggtac
4561 tgattgacgg cgttgatatt gccaaaatat cagacgctga gcttcgcgag gtgcgcagga
4621 aaaagattgc gatggtcttc cagtcatttg cgctcatgcc gcatatgacc gtgctggata
4681 atacggcatt cggtatggaa ttagcggggca tcgcgggcgca agagcgtcgc gaaaaagcgc
4741 tggacgcctt gcgtcaggtg gggcttgaga attacgctca cgcctacccg gatgaacttt
4801 ccggtgggat gcgtcagcgt gttggcttg cccgcgcgct ggcaatcaac cctgatatct
4861 tattaatgga tgaagcgttt tccgcccctcg atcc
```

FIG. 3D

```
   1 gaattcttat tttccctagc tttggattta ttctcacttc ctatgatctt ttattctcga
  61 ttattatttt tgctttggca attattatca ttttttcgac ttttttcgaca ctcaaaagaa
 121 tcaaaaatca ttgtgaatcc cttgtccccct ttggtttaaa cttatcgaga caaaagaaa
 181 aatagcacaa tatatttgt tgttttttctt ttttttacata atttaacact atatctagta
 241 tctttaattt gactagatat tttttttacg ctaaataaga ctataaaaac tcgagaaaaa
 301 gtcaaggact ttttactccc gtctaaaaaa tatattggcc caaaaggaga tttaaaatgg
 361 ttacagttta ttctaaaaaa aattgtatgc aatgcaaaat ggtcaaaaaa tggctttctg
 421 aaacacgaaat tgcatttaac gaaatcaata ttgatgaaca gcctgaattt gtcgaaaaag
 481 taattgaaat gggttttcga gctgctcctg taatcacaaa agatgatttc gcctttttctg
 541 gtttccgtcc ttctgaatta gcaaagttgg cttaatatga aacttgctta tttcagtgtg
 601 actggacaaa cgcgtcgttt tgtttctaaa acagactgc cgaatgtcga aattacacct
 661 gacgatgatt tagagatgga cgagcctttc ctccctctta tgctgaagaa tgctgaagaa
 721 tcaccaaccg tttctaaatc aatagacgtt atggactcgg ttttttgact tatgcttat
 781 aatgataatt ataaacattg tcgtggaatt atcggcactg gaaatcgtaa ttttgctggc
 841 atctatattt ttaccgctaa agaagtttca gcaaaatatc aaattccact tttatatgat
 901 tttggagttta atggtacgcc agctgatgtt gctgctgttg aaaactcgc tgcacagctt
 961 gatcaaggag cgaaagtcac cttaaaaaat ccgctgtgat ttttatggc ttcaccctat
1021 ttgagtgaag ctt
```

FIG. 4

```
   1 cagctgtact ggcataacga catttatact gtcgtataaa attcgactgg
  51 caaatctggc actctctccg gccaggtgaa ccagtcgttt ttttttgaat
 101 tttataagag ctataaaaaa cggtgcgaac gctgtttttct taagcacttt
 151 tccgcacaac ttatcttcat tcgtgctgtg gactgcaggc tttaatgata
 201 agatttgtgc gctaaatacg tttgaatatg atcgggatgg caataacgtg
 251 agtggatac tgacgcgctg gcgacagttt ggtaaacgct acttctggcc
 301 gcatctctta ttagggatgg ttgcggcgag tttaggtttg cctgcgctca
 351 gcaaacgcgc cgaaccaaac gcgcccgcaa aagcgacaac ccgcaaccac
 401 gagccttcag ccaaagttaa ctttggtcaa ttggcctttgc tggaagcgaa
 451 cacacgccgc ccgaattcga actattccgt catcttttctt catcaacatg
 501 ccattcgcac ggtaatccgt tttgcctctt tcgcaatggc accgcaaaca
 551 ctgcccgttg ctgaagaatc ctcagcgcgc caggcgcaac atcttgcatt
 601 actggatacg ctcagcgcgc tgctgaccca ggaaggcacg ccgtctgaaa
 651 agggttatcg cattgattat gcgcatttta ccccacaagc aaaattcagc
 701 acgcccgtct ggataagcca ggcgcaaggc atccgtgctg gccctcaacg
 751 cctcaactaa caacaataaa cctttacttc atttattaa ctccgcaacg
 801 cggggcgttt gagattttat tatgctaatc aaattgttaa ctaaagtttt
 851 cgtagtcgt aacgatcgca ccctgcgccg gatgcgcaaa gtggtcaaca
 901 tcatcaatgc catggaaccg gagatggaaa aactctccga cgaagaactg
 951 aaagggaaaa ccgcagagtt tcgtgcacgt ctggaaaaag gcgaagtgct
1001 ggaaatctg atccggaag ctttcgccgt gtacgtgaag gcaagtaagc
1051 gcgtctttgg tatgctcac ttcgacgttc agttactcgg cgtatgatt
1101 cttaacgaac gctgcatcgc cgaaatgcgt accggtgaag gaaaacct
```

*FIG. 5A*

```
1151  gaccgcaacc ctccctcctt acctgaacgc actaaccggt aaaggcgtgc
1201  acgtagttac cgtcaacgac tacctgacgc aacgtgacgc cgaaaacaac
1251  cgtccgctgt ttgaattcct tggcctgact gtcggtatca acctgccgg
1301  catgccagca ccggcaaagc gcgaaagctta cgcagctgac atcacttacg
1351  gtaccaacaa cgaatacagc tttgactacc tgccgacaa catggcgttc
1401  agccctgaag aacgtgtaca acgtaaacta cactatgcgc tggtggacga
1451  agtggactcc atcctgatcg atgaagcgcg tacaccgctg atcatttccg
1501  gcccggcaga agacagctcg gaaatgtata aacgcgtgaa taaaattatt
1551  ccgcacctga tccgtcagga aaagaaagac tccgaaacct tccagggcga
1601  aggccacttc tcggtggacg aaaaatctcg ccaggtgaac ctgaccgaac
1651  gtggtctggt gctgattgaa gaactgctgg tgaaagagg catcatggat
1701  gaagggaagt ctctgtactc tccggccaac atcatgctga tgccaccgt
1751  aacgacggcg ctgcgcgctc atgcgctgtt tacccgtgac gtcgactaca
1801  tcgttaaaga tggtgaagtt atcatcgttg acgaacacac cggtcgtacc
1851  atgcagggcc gtcgctgatc cgatgatctg caccagcta tggaagcaa
1901  agaaggtgtg cagatccaga acgaaaacca aacgctgact tcgatcacct
1951  tccagaacta cttccgtctg tatgaaaaac atttagctca atctacaagc tggatgaccgt
2001  gctgataccg aagctttcga accaaccgtc caatgattcg caatgatctg ccgacctgg
2051  cgttgttccg accaaccgtc caatgattcg taaagatctg ccgacctgg
2101  tctacatgac tgaaagcgaa aaaattcagg cgatcattga agatatcaa
2151  gaacgtactg cgaaaggcca gccggtgctg gtgggtacta tctccatcga
2201  aaaatcgaag ctgaqtcaa acgaactgac caaagccggt attaagcaca
2251  acgtcctgaa cgccaaattc cacgccaacg aaagcggcga t tgttgctcag
```

FIG. 5B

```
2301 gcaggttatc cggctgcggt gactatcgcg accaatatgg cggtcgtgg
2351 tacagatatt atgctcgata gtagctggca ggcagaagtt gccggctgg
2401 aaaatccgac cgcagagcaa attgaaaaaa ttaaagccga ctagcagta
2451 cgtcacgatg cggtactgga agcaggtggc ctgcatatca tcggtaccga
2501 gcgtcacgaa tcccgtcgta tcgataacca gttgcgcggt cgttctggtc
2551 gtcaggggga tgctggttct tcccgtttct acctgtcgat ggaagatgcg
2601 ctgatgcgta tttttgcttc cgaccggata tccggcatga tgcgtaaact
2651 gggtatgaag ccaggcgaag ccattgaaca cccgtggtg actaaagcga
2701 ttgccaacgc ccagcgtaaa gttgaaagcc gtaacttcga cattcgtaag
2751 caactgctgg aatatgatga cgtgctaac gatcagcgtc gcgccattta
2801 ctcccagcgt aacgactgt tggatgtcag cgatgtgagc gaaaccatta
2851 acagcattcg tgaagatgtg ttcaaaagcga ccattgatgc ctacgttcca
2901 ccacgtcgc tggaagaaat gtgggatatt ccgggactgc aggaacgtct
2951 gaagaacgat ttcgacctcg atttgccaat tgccgagtgg ctggataaag
3001 aaccagaact gcatgaagag acgctgcgta acggcattct ggcgcagtcc
3051 atcgaagtgt atcagcgtaa agagaaagtg attggtgctg agatgatgcg
3101 tcacttcgag aaaggcgtca tgctgactcc ctgtgaaaag
3151 agcacctggc agcgatggac tatctgcgtc agggtatcca cctgcgtggc
3201 tacgcacaga aagatccgaa gcaggaatac aaacgtgaat cgttctccat
3251 gtttgcagcg atgctggagt cgttgaaata tgaagttatc agtacgctga
3301 gcaaagttca ggtacgtatg cctgaagagg ttgaggagct ggaacaacag
3351 cgtcgtatgg aagccgaaca tttagccgcg atgcagcagc ttagccatca
3401 ggatgacgac tctgcagccg cagctgccct gcgcgccaa accggagagc
```

*FIG. 5C*

```
3451 gcaaagtagg acgtaacgat ccttgcccgt gcggttctgg taaaaaatac
3501 aagcagtgcc atgccgcct gcaataaaag ctaactgttg aagtaaaagg
3551 cgcaggattc tgcgcctttt ttataggttt aagacaatga aaaagctgca
3601 aattgcggta ggtattattc gcaacgagaa caatgaaatc tttataacgc
3651 gtcgcgcagc agatgcgcac atggcgaata aactggagtt tcccggcggt
3701 aaaattgaaa tgggtgaaac gccggaacag gcggtggtgc gtgaacttca
3751 ggaagaagtc gggattaccc cccaacattt ttcgctattt gaaaaactgg
3801 aatatgaatt c
```

FIG. 5D

```
   1 gatctacggc agaactcgtc gcttggagcg ttcgaccgac catctacctg
  51 ttcgacgtcg aactcgacca ctgaacgtaa tgcccgccag cgcaagtcct
 101 gtcagcgcgt ggagatcacc gcgcgtgggc gagggccggt ggtgcgaggt
 151 gaggcctgcg ccgacagctt ctatgccgcg cttgaatcag cggtcgtcaa
 201 actggagagc gtgcgccgcg gtaaggatcg ccgcaaggtg cactacggcg
 251 acaaaacccc ggtttcgctg gccgaggcga ccgcggtggt gccagcgccg
 301 gagaacggct tcaacaccag accagccgag gcacacgatc acgacggtgc
 351 cgtcgtcgag cgggagcctg ggcggatcgt tcgcaccaaa gaacacccgg
 401 ccaagccgat gtcggtcgat gacgcgctct accagatgga gctggttgga
 451 cacgacttct tcttgttcta cgacaaggac accgaacggc cgtcgtggt
 501 ctaccgccgg cacgcctacg actacggctt gatccgtctg gcgtgatcgg
 551 cggcgcgc cgctcgtcac ctaccatggg agtcgcctta tctaaagact
 601 cctacacatg cggggacata gctgtgctgt cgaagttgct gcgccttggc
 651 gaagtcgca tggtcaagcg cctcaagaag gtggcggact atgtcggcac
 701 tttgtccgac gatgtcgaga aactcaccga cgccgagctg agggcgaaaa
 751 ccgacgagtt caagcggcgg ctggccgacc cgcccgtg gccgcgagg agaaacccte
 801 gacgacctgt tgcccgagge cttcgcccgt tcgacgtgca ggtgatgggt gcggccgccc
 851 ggtgctggac cagcggccgt caacgttgcc gagatgaaga ccggtgaagg caagacccig
 901 tgcacctggg caacgtgggg tgcccgctta cctcaatgcg ctgccggca acggcgtgca
 951 acctgtgtgt tgcccgctta cctcaatgcg ctgccggca acggcgtgca
1001 catcgtcacc gtcaacgact acctggctaa acgcgacaag gagtggatgg
1051 gccgcgtgca ccgcttcctc gggcttcagg tcgggtgat tttcgccacc
1101 atgacacccg atgaacgccg gtggcctat aacgccgaca tcacctacgg
```

FIG. 6A

```
1151  caccaataac  gagtttgggt  tcgactacct  gcgcgacaac  atggcgcact
1201  cactggatga  tctggtgcag  cgggcacc    attacgccat  tgtcgacgag
1251  gtcgattcca  tcctgatcga  cgaggcccgc  acccgctga   tcatctccgg
1301  tcccgccgac  ggcctccaac  tggtacaccg  agttcgccgg  ttggcgccgc
1351  tgatggaaaa  ggacgtccac  tacgaggtcg  atctacgcaa  acgcaccgtc
1401  ggcgtgcacg  agaagggtgt  ggaattcgtc  gaagaccagc  tcggcatcga
1451  caacctgtac  gaggccgcca  actcgccgtt  ggtcagctat  ctcaacaacg
1501  ctctgaaggc  caaagagctg  ttcagccgcg  acaaggacta  catcgtccgc
1551  gatggtgagg  tgctcatcgt  cgacgagttc  acggccgggg  tgctgatcgg
1601  ccgccgctac  aacgagggca  tcgaccagcc  catcgaggcc  aaggagcacg
1651  tcgagatcaa  ggccgagaac  cagacgctgg  ccaccatcac  gctgcagaac
1701  tacttccggc  tctacgacaa  gctcgccggc  atgaccggca  ccgcccagac
1751  ggaggcggcc  gagctgcacg  agatctacaa  gctgggcgtg  gtcagcatcc
1801  cgaccaacat  gccgatgatc  cgtgaagacc  agtccgacct  gatctacaag
1851  accgaggagg  ccaagtacat  cgcggtggtc  gacgacgtcg  ccgagcgcta
1901  cgcgaaggga  cagccggtgc  tgatcggcac  cgcgagcgtg  gagcgctcgg
1951  agtatctgtc  gcggcagttc  accaagcggc  gcatcccgca  caatgtgctc
2001  aacgccaagt  accacgagca  agaggcgacc  atcatcgcgg  tggcgggccg
2051  ccgcggcggc  gtcaccgtcg  ccaccaacat  ggccggtcgc  ggcaccgaca
2101  ttgtgctggg  cggcaacgtc  gactttctca  ccgatcagcg  gctgcgcgaa
2151  cggcctggat  ccggtggaga  cgcccgagga  gtacgaggcg  gcctggcact
2201  ccgaactgcc  catcgtcaaa  gaggaagcca  gcaaggaggc  caaggaagta
2251  atcgaggccg  gcggctgtac  gtgctgggca  ccgagcggcc  acggagtcgcg
```

FIG. 6B

```
2301 gcggatcgac aaccagttgc gtggccggtc cggccgccag gggacccgg
2351 ggagtcgcgc ttctatttgt cgctgggtga cgagcgatg cgccgcttca
2401 atggcgcggc cttggagacc ttgttgacca ggctgaacct gccgacgac
2451 gtgccgatcg aagccaagat ggtcacccgg gccatcaaga gcgcccagac
2501 ccaggtcgag cagcagaact ttgggtccg caagaacgtc ctcaaatacg
2551 acgaggtgat gaaccagcag cgcaaggtca tctacgccga gcgccggcgc
2601 atcctcgaag gcgaaaacct caaggaccag gcgctggaca tggtccgcga
2651 tgtcatcacc gcctacgtcg acggcgcgac cggcgaaggc tatgccgaag
2701 attgggatct ggacgcgttg tggacggcac tcaaaaccct ctatccggag
2751 gggatcaccg ccgactcgct gacccgcaag gaccacgaat tcgagcgcga
2801 cgatctcacc cgcgaggagt tgctggaggc actactcaag gacgccgaac
2851 gtgcctatgc cgcgtggaa gccgaactcg aggaaatcgc cggcgagggt
2901 gcgatgcgcc agctggaacg caacgtgctg ctcaacgtca tagaccgtaa
2951 gtgcgtgaa cacctctacg agatggacta cctcaaggag ggtatcgggc
3001 tgcgcgcgat ggcgcacggc gatccgttgg tcgagtacca gcgtgagggc
3051 tacgacatgt tcatggccat gctcgacggc atgaaagagg aatcggtcgg
3101 cttcctgttc aacgtcaccg tggaggcggt cttgccgaat cccgcccg ccggttgcc
3151 cggctgccga acccgcagag cttgccgaat tcgccgccgc ggccgcagcc
3201 gcgggcagca acgcagcgcg gtcgatggtg gcgcgcgcga aagagctcca
3251 agtgcattac gcgccaaggg tgttgccagc gagtcgccg gagtcgccg cttgaccta
3301 ttccggtccc gcggaggatg gctcggctca ggtgcagcgc aacggcggtg
3351 gagcccacaa gacgccggc ggagtgccgg ccggtgctag ccggcgcgag
3401 cggcgcgaac gcgcccgcg acaaggccgc ggcgccaagc cgcgaaatc
```

FIG. 6C

```
3451  ggtcaagaag  cgttagcgcg  taggttgcag  atgggtgtat  cggtttctca
3501  gttcccagaa  gtcacttccc  ggcacacccc  ggccccggcg  cgcatgcaca
3551  tttcgttgca  cggcggggcaa  ggggttcgct  aatctcaccc  gttcgtcgac
3601  cttcgtcggc  gtcggttctg  ctggtagcgg  ggttcggcgc  tttcctggcg
3651  tttctcgact  cgacaatcgt  caacatcgcg  ttcccggata  tccagcgttc
3701  cttcccgtcc  tacgacatcg  ggagcctgtc  ctggattctg  aacggctata
3751  acatgctctt  cgccgccttc  atggttgcgg  ccggcaggtt  ggccgattcg
3801  ctgggccgca  gacgacattc  ctgtccggtg  tgctggtgtt  caccattgcg
3851  tccgggctgt  gcgccgtcgc  cggcagtgtc  gagcagttgg  tggcgttccg
3901  ggtgctgcag  ggcatcggggg  ctgcgatact  cgtgcctcgt  tcgctcgcac
3951  tggtcgttga  gggcttcgac  cgggccgcg  cgcgcacgct  atcggcctgt
4001  ggggtgcggc  ggcagcgatc  cactagttct  agagcgggcgc  accgc
```

FIG. 6D

```
  1  tcaaacacca  gaccagaagg  aggcaacacg  atcacggacg  gtgccgttcg
 51  tcgagcggga  gcctggggcg  gatcgttcgc  accaaagaac  aacccgcca
101  cgccgatgtc  ggtcgatgac  gcgctctacc  agatggagct  ggttggacac
151  gacttcttct  tgttctacga  caaggacacc  gaacggccgt  cggtgtcta
201  ccgccggcac  gcctacgact  acggcttgat  ccgtctggcg  tcatcggcgg
251  cgcgcgccgc  gtcgtcacct  accatgggag  tgccttatc   taaagactcc
301  tacacatgcg  gggacatagc  tgtgctgtcg  aagttgctgc  gccttggcga
351  aggtcgcatg  gtcaagcgcc  tcaagaaggt  ggccgactat  gtcggcactt
401  tgtccgacga  tgtcgagaaa  ctcaccgacg  ccgagctgag  ggcgaaaacc
451  gacgagttca  agcaggctgg  ccgaccagaa  aaacccagaa  accctgcgacg
501  acctgttgcc  cgaggccttc  accgtgccct  gcgagtgccc  cctgccgggt
551  gctggaccaa  cgaccgttcg  acgtgcaggt  gatgggtacg  accgcccctgc
601  acctgggcga  cgttgccgag  atgtagaccg  gtgaaggcaa  gacctgacc
651  tgtgttttac  ccgcttacct  caatgccctg  gccgccaacg  gcgtgcacgt
701  agttaccgtc  aacgactacc  tggctaaacg  cgacagtgag  tggatgggcc
751  gcgtgcaccg  cttcctcggg  cttcaggtcg  gggtgattt   ggccaccatg
801  acacccgatg  aacgccggt   ggcctataac  gccgacatca  cctacggcac
851  caataacgag  tttgggttcg  actacctgcg  cgacaacatg  gcgcactcac
901  tggatgatct  ggtgcagcgc  acgcactatt  acgccattgt  cgacgaaggt
951  cgattccatc  ctgatcgacg  agggcggggc  ccccccccca  tctccgcccg
```

FIG. 7A

```
1001 gggcgcccgc ctccaactgg ttcaccgagt tcgccggtt tcgccgggc ggcgtgccgc
1051 ggctggtttt ggacgtccac tacgaggtcg atctacgcaa acgcaccgtc
1101 ggcgtgcacg agaagggtgt ggaattcgtc gaagaccagc tcggcatcga
1151 caacctgtac gagaccgcca actcgccgtt actcgccgtt ctcaacaacg
1201 ctctgaaggc caaagagctg ttcagccgcg acaaggacta catcgtccgc
1251 gatggtgagg tgctcatcgt cgacgagttc accggccggg tgctgatcgg
1301 ccgccgctac aacgagggca tgcaccaggc catcgaggcc aaggagcacg
1351 tcgagatcaa ggccgagaac cagacgctgg ccaccatcac gctgcagaac
1401 tacttccggc tctaggagaa gctcgccggg atg
```

*FIG. 7B*

```
   1 tggcttgatt caaactagtg aacaataaat taagtttaaa gcacttgtgt
  51 ttttgcacaa gtttttttat actccaaaag caaattatga ctatttcata
 101 gttcgataat gtaatttgtt gaatgaaaca tagtgactat gctaatgtta
 151 atggatgtat atatttgaat gttaagttaa taatagtatg tcagtctatt
 201 gtatagtccg agtcgaaaat cgtaaaatat ttataatata atttattagg
 251 aagtataatt gcgtattgag aatatattta ttagtgataa acttgttgac
 301 aacagaatgt gaatgaagta tgtcataaat atatttatat tgattctaca
 351 aatgagtaaa taagtataat tttctaacta taaatgataa gatatatttgt
 401 tgtaggccaa acagtttttt agctaaagga gcgaacgaaa tgggattttt
 451 atcaaaaatt cttgatggca ataataaga aattaaacag ttagtaaac
 501 ttgctgataa agtaatcgct ttagaagaaa aaacggcaat tttaactgat
 551 gaagaaattc gtaataaaac gaaacaattc caaacagaat tagctgacat
 601 tgataatgtc aaaaagcaaa atgattattt acataaaatt ttaccagaag
 651 catatgcact tgttagagaa ggctctaaac gtgtattcaa tatgacacca
 701 tataaagttc aaattatggg tggtattgca attcataaag gtgatatcgc
 751 tgagatgaga acaggtgaag gtaaaacatt aacagcgaca atgccaacat
 801 acttaaatgc attagctggt agaggtgttc acgttattac agtcaatgaa
 851 tacttatcaa gtgttcaaag tgaagaaatg gctgagttat ataacttctt
 901 aggtttgact gtcggattaa acttaaacag taagacgaca gagaaaaaac
 951 gtgaagcata cgcacaagac attacttaca gtactaataa tgagctaggt
1001 tttgattact tacgagataa catggtgaat tattctgaag ataggtaat
1051 gcgtccatta catttgcaa tcattgatga ggtggactca atttaatcg
```

FIG. 8A

```
1101  acgaggcacg  tacgccatta  attattctg   gtgaagctga  aaagtcaacg
1151  tcactttata  cacaagcaaa  tgttttgcg   aaaatgttaa  aacaggacga
1201  tgattataaa  tacgatgaaa  aaacgaaagc  tgtacattta  acagaacaag
1251  gtgcggataa  agctgaacgt  atgttcaaag  atgttcattt  atatgatgta
1301  caaaatgttg  atgttattag  tcatatcaac  acagctttac  gtgcgcacgt
1351  tacattacaa  cgtgacgtag  actatatggt  tgttgatggc  gaagtattaa
1401  ttgtcgatca  atttacagga  cgtacaatgc  caggccgtcg  tttctcggaa
1451  ggttacacc   aagctattga  agcgaaggaa  ggcgttcaaa  ttcaaaatga
1501  atctaaaact  atggcgtcta  ttacattcca  aaactatttc  agaatgtaca
1551  ataaacttgc  gggtatgaca  ggtacagcta  aaactgaaga  agaagaattt
1601  agaaatattt  ataacatgac  agtaactcaa  attccgacaa  ataaacctgt
1651  gcaacgtaac  gataagtctg  atttaattta  cattagccaa  aaaggtaaat
1701  ttgatgcagt  agtagaagat  gttgttgaaa  aacacaaggc  agggcaacca
1751  gtgctattag  gtactgttgc  agttgagact  tctgaatata  tttcaaattt
1801  acttaaaaaa  cgtggtatcc  gtcatgatgt  gttaaatgcg  aaaaatcatg
1851  aacgtgaagc  tgaaattgtt  gcaggcgctg  gacaaaaagg  tgccgttact
1901  attgccacta  acatggctgg  tcggggtaca  gatatcaaat  taggtgaagg
1951  cgtagaggaa  ttaggcggtt  tagcagtaat  aggtacagag  cgacatgaat
2001  ctcgtcgtat  tgatgaccag  ttacgtggtc  gttctggacg  tcaaggtgat
2051  aaggggata   gtcgcttcta  tttatcatta  caagatgaat  taatgattcg
2101  ttttggttct  gaacgtttac  agaaaatgat  gagccgacta  ggttagatg
2151  actctacacc  aattgaatca  aaaatggtat  caagagctgt  tgaatcagca
```

FIG. 8B

```
2201 caaaaacgtg tagaaggtaa taacttcgac gcgcgtaaac gtatcttaga
2251 atacgatgaa gtattacgta aacacgtga aattatctat aacgaaagaa
2301 atagtattat tgatgaagaa gacagctctc aagttgtaga tgcaatgcta
2351 cgttcaacgt tacaacgtag tatcaattac tatattaata cagcagatga
2401 cgagcctgaa tatcaaccat tcatcgacta cattaatgac atcttcttac
2451 aagaaggtga cattacagag gatgatatca aaggtaaaga tgctgaagat
2501 attttcgaag tcgtttgggc taagattgaa gcagcatatc aaagtcaaaa
2551 agatatctta gaaaacaaa tgaatgagtt tgagcgtatg attttacttc
2601 gttctattga tagccattgg actgatcata tcgacacaaat ggatcaatta
2651 cgtcaaggta ttcacttacg ttcttatgca cattacgtga
2701 ctatcaaaat gaaggtcatg aattatttga tatcatgatg caaaatattg
2751 aagaagatac ttgtaaattc attttaaaat ctgtagtaca agttgaagat
2801 aatattgaac gtgaaaaaac aacagagttt ggtgaagcga agcacgtttc
2851 agctgaagat ggtaaagaaa aagtgaaaac gaaaccaatc gttaaaggcg
2901 atcaagttgg tcgtaacgat gattgtccat gtggtagtgg taaaaattc
2951 aaaaattgcc atggaaaata aatgatataa aataactcct tccaattaaa
3001 cacctatagt ttgtgttatg ggaggtct tttattttta caagcgttaa
3051 atactttaaa aaatgtgaag aagttgttaa acgttgttat gtacttagtt
3101 ttaaaaaatc ggtttaggca tatg
```

FIG. 8C

```
   1 cttgaacgtt acttcactaa tgtgccgaat gtgaatgcac atgtaaaagt
  51 gaaaacttat gcaaattcta gcacaaaatc gaagttacaa ttccgcttaa
 101 tgacgtgaca cttcgtgcag aagaaagaaa cgatgattta tgctggaatt
 151 gacaagatca ctaacaaatt agaatgtcaa gttcgtaaat acaaaacacg
 201 tgtcaatcgt aagaaacgta aagaaagcga acatgaacca ttcccagcaa
 251 ctccggaaac tccgccggaa acagctgttg atcatgataa agatgatgaa
 301 attgaaatca tccgttctaa acaattcagc ttgaaaccaa tggattctga
 351 agaagcggta ttacaaatgg atttacttgg tactgatttc ttcatcttca
 401 atgaccgtga aactgatggt acaagcattg tttaccgccg taaagacgga
 451 aaatatggtt tgattgaaac tgttgaaaaa ctaatatgtg atatttgaaa
 501 gggctcttgc tgcatttttt gctgcaagag tttctttttt tgagaaagcc
 551 cttattaaga tttgattaat aaaaatacaa ttgattgatt tacacgggt
 601 gtccatgtca aaataagagg gatgtattaa gttcataatt gtaatgtgag
 651 ctccgatgag tgagcggcat atgattatga tatccatgtg gcacatgatg
 701 ttaacaaaaa gagaagtgaaa ctgtgagaag tacatcttga taaacacac
 751 taggcagttt attaaaaaat aatgaacagt atcctatgag tttttaagta
 801 taaattaagc catataaatg gtaagataaa ttgttgtaag ccaaacagtt
 851 tttataccaa aggagcgaac agaatgggtt ttttaacaaa aattgttgac
 901 ggcaataaga gagaaataaa acgcctaagt aagcaagctg acaaagtaat
 951 ctcattagaa gaagaaaatgt caattcttac tgataagaa attagaaata
1001 aaacaaaagc attccaagaa agattgcaag cagaagaaca tgtaagcaa
1051 caagataaaa tttagaaga aatattacct gaagcatttg cgcttgtccg
1101 tgaaggagct aaacgtgtat ttaatatgac accttatcca gttcaaatca
1151 tgggtggtat cgccattcat aatggtgaca tttcagaaat gagaacaggt
```

FIG. 9A

```
1201 gaaggtaaaa cattaactgc aacgatgccg acttatttaa acgccttagc
1251 agcacgtggt gtgcatgtta ttacagtcaa tgaatacttg gcaagttctc
1301 aaagagaaga aatggccgag acaaattcca aagcgtgaag atcagtcgga
1351 ttgaacttga acagcttatc aacagaacaa aagcgtgaag cttataatgc
1401 agatattacg tatagtacaa ataatgaatt aggcttcgac tatttacgcg
1451 ataacatggt gaattattca gagaacgtg ttatgcgtcc gcttcattc
1501 gctatcattg atgagtcga ctctatttta atcgatgaag cgcgtacacc
1551 attgattatt tcaggggaag ctgaaaaatc aacatctctt tatacacaag
1601 caaatgtttt cgctaaaatg ttaaaagcag aagatgatta taattatgat
1651 gaaaaaacaa aatcagtaca attaacagat caaggtgctg ataaagctga
1701 acgtatgttc aagttagata acttatatga tttgaaaaac gttgatatta
1751 tcacgcatat caatacagca ttacgtgcta actatacatt gcaaacgcat
1801 gtagattaca tggttgtaga tggagaagta ttgattgtcg accaattac
1851 aggtcgaaca atgccaggtc gtcgattctc tgaaggactt caccaagcga
1901 ttgaggctaa agaaggggtt caaattcaaa atgaatctaa aacaatggct
1951 tctatcacat tccaaaacta cttccgtatg tataataaat tagccggtat
2001 gacaggtact gctaaaacag aggaagaaga attccgtaac attatataata
2051 tgacagttac acaaattcca acgaaccgtc ctgttcaacg tgaagataga
2101 cctgacttga ttttcatcag ccaaaaggc aagttcgatg ctgttgttga
2151 agatgttgtt gaaaaacata aaaaggcca accaattctt ttaggtactg
2201 tagcggttga aacaagtgaa tacatttcac aactattgaa aaaacgcggt
2251 gtgcgtcatg atgtcttaaa cgctaaaaac catgaagcg aagctgaaat
2301 cgtatctaca gcaggtcaaa aaggtgcagt cacaacgca acaaacatgg
2351 ctgtcgtgg taccgatatt aaattaggcg aaggtgttga agaattaggc
2401 ggccttgctg ttattggtac agaacgtcat gaatcacgcc gtatcgatga
```

FIG. 9B

```
2451 tcagttgcgt ggtcgttctg gacgacaagg tgaccgcgga gaaagccgtt
2501 tctatttatc attacaagat gagttgatgg tacgtttcgg ttctgaacgt
2551 ctgcaaaaaa tgatgggccg attaggtatg gatgactcta caccgattga
2601 atcaaaaatg gtatctcgag ctgttgaatc tgcacaaaaa cgtgttgaag
2651 gtaacaactt cgatgcacgt aaacgtatct tagaatacga tgaagtttta
2701 cgtaaacaac gtgaaatcat ttatggtgaa cgtaataata ttatcgattc
2751 agaatcaagt tctgaattag tcattacaat gatacgctct acattagatc
2801 gtgcaatcag ttattatgta aatgaagaat tggaagaaat tgactatgcg
2851 ccgtttatta attttgtgga agatgttttc ttdcacgaag gtgaagtcaa
2901 agaagatgaa atcaaaggta aggtaaaga tcgtgaggat attttcgata
2951 cagtatgggc taaaattgaa aaagcttatg aagcacaaaa agccaatata
3001 cccgaccaat tcaatgaatt cgaacgtatg atttattac gttctattga
3051 tggaagatgg acagaccata tcgatacaat ggatcaatta cgtcaaggta
3101 tccatttacg ttcatacggt caacaaaacc cacttcgcga ctatcaaaat
3151 gaagggcacc aactatttga tacaatgatg gtcaatattg aagagacgt
3201 cagcaaatat atcttgaaat caattatcac agtagatgat gatattgaac
3251 gtgataaagc aaaagaatat caaggacaac atgtatcagc tgaagatgga
3301 aaagaaaaag taaaaccgca accagttgtt aaagataatc acatcggaag
3351 aaatgatcct tgtccatgcg gcagcggtaa aaagtataaa aattgctgcg
3401 gtaaatagta agttgtatta ggaccactgt taaatagctt taagagagat
3451 gctcaattga aattgggtta tctttctaag ggctgtcagc ggtctttttt
3501 caatccaaca aaaatatgga tatatgctaa aataatagag taatctgaa
3551 aattaaactg gaattggaga gatatgaaaa tggaattat
```

FIG. 9C

```
   1 cagtcaatgt cgctcttcgt gaccgagcca atggacggaa aggtgccgc  ctcccagatc
  61 atgaacctcc tagtgtacgc ctataagaag ggccttaaga cgggctcta  ctactgcaag
 121 atccgcaagg ccaccaacaa cggcgtcttc acggcgcg   acctcgtgtg ctctgggtgc
 181 cacctgtagc gacgcgcgcc gagcgcggcc ccgaggcgg  cggacgcggc gaccctcacg
 241 cgtaaataca aatacttta  cgagaccgag tgccccgacc tagatcactt gcggtcgctc
 301 agcgtcgcaa accgctggct ggagaccgag tttccccctag cggacgacgc caaggacgtg
 361 gcgcggctca gcggcgccga gctggagttt taccgcttc  tgttcgcgtt cctctcggcc
 421 gccgatgacc tcgtgaacgt caacctcggg gacctgtccg agctgttcac ccaaaaagac
 481 atcctgcatt actatatcga gcaggagtcc atcgaagtgg tgcactcgcg ggtgtacagc
 541 gccatacagc tgctgctctt tagaaacgac gcggtggcgc gcgcgggcta cgtagagggc
 601 gccctcggcg acccgcgcgt ccggcgcaag ccggcccgca cgagcggcg  cgtggccgcg
 661 gcagagtcgg tggccgaaaa cggccagtgc gtacgtgctc atgattctaa tcgagggcat tttttctcc
 721 tcctcgtttg cggcgattgc ctacctgcgc acccacaacc ttttcgtcgt gacgtgccaa
 781 accaacgacc tcatcagccg cgacgaagcc gtgcacacgg ccgtcgtg  ctgcatcttc
 841 gacaactacc tcggcgggga gcgccgcgcg ccggcccgca tctacgagct gttccgcgaa
 901 gcgtggaaat tgagcgcgag tttatttggt tgcgcgccgc gggcagtca  tatacttgac
 961 gtgtgggcta tttctgcgta cgtcgagtac agcgcggacc gcctgctcgc tgctatccag
1021 ctgccctcctc tgtttggcac cccgcctcct gggaccgatt ttcctttggc cctgatgact
1081 gccgagaagc acacgaactt ctttgagcgc cgcagcacca actacacagg caccgtaatc
1141 aacgacctgt aggcaccccc cgctgccctg ccagagcgcc ccgcctttcc tcctccttct
1201 cacccccacg ccgcgaataa aaatgttcc  atgtcaacga aa
```

FIG. 10

```
   1 tcgagcccgc cgaaaccgc  cgcgtctgtt  gaaatggcca  gccgcccagc  cgcatcctct
  61 ccgtcgaag  cgcggccccc  ggttggggga  caggaggccg  gcggcccag   cgcagccacc
 121 caggggagg  ccgccgggc   ccctctcgcc  cacggccacc  acgtgtactg  ccagcggtc
 181 aatggcgtga tggtgctttc  cgacaagacg  cccgggtccg  cgtcctaccg  catcagcgat
 241 agcaacttg  tccaatgtgg  ttccaactgc  accatgatca  tcgacggaga  cgtggtgcgc
 301 gggcgccccc aggacccggg  ggccgcggca  tccccgctc   ccttcgttgc  ggtgacaaac
 361 atcggagccg gcagcgacg   cgggaccgcc  gtcgtggcat  tcggggaac   cccacgtcgc
 421 tcgcggggga cgtctaccgg  taccagacg   gccgagtcc   ccaccgagcc  ccttggggc
 481 cccctcctc  ctcccgctt   caccctgggt  ggcggctgtt  gttcctgtcg  cgacacacgg
 541 cgccgctctg cggtattcgg  ggggagggg   gatccagtcg  gccccgcgga  gttcgtctcg
 601 gacgaccggt cgtccgattc  cgactcggat  gactcggagg  acacggactc  gggagacgctg
 661 tcacacgcct cctcggacgt  gtccggcggg  gccacgtacg  agacgccct   tgactccgat
 721 tcgtcatcgg atgactccct  gcagatagat  ggcccccgtgt gtcgcccgtg  gagcaatgac
 781 accgcgcccc tggatgtttg  cccccgggacc gccccgggg   gcgcgacgc   cggtggtccc
 841 tcagcggtag acccacgc   gccgacgcca  gaggccggcg   ctggtcttgc  ggccgatccc
 901 gccgtggccc ggggagacgc  ggagggcctt  tcggacccc   cccgagaacg  gggaacgggc
 961 acggcctacc ccgtcccct   ggaactcacg  cccccccagg  cggaggccgt  ggcgcgcttt
1021 ctgggagatg ccgtgaaccg  cgaacccgcg  ctcatgctgg  agtacttttg  ccggtgcgcc
1081 cgcgaggaaa ccaagcgtgt  cccccccagg  acattcggca  gccccctcg   cctcacggag
1141 gacgacttg  ggcttctcaa  ctacgcgctc  gtggagatgc  agcgcctgtg  tctggacgtt
1201 cctccggtcc cgccgaacgc  atacatgccc  tattatctca  gggagtatgt  gacgcggctg
1261 gtcaacgggt tcaagccgct  ggtgagccgg  tccgtcgcc   tttaccgcat  cctggggtt
1321 ctggtgcacc tgcggatccg  gaccccggag  gcctccttg   aggagtggct  gcgatccaag
```

FIG. 11A

```
1381 gaagtgccc tggattttgg cctgacggaa aggcttcgcg agcacgaagc ccagctggtg
1441 atcctggccc aggctctgga ccattacgac tgtctgatcc acagcacacc gcacacgctg
1501 gtcgagcggg ggctgcaatc ggccctgaag tatgaggagt tttacctaaa gcgttttggc
1561 gggcactaca tggagtccgt cttccagatg tacacccgca tcgccggctt tttggcctgc
1621 cgggccacgc gcggcatgcg ccacatcgcc ctggggcgag agggtcgtg gtgggaatg
1681 ttcaagttct ttttccaccg cctctacgac caccagatcg taccgtcgac ccccgccatg
1741 ctgaacctgg ggacccgcaa ctactacacc tccagctgct acctggtaaa cccccaggcc
1801 accacaaaca aggcgaccct gcgggccatc accagcaaacg tcagtgccat cctcgcccgc
1861 aacgggggca tcgggctatg cgtgcaggcg tttaacgact ccggccccgg gaccgccagc
1921 gtcatgcccg ccctcaaggt ccttgactcg ctggtggcgg cgcacaacaa agagagcgcg
1981 cgtccgaccg gcgcgtgcgt gtacctggaa ccgtggcaca ccgacgcgcg ggccgtgctc
2041 cggatgaagg gggtcctcgc cggcgaagag gcccagcgct gcgacaatat cttcagcgcc
2101 ctctggatgc cagacctgtt tttcaagcgc ctgattcgcc acctggacgg cgagaagaac
2161 gtcacatgga ccctgttcga cgggacacac agcatgtcgc tgccgactt tcacggggag
2221 gagttcgaga agctctacca gcacctcgag gtcatgggt gcggccacga gataccatc
2281 caggagctgg cctatggcat tgtgcgcagt gcggccaagc ccgggagccc cttcgtcatg
2341 ttcaaagacg cggtgaaccg ccactacatc tacactacca aggacatca catccgcgg
2401 tccaacctct gcaccgagat cgtccatccg gcctccaagc gcctccaagc catcgccggc
2461 ctgggaagcg tgaatctggc ccgatgcgtc ccgatgcgtc cgtttgactt tgggcggtc
2521 cgcgacgccg tgcaggcgtg cgtgctgatg gtgaacatca tgatcgacag cacgctacaa
2581 cccacgcccc agtgcaacccg cggcaacgac aacctgccgt ccatgccggt cggcatgcag
2641 ggcctgcaca cggcctgcct gaagctgcct gaagctgggg ctggatctgg agtctgcgaa atttcaggac
2701 ctgaacaaac acatcgccga ggtgatgctg ctgtcggcga tgaagaccag caacgcgctg
```

FIG. 11B

```
2761  tcgttcgcg  gggcccgtcc  cttcaaccac  tttaagcgca  gcatgtatcg  cgccggccgc
2821  tttcactggg  agcgctttcc  ggacgcccgg  ccgcggtacg  agggcgagtg  ggagatgcta
2881  cgccagagca  tgatgaaaca  cggcctgcgc  aacagccagt  ttgtcgcgct  gatgccacc
2941  gccgcctcgg  cgcagatctc  ggacgtcagc  gagggctttg  cccccctgtt  caccaacctg
3001  ttcagcaagg  tgacccggga  cggcgagacg  ctgcgcccca  acacgctcct  gctaaaggaa
3061  ctggaacgca  cgtttagcgg  gaagcgcctc  ctggaggtga  tggacagtct  cgacgccaag
3121  cagtggtccg  tgccgcaggc  gctcccgtgc  ctggagccca  cccacccct  ccggcgattc
3181  aagaccgcgt  ttgactacga  ccagaagttg  ctgatcgacc  tgtgtgcgga  ccgcgccccc
3241  tacgtcgacc  atagccaatc  catgaccctg  tatgtcacgg  agaaggcgga  cgggaccctc
3301  ccagcctcca  ccctggtccg  ccttctggtc  cacgcatata  agcgcggaac  aaaaacaggg
3361  atgtactact  gcaaggttcg  caaggcgacc  aacagcgggg  agcgcggact  tctttggcgg  cgacgacaac
3421  attgtctgca  tgagctgcgc  gctgtgaccg  acaaaccccc  acaaaccccg  cgacgacaac  gcccgccgcc
3481  actgtcgtcg  ccgtcccaag  ctctcccctg  ctgccatg
```

FIG. 11C

```
   1  gtgtgtttgg cgtgtgtctc tgaaatggcg gaaacccaca tgcaaatggg attcatggac
  61  acgttacacc ccctgactc  aggagatagg catatcctcc ttagattgac tcagcacacg
 121  atcgcaaccc acccctgtgt gccggggata aaagccaaacg cgcgcggtct gggttaccac
 181  aacaggtggg tgcttcgggg acttgacggt cgccactctc ctgcgagccc tcacgtcttc
 241  gcccaccgat tcctgttgcg ttcctgtcgg ccggtgtcgt cctgtcgaca gattgttggc
 301  gactgcccgg gtgattcgtc ggccggtgcg ggccggtgcg cgtaccgccc acccgcctc
 361  ccacgggccc gccgctgttt ccgttcatcg cgtccgagcc accgtcacct tggttccaat
 421  ggccaaccgc cctgccgcat ccgccctcgc cggagcgcgg tctccgtccg aacgacagga
 481  accccgggag cccgaggtcg cccccccctgg cggcgaccac gtgttttgca ggaaagtcag
 541  cggcgtgatg gtgctttcca gcgatccccc cggccccgcg gcctaccgca ttagcgacag
 601  cagctttgtt caatgcggct ccaactgcag tatgataatc gacggagacg tggcgcgcgg
 661  tcatttgcgt gacctcgagg gcgctacgtc caccgcgcc  ttcgtcgcga tctcaaacgt
 721  cgcagccggc ggggatggcc gaaccgcgt  cgtggcgctc gcggaaacct cgggcccgtc
 781  cgcgactaca tccgtgggga cccagacgtc cggggagttc ctccacggga acccaaggac
 841  ccccgaaccc caaggaccc  aggctgtccc ccgccccct  ctcccccct  ttccatgggg
 901  ccacggagtgc tgcgcccgtc gcgatgccag gggcggcgcc gagaaggacg tcgggccgc
 961  gggtcatgg  tcagacggcc cgtcgtccga ctcgaaaacg gaggactcgg actcctcgga
1021  cgaggatacg ggctcgggtt cggagacgct gtctcgatcc tcttcgatct gggccgcagg
1081  ggcgactgac gacgatgaca gcgactccga gcgactcccga ctcgcggtcg gacgactccg tgcagccga
1141  cgttgtcgtt cgtcgcagat gggagcgacgg ccctgcccc gtgcccc   ccaagcccg
1201  gcgccccggc gactcccccg gaaacccccg cctgggcgcc ggcaccggc  cgggctccgc
1261  gacgacccg  cgcgtcgg   ccgactccga ttccgcgggc cacgccgcg  caccccaggc
1321  ggacgtggcg ccggttctgg acagccagcc cactgtggga acggaccccg gtacccagt
```

FIG. 12A

```
1381 cccctagaa ctcacgccg agaacgcgga ggcggtggcg cggtttctgg gggacgccgt
1441 cgaccgcgag cccgcgtca tgctggagta cttctgtcgg tgcgcccgcg aggagagcaa
1501 gcgcgtgccc ccacgaacct tcggcagcgc cccccgcctc acggaggacg actttgggct
1561 cctgaactac gcgctcgctg agatgcgacg cctgtgcctg gaccttcccc cgtccccc
1621 caacgcatac acgccctatc atctgaggga gtatgcgacg cggctggtta acgggttcaa
1681 accctggtg cggcggtccg cccgcctgta tcgcatcctg gggattctgg ttcacctgcg
1741 catccgtacc cggagggcct cctttgagga atggatgcgc tccaaggagg tggacctgga
1801 cttcgggctg acggaaaggc ttcgcgaaca cgaggcccag ctaatgatcc tggccaggc
1861 cctgaacccc tacgactgtc tgatccacag caccccgaac acgctcgtcg agcggggct
1921 gcagtcggcg ctgaagtacg aagagttta cctcaagcgc ttcggcgggc actacatgga
1981 gtccgtcttc cagatgtaca cccgcatcgc cgggttcctg gcgtgccggg cgaccgcggg
2041 catgcgccac atcgcccctgg ggcgacaggg gtcgtggtgg gaaatgttca agttctttt
2101 ccaccgcctc tacgaccaac agatcgtgcc gtccacccc gccatgctga acctcggaac
2161 ccgcaactac tacacgtcca gctgatacct ggtaaacccc caggccacca ctaaccaggc
2221 caccctccgg gccatcaccg gcaacgtgag cgcgcatcctc gcccgcaacg gggcatcgg
2281 gctgtgcatg caggcgttca acgacgcacc cccggcacc gccagcatca tgccggccct
2341 gaaggtcctg gactccctgg tgcggcgca caacaaacag agcacgcgcc ccaccggggc
2401 gtgcgtgtac ctggaaacct ggcacacgga cgttcgggcc gtgctcagaa tgaagggcgt
2461 cctcgccggc gaggaggccc agcgctgcga caacatcttc agcgccctct ggatgccgga
2521 cctgttcttc aagcgcctga tccgccacct cgacttcac agcgccctct cctggtcct
2581 gttcgaccgg gacaccagca tcgagctcgc tgtcgctcgc cgactttcac ggcgaggagt tcgagaagct
2641 gtacgagcac ctcgaggcca tggggttcgg cgaaacgatc ccatccagg aaccggcgta acctggcgta
2701 cgccatcgtg cgcagcgcgg ccaccaccgg ccaccaccgg aagcccttc atcatgttta aggacgcggt
```

FIG. 12B

```
2761 aaacagccac tacatctacg acacgcaagg ggcggccatt gccggctcca acctctgcac
2821 gaagatcgtc cacccgtcct ccaaacgctc cagcggggtc tgcaacctgg gcagcgtgaa
2881 tctggcccga tgcgtctccc ggcggacgtt cgattttggc atgctccgcg acgccgtgca
2941 ggcgtgcgtg ctaatggtta atatcatgat agacagcacg ctgcagccga cgccccagtg
3001 cgcccgcgggc cacgacaacc tgcgtccat gggcattggc atgcagggcc tgcacacggc
3061 gtgcctgaag atgggcctgg atctggagtc ggccgagttc cgggacctga acacacacat
3121 cgccgaggtg atgctgctcg cggccatgaa gaccagtaac gcgctgtgcg ttcgggggc
3181 gcgtccttc agccacttta agcgcagcat gtaccgggcc ggccgctttc actgggagcg
3241 cttttcgaac gccagcccgc ggtacgaggg gccagttcat cgcgctcatg atgctacgcc agagcatgat
3301 gaaacacggc ctgcgcaaca gccagtcacc gcttcaccac cccaccgccg cctcggccca
3361 gatctcggac gtcagccagg gctttgcccc gcccaacac acctgtcacc aacctgttca gcaaggtgac
3421 cagggacggc gagacgctgc gagacgctgg acgagccgag cgggctcgag gccaagcagt agcgcacgtt
3481 cggcggggaag cggctcctgg acgtcctgg accccgccca ccccccccgg cggttcaaga ggtctgtggc
3541 ccaggccctg ccttgcctga aactgctga acccgcgcca tgcagaccgc cgggctcaaga cggccttcga
3601 ctacgaccag gaactgctga actctgtatg tcacagagaa tgcagaccgc gccccctatg ttgatcacag
3661 ccaatccatg actctgtatg ctcgtccacg catataagcg ggcggacggg acgctccccg cctccaccct
3721 gtccgccttt ctcgtccacg catataagcg cggcctgaag acgggatgt actactgcaa
3781 ggttcgcaag gcgaccaaca gcggggtgtt cgccgagcgac gacaacatcg tctgcacaag
3841 ctgcgcgctg taagcaacag cgctccgatc gggtcaggc gtcgtctcg gtcccgcata
3901 tcgccatgga tcccgcgtc tccccgcga gcaccgacc cctagatacc cacgcgtcgg
3961 gggccggggc ggcccccgatt ccggtgtgcc ccaccccga gcggtacttc tacacctccc
4021 agtgccccga catcaaccac cttcgctccc tcagcatcct gaaccgctgg ctggagaccg
4081 agctcgtgtt cgtcggggac gaggaggacg tctccaagct ctccgagggc gagctcggct
```

FIG. 12C

```
4141  tctaccgctt tctgtttgcc ttcctgtcgg ccgcggacga cctggtgacg gaaaacctgg
4201  gcggcctctc cggcctcttc gaacagaagg acattcttca ctactacgtg gagcaggaat
4261  gcatcgaggt cgtccactcc cgctctacaa acatcatcca gctggtgctc tttcacaaca
4321  acgaccaggc gcgccgcgcc tatgtggccc gcaccatcaa ccacccggcc attcgcgtca
4381  aggtggactg gctggaggcg cgggtgcggg aatgcgactc gatcccggag aagttcatcc
4441  tcatgatcct catcgagggc gtcttttttg ccgcctcgtt cgccgccatc gcgtacctgc
4501  gcaccaacaa cctcctgcgg gtcacctgcc agtcgaacga cctcatcagc cgccacgagg
4561  ccgtgcatac gacagcctcg tgctacatct acaacaacta cctcggggc cacgccaagc
4621  ccgaggcggc gcgcgtgtac cggctgtttc ggatatcgag gatatcgag atcgggttca
4681  tccgatccca ggccccgacg gacagctcta ggggccctg tcctgagtcc gcggccatcg
4741  agaactacgt gcgattcagc gcggatcgcc tgctgggcct gatccatatg cagcccctgt
4801  attccgcccc cgccccgac gcccccgac gccagcttc ccctcagcct catgtccacc gacaaacaca
4861  ccaacttctt cgagtgccgc agcacctcgt acgccggggc cgtcgtcaac gatctgtgag
4921  ggtctgggcg ccctgtagc gatgtctaac cgaaataaag gggtcgaaac ggactgttgg
4981  gtctccggtg tgattattac gcaggggagg ggggtggcgg ctgggaaag ggaaggaacg
5041  cccgaaaacca gagaaaagga ccaaaaggga aacgcgtcca accgataaat caagcgccga
5101  ccagaacccc gagatgcata ataacaaacg atttattac tcttattatt aacaggtcgg
5161  gcatcgggag gggatggggg cgcgcgtttc ctccgttccg gctactcgtc ccagaattta
5221  gccaggacgt ccttgtaaaa cgcgggcggg ggcgcgtggg cccacacctg cgccagaaac
5281  cggtcggcga tgtccgggc ggtgatatga cgagtcacga tggagcgcgc taaatcttcg
5341  tcgcggaggt cctgatagat ggcagtctt tttagaagag tccagggtcc cgctccttg
5401  gggctgataa gcagatatgac gtacttgacg tatctgtgct ccaccagctc ggcgatggtc
5461  atcggatcgg gcagccagtc cagggcctcc caggcgtcgt ggatgacgt gcggcgacgt
```

FIG. 12D

```
5521  ccggcgacat  agccgcggtg  ttccgcgacc  cgctgcgcgt  tggggacctg  cacgagctcg
5581  ggcggggtga  gtatctccga  ggaggacgac  cgggcgccgt  cgcgcggccc  accggcgacg
5641  tccggggct   ggaggggggg  gtcttcttcg  tagtcgtcct  cgcccgcgat  ctgttgggcc
5701  agaatttcgg  tccacgagat  gccgcgtctcg aggccgaccg gggccgcggt  cagcgtaggc
5761  atgctctcca  gggagcgcga  gttggcgcgc  tcccgccggg  ccgcccggcg  ggcctgggat
5821  cggctcgggg  cggtccagtg  acactcgcgc  agcacgtcct  cgacggacgc  gtaggtgtta
5881  ttggggtgca  ggtctgtgtg  gcagcggacg  aacagcgcca  ggaactgcgg  gtaactcatc
5941  ttgaagtacc  ctgcag
```

*FIG. 12E*

```
   1 aaaccactgt tctttacact ttatgctcta gttttttggta atagtgtctt ggaacacttt
  61 taccctaaac gaaattatgg ctttggattt tttgagcacc gactgtccac tggggattgt
 121 ttcgatatt atatccaacg tgaataccat caaagagtat ggatattcca gcgaattatc
 181 aacaacgctg gcacctcgcc cgtctcgaga acaggtgtta gagtatatca ccagagtcgt
 241 ggataaactc aagccgctgt gcagagtcga cgaacgcctt tacattgcgt gcggggagct
 301 tgtacaccta cgaattaaag cacgcaacac agacctgaaa tattggctaa aatcgtctga
 361 gattgatctt agcgatgtcg tggaacaggc catattggaa cacattgact ttgttcagaa
 421 aaccctcaac tcgttttgaaa catcggaata ccgagatttg tgttcattag gcctgcaatc
 481 tgcgctaaag tatgaagaaa tgtatttagc caaaatgcga ggcggacgtc tagagtccat
 541 gggcaattt ttcttagac ttgcaactac tgctacgcac tatatttca aacaaccagc
 601 aatggctcgc gtgttggtta gcggtgaggt tggctggaca tatatgctgt gagccttttt
 661 tactgcgcta gccagacagg ttgtcattcc ggccacgcca attatgctgt ttggtgggag
 721 agactgtggg tctatggcca gctgttattt gctaaacccc agggtaacag atatgaactc
 781 tgcaattccg gctcttatgg aagaggttgg acccatttg tgcaaccgag gaggaattgg
 841 actgtctttta cagaggttta acactccacc cacagaaggt tgttcacggg gtgtcatggc
 901 tctcctaaag ctactagact ctatgaccat ggccattaac agcgacggtg aaagaccaac
 961 aggagtgtgt gtttattcg aaccctggca cgcaacatc cgcgccatt taaatatgcg
1021 cggaatgctg gccagagacg aaactgtgcg ctgcgacaac atctttgctt gtatgtggac
1081 cccagacctg ttttttgacc ctatcaacg gtacgtcgat gtacgtcgat gaagaaagcg gcataatgtg
1141 gactctgttt gatgatactg catcgcacct ctgccatatg ggagaaatg atttcacacg
1201 ggaatatgag cgcctgggc ggtggatt tgggatagac tgggatagac tacggaaatg gctattccca tacaggacat
1261 ggcctttatc atagttagaa gtgctgtaat gacaggaagc ccatttttga tgtttaaga
1321 cgcgtgcaac aggcactacc actttgacat gcggcagaga ggtgcgataa ggtgtctaa
```

*FIG. 13A*

```
1381 tctatgcaca gaaattatcc agcatgccga cgaaacccaa aacggggtgt gtaatctagc
1441 cagcatcaac ctccaaaat gtctagccct tccacctcca aatattgcag gtgtgccata
1501 ttttgactc gccgctctgg gccgcgctgc cgcaactgcc acaattttg tcaatgcat
1561 gatgtgtgcc agcacatatc caactgttaa atcccagaaa ggcgttgaag aaaaccggtc
1621 gctgggactt ggaattcagg ggctacatac cacgttttg atgctggacc tggatatggc
1681 atctccagag gcgcaccaac taaacaagca aatagcagaa aggctgttat tgaactctat
1741 gaaggccagc gcaacgctct gcaagctggg tatgcaacc tttaaaggt ttgaagacag
1801 caagtacagt cgggggaac tacccttga tgcctaccca aatgtaacac taacaaacg
1861 caacgcctgg cgtagactc gcactgacat aaaacaatac ggcttgtaca attctcagtt
1921 tgtagcctat atgccaacag tatcttcgtc acaggttacc gagagcagcg aggggttttc
1981 tcctgttac acaaacctgt ttagcaaagt tactgctacc ggggagtac tcaggcccaa
2041 tgtactgcta atgccacca tcagaagtat ttttccacag gaatgcgcgc gcttacaagc
2101 gctatctacg ctagaagctg cgaaatggtc agttgtggga gcgtttggtg atttgccagt
2161 tggtcacccc ctcagtaagt ttaaaacagc atttgagtac gaccagacta tgctaattaa
2221 catgtgtgct gacagggctg cgtttgtgga ccagttgga tccatgtctt tgtttataac
2281 tgagcctgct gacggaaaac tccccgcctc cagaattatg aatctttggg tccacgcata
2341 taaacgcgga cttaaaaacag gcatgtacta ctgcaaaatc aagaaggcaa caaacaacgg
2401 agtctttgtt ggcggagacc tagtctgcagc cagctgcagc ttgtagggca gcctgccat
2461 tttgcccagg gcggaaaat aattatgcc ctcgaaaact ctaaaaaaac agattttgct
2521 gacgagttat tgataaatgc gtatttctat acgccggaat gtcccgatat tgaacaccta
2581 cgcttgttga gcgttgccaa ccgctggctg gatacggacc ttccaattc tgatgacctc
2641 aaggacgttg ctaaactcgc gccagccgag cgagagtttt accggttttt gtttgccttt
```

FIG. 13B

```
2701 ttatctgctg ctgacgactt ggtaaattta aacctgggag atttatccgc actattact
2761 caaaggaca ttcttcacta ctacattgag caagagtcta ttgaagtaac gcactccaga
2821 gtatatagcg ctatacagct tatgttgttt ggaaacgacg caacagcgcg cgctaggtat
2881 gtcgcatctg ttgtcaaaga cgtggccata tatcttggtt gcaagcaaag
2941 gtgcgagaat gcaaatctgt ggcggaaaag tatattttga tgatattaat agggcgtt
3001 ttcttcgcgt cgtccttcc gtccatcgca totcttcgca cccacaatct ctttgtggta
3061 acctgtcaaa gtaatgattt aattagccgc gacgaagcaa ttcacaccaa cgcctcgtgc
3121 tgtatctaca acaactacct tgggcgtttt gaaaagccag ctccaacgag gatttatgcg
3181 ctgtttctg oggccgtaaa catcgagtgt gaattttttgc tttcccatgc cccaaaagc
3241 agccacctgt tggacattga agccatcata tgctacgtac gctatagcgc ggacaggctt
3301 ttggggaaa ttggactatc tccgctgttt aatgctccca aaccccaca aagcttcccc
3361 ctagctttca tgactgtgga aaaacatacc aactttttg aaggcgaag caccgcatac
3421 tcgggaactc ttatataaacga tctgtaatgt aaaaataaaa actaattttg attcacttat
3481 ttgtcttgtt tgcgtgttgg atgtacgcga tttaaaaaaa tactgagaaa agatactccc
3541 gatttaactt tattaagac cattgtcttc ggtgtccaca gtcatccaca tagttaacca
3601 acacagtgtt gtaatcagtg gggtggga tgtggttcca aaacatatta gcaagctctc
3661 tgacaatttc gtgttcgg
```

FIG. 13C

SEQUENCE LISTING

<160> NUMBER OF SEQ ID NOS: 265

<210> SEQ ID NO 1
<211> LENGTH: 2286
<212> TYPE: DNA
<213> ORGANISM: Escherichia coli

<400> SEQUENCE: 1

| | | | | | |
|---|---|---|---|---|---|
| atgaatcaga | atctgctggt | gacaaagcgc | gacggtagca | cagagcgcat | caatctcgac | 60 |
| aaaatccatc | gcgttctgga | ttgggcggca | gaaggactgc | ataacgtttc | gatttcccag | 120 |
| gtcgagctgc | gctcccacat | tcagttttat | gacggtatca | agacctctga | catccacgaa | 180 |
| accattatca | aggctgccgc | agacctgatc | tcccgtgatg | cgccggatta | tcagtatctc | 240 |
| gccgcgcgcc | tggcgatctt | ccacctgcgt | aaaaaagcct | acggccagtt | tgagccgcct | 300 |
| gcgctgtacg | accacgtggt | gaaaatggtc | gagatgggca | aatacgataa | tcatctgctg | 360 |
| gaagactaca | cggaagaaga | gttcaagcag | atggacacct | ttatcgatca | cgaccgtgat | 420 |
| atgaccttct | cttatgctgc | cgttaagcag | ctggaaggca | aatatctggt | acagaaccgc | 480 |
| gtgaccggcg | aaatctatga | gagcgcccag | ttcctttata | ttctagttgc | cgcgtgcttg | 540 |
| ttctcgaact | acccgcgtga | aacgcgcctg | caatatgtga | agcgttttta | cgacgcggtt | 600 |
| tccacattta | aaatttcgct | gccgacgcca | atcatgtccg | gcgtgcgtac | cccgactcgt | 660 |
| cagttcagct | cctgcgtact | gatcgagtgc | ggtgacagcc | tggattccat | caacgccacc | 720 |
| tccagcgcga | ttgttaaata | cgtttcccag | cgtgccggga | tcggcatcaa | cgccgggcgt | 780 |
| attcgtgcgc | tgggtagccc | gattcgcggt | ggtgaagcgt | tccataccgg | ctgcattccg | 840 |
| ttctacaaac | atttccagac | agcggtgaaa | tcctgctctc | agggcggtgt | gcgcggcggt | 900 |
| gcggcaacgc | tgttctaccc | gatgtggcat | ctggaagtgg | aaagcctgct | ggtgttgaaa | 960 |
| aacaaccgtg | gtgtggaagg | caaccgcgtg | cgtcatatgg | actacggggt | acaaatcaac | 1020 |
| aaactgatgt | atacccgtct | gctgaaaggt | gaagatatca | ccctgttcag | cccgtccgac | 1080 |
| gtaccggggc | tgtacgacgc | gttcttcgcc | gatcaggaag | agtttgaacg | tctgtatacc | 1140 |
| aaatatgaga | aagacgacag | catccgcaag | cagcgtgtga | aagccgttga | gctgttctcg | 1200 |
| ctgatgatgc | aggaacgtgc | gtctaccggt | cgtatctata | ttcagaacgt | tgaccactgc | 1260 |
| aatacccata | gcccgtttga | tccggccatc | gcgccagtgc | gtcagtctaa | cctgtgcctg | 1320 |
| gagatagccc | tgccgaccaa | accgctgaac | gacgtcaacg | acgagaacgg | tgaaatcgcg | 1380 |
| ctgtgtacgc | tgtctgcttt | caacctgggc | gcaattaata | acctggatga | actggaagag | 1440 |

-continued

```
ctggcaattc tggcggttcg tgcacttgac gcgctgctgg attatcagga ttacccgatc    1500
ccggccgcca acgtggagc gatgggtcgt cgtacgctgg gtattggtgt gatcaacttc    1560
gcttactacc tggcgaacga cggtaaacgc tactccgacg gcagcgccaa caacctgacg    1620
cataaaacct tcgaagccat tcagtattac ctgctgaaag cctctaatga gctggcgaaa    1680
gagcaaggcg cgtgcccgtg gtttaacgaa accacttacg cgaaagggat cctgccgatc    1740
gatacctata agaaagatct ggataccatc gctaatgagc cgctgcatta cgactgggaa    1800
gctctgcgtg agtcaatcaa aacgcacggt ctgcgtaact ccacgctttc tgctctgatg    1860
ccgtccgaga cttcttcgca gatctctaac gccactaacg gtattgaacc gccgcgcggt    1920
tacgtcagca tcaaagcgtc gaagacggt attttgcgcc aggtggtgcc ggactacgag    1980
cacctgcacg acgcctatga gctgctgtgg gaaatgccgg gtaacgatgg ttatctgcaa    2040
ctggtgggta tcatgcagaa atttatcgat cagtcgatct ctgccaacac caactacgat    2100
ccgtcacgct tcccgtcagg aaaagtgccg atgcagcagt tgctgaaaga cctgctcacc    2160
gcctacaaat tcgggtcaa acactgtat tatcagaaca cccgtgacgg cgctgaagac    2220
gcacaagacg atctggtgcc gtcaatccag gacgatggct gcgaaagcgg cgcatgtaag    2280
atctga                                                              2286
```

<210> SEQ ID NO 2
<211> LENGTH: 1560
<212> TYPE: DNA
<213> ORGANISM: Escherichia coli

<400> SEQUENCE: 2

```
ctggtgccgt caatccagga cgatggctgc gaaagcggcg catgtaagat ctgatattga     60
gatgccggat gcggcgtaaa cgccttatcc ggcctacggc tcggtttgta ggcctgataa    120
gacgcgccag cgtcgcatca ggctccgggt gccggatgca gcgtgaacgc ttatccggc    180 ctacggctcg gatttgtagg cctgataaga cgcgccagcg tcgcatcagg cacaggatgc    240
ggcgtaaaat gccttatccg gcattaaact cccaacagga cacactcatg catatacca    300 ccttttcaca gacgaaaaat gatcagctca agaaccgat gttctttggt cagccggtca    360
acgtggctcg ctacgatcag caaaaatatg acatcttcga aaagctgatc gaaaagcagc    420
tctctttctt ctggcgtccg gaagaagttg acgtctcccg cgaccgtata gattaccagg    480
cgctgccgga gcacgaaaaa cacatctttta tcagcaacct gaaatatcag acgctgctgg    540
attccattca gggtcgtagc ccgaacgtgg cgctattgcc gcttatttct attccggaac    600
tggaaacctg ggtcgaaacc tggcgttct cagaaacgat tcattcccgt tcctatactc    660
atatcattcg taatatcgtt aacgatccgt ctgttgtgtt tgacgatatc gtcaccaacg    720
agcagatcca gaaacgtgcg gaagggatct ccagctatta cgatgagctg atcgaaatga    780
ccagctactg gcatctgctg ggcgaaggta cccacaccgt taacggtaaa actgtgaccg    840
ttagcctgcg cgagctgaag aaaaaactgt atctctgcct gatgagcgtt aacgcgctgg    900
aagcgattcg tttctacgtc agctttgctt gttccttcgc atttgcagaa cgcgaattga    960
tggaaggcaa cgccaaaatt attcgcctga ttgcccgcga cgaagccctg cacctgaccg   1020
gcacccagca tatgctgaat ctgctgcgca gcggcgcgga cgatcctgag atggcggaaa   1080
ttgccgaaga gtgtaagcag gagtgctatg acctgtttgt tcaggcagct caacaggaga   1140
aagactgggc ggattatctg ttccgcgacg gttcgatgat tggtctgaat aaagacattc   1200
tctgccagta cgttgaatac atcaccaata tccgtatgca ggcagtcggt ttggatctgc   1260
```

-continued

```
cgttccagac gcgctccaac ccgatcccgt ggatcaacac ttggctggtg tctgataacg    1320
tgcaggttgc tccgcaggaa gtggaagtca gttcttatct ggtcgggcag attgactcgg    1380
aagtggacac cgacgatttg agtaacttcc agctctgatg gcccgcgtta ccctgcgcat    1440
cactggcaca caactgctgt gccaggatga acacccttcc cttctggcgg cgctggaatc    1500
ccacaatgtg gcggttgagt accagtgtcg cgaaggttac tgcggctcct gtcgcacacg    1560
```

<210> SEQ ID NO 3
<211> LENGTH: 4594
<212> TYPE: DNA
<213> ORGANISM: Salmonella typhimurium

<400> SEQUENCE: 3

```
gtgaacgtcg atctggtgcc ggatgcagcg gatacgctcc gggcgcaagg atttcgtcaa      60
ttaccggtgg tgatggcggg cgatttgagc tggtctggct tccgcccgga catgattaac     120
cgtctgcacc cgacacccca cgcggcaaac gcatgagcgc gctcgtctac ttctccagca     180
gctctgaaaa tacgcaccgc tttatgcagc gtctggggct gcctgccacg cgtattccgc     240
tcaatgagcg ggagcgaatt caggtagacg aaccgtacat tctggttgtg ccgtcatacg     300
gcggcggcgg gatggccggt gcggtgccgc gacaggtgat ccgcttttta aatgatgaac     360
acaaccgggc gcgcattcgc ggcgttatcg cctccggtaa tcgcaatttc ggcgatgcct     420
ggggatgcgc tggcgatgtg atagcacaaa atgcgcgt cccctggctg taccgctttg     480
agctcatggg cacacaacgc gacatcgata atgtccgaaa aggagtaaat gaattttggc     540
aacaactacc ccggagcgcg taatgcagga accatggata taccacgccc tgaacgcgat     600
gctgaatctt tacgataaag caggccatat tcagttcgac aaggaccagc aggcgatcga     660
cgccttcttt gccacccacg tccgcccgca ttccgtgacg tttgccagcc agcatgaacg     720
tctggggacg ctggttcggg aagggtatta cgatgacgcc gtcctcgcgc gttacgaccg     780
cgccttcgtc cttcgcctgt tcgagcacgc ccatgccagc ggctttcgct tccagacgtt     840
tcttggcgcc tggaagttct ataccagtta cacgctgaaa accttcgacg gcaaacgtta     900
tctggaacac tttgaagatc gggtgacaat ggtggcgttg acgctggcgc agggtgacga     960
aacgctggcc acccaactga ccgatgaaat gctttctggt cgctttcagc ccgctacccc    1020
gactttttta aattgcggca aacagcagcg tggggaactg gtctcctgct tcctgctccg    1080
tatcgaagac aacatggagt cgatcgggcg ggcggtgaat tcggcgctgc aactctccaa    1140
acgcggcggc ggcgtcgcgt ttttactctc caatctgcgc gaggcgggcg cgccgatcaa    1200
acgcattgag aatcagtctt ccggcgtgat cccggtgatg aaaatgctgg aagacgcgtt    1260
ttcgtatgcc aaccaacttg gcgcgcgcca ggggccggc gcggtttatc tccatgcgca    1320
ccatccggat attctgcgtt ttctggatac caaacgagaa aacgctgacg aaaaaatccg    1380
gatcaaaacg ctctctctcg gcgtggtgat cccggatatc accttccggc tggcgaaaga    1440
aaacgcgcaa atgcgctct tttcgcccta tgacatacaa cgacgctacg gcaaaccgtt    1500
tggcgatatc gccattagcg aacggtacga tgaattaatt gccgatccgc acgtgcgcaa    1560
aacctatatt aacgcccgtg actttttca aacactggcg gagattcagt tcgaatccgg    1620
gtatccctac atcatgtttg aagatacggt aaaccgcgcg aatcccattg ctggtcgcat    1680
taatatgagc aacctgtgct cagaaatttt acaggtcaat agcgcttccc gttacgacga    1740
taaccttgac tatacccaca tcgggcatga catctcctgc aatctcggct cgctgaatat    1800
```

-continued

```
cgctcacgtc atggattcac cggacattgg ccgtaccgta gaaaccgcta ttcgcggcct    1860
gacggcggtg tcggacatga gccatatacg cagcgtgccc tcaatagccg ccggtaatgc    1920
cgcctctcat gccatcggtc tgggccagat gaatctgcat ggctatctgg cgagggaagg    1980
tattgcctac ggttcgccgg aggcgttgga tttcaccaat ctctatttt acaccattac    2040
ctggcatgcc gtgcatactt caatgcggct agcccgcgaa cgcggcaaaa ccttcgccgg    2100
atttgcgcag tcgcgctatg ccagcggcga ctattttacg cagtatttac aggacgactg    2160
gcaaccgaaa acagcgaaag tcaggcgct atttgcccgc agcggcatta cgctgcccac     2220
acgagaaatg tggctaaagc tgcgcgacga tgtgatgcgc tatggcatct ataaccaaaa    2280
tttgcaggcg gtgccgccga ccggttcgat ttcttacatt aatcatgcga cctccagcat    2340
tcatccgatt gtggccaaaa ttgagattcg caaagagggc aaaaccgggc gtgtgtatta    2400
ccccgcgccg tttatgacca atgaaaacct ggacatgtat caggatgctt acgatatcgg    2460
tccggaaaaa attattgata cctatgccga ggccacgcgc cacgtcgatc aagggctgtc    2520
gctcaccctg ttttttcccg ataccgccac gacccgcgat atcaacaagg cgcagatcta    2580
tgcctggcga aaaggtatta agtccctgta ttacatccgg cttcgccagt tggcgctgga    2640
aggtactgaa attgaaggct gcgtatcctg cgcgctataa ggaaagccat atgaaattat    2700
ctcgtattag cgccatcaac tggaacaaga tccaggacga caaagatctg gaggtatgga    2760
accggctgac cagtaacttc tggctgccgg aaaaagtgcc gttatcgaat gatattccgg    2820
cctggcagac gctgagcgcc gccgaacagc agctcaccat tcgcgtgttt acgggactta    2880
cgctgctcga cactatccag aacatcgcag gcgcgccgtc gttaatggca gatgccatca    2940
cgccgcatga agaggcagtg ctgtcgaaca tcagctttat ggaagcggta cacgcccgct    3000
cttacagttc tatttttctcc acgctgtgcc agacgaaaga ggttgatgcc gcctacgcct    3060
ggagcgaaga aaacccaccg cttcagcgta aggcgcagat tattttagct cattacgtca    3120
gcgatgaacc gctaaagaaa aagattgcca gcgtcttttt agagtctttt ctgttctatt    3180
ccggcttctg gttgccgatg tatttctcca gccgcggtaa gctcacgaac actgccgacc    3240
tgattcgttt aatcattcgc gatgaagcgg ttcacggtta ttatattggc tataagtatc    3300
agatagcgct acaaaaacta tcggcaatcg agcgtgaaga gttaaagctt ttcgcgctgg    3360
atttgttgat ggaactgtac gacaacgaaa tccgctacac agaagcgtta tatgcggaaa    3420
ccggctgggt taacgacgtc aaagccttct tgtgctacaa cgccaataaa gccttaatga    3480
acctgggtta tgaggcgtta tttccgccgg agatggcaga cgtgaatccc gcaatccttg    3540
ccgcgctctc gccgaatgcc gacgaaaacc atgatttctt ttccggctca ggttcatctt    3600
atgtgatggg gaaaacagtc gaaaccgaag acgaagactg gaatttttaa ccttacgggc    3660
atgggaaata acgttacatt tcccatgcct ttatttcaag caataggagg tcaaatcgcg    3720
caaatattac aacatgtcct acactcaata cgagtgacat tattcacctg gattccccca    3780
attcaggtgg attttttgctg gttgttccaa aaaatatctc ttcctcccca ttcgcgttca    3840
gcccttatat catgggaaat cacagccgat agcacctcgc aatattcatg ccagaagcaa    3900
attcaggggtt gtctcagatt ctgagtatgt tagggtagaa aaaggtaact atttctatca    3960
ggtaacatat cgacataagt aaataacagg aatcattcta ttgcatggca attaaattag    4020
aagtgaagaa tctgtatcaaa atatttggag agcatccgca gcgtgccttc aaatatattg    4080
aaaagggact atcgaaagag caaatactgg aaaaacgggg ctatcgcatt ggcgttaaag    4140
acgccagtct ggccattgaa gaaggcgaga tatttgtcat catgggatta tccggctcgg    4200
```

```
gtaaatccac aatggtacgc cttctcaatc gcctgattga acccacccgc ggacaggtac    4260
tgattgacgg cgttgatatt gccaaaatat cagacgctga gcttcgcgag gtgcgcagga    4320
aaaagattgc gatggtcttc cagtcatttg cgctcatgcc gcatatgacc gtgctggata    4380
atacggcatt cggtatggaa ttagcgggca tcgcggcgca agagcgtcgc gaaaaagcgc    4440
tggacgcctt gcgtcaggtg gggcttgaga attacgctca cgcctacccg gatgaacttt    4500
ccggtgggat gcgtcagcgt gttgggcttg cccgcgcgct ggcaatcaac cctgatatct    4560
tattaatgga tgaagcgttt ccgccctcg atcc                                 4594

<210> SEQ ID NO 4
<211> LENGTH: 1033
<212> TYPE: DNA
<213> ORGANISM: Lactococcus lactis

<400> SEQUENCE: 4
gaattcttat tttccctagc tttggattta ttctcacttc ctatgatctt ttattctcga     60
ttattatttt tgctttggca attattatca tttttcgaca taaacaaac ctcaaaagaa     120 tcaaaaatca ttgtgaatcc cttgtcccct ttggtttaaa cttatcgaga caaaagaaa     180 aatagcacaa tatattgtgt tgtttttctt tttttacata atttaacact atatctagta    240
tctttaattt gactagatat tttttttacg ctaaataaga ctataaaaac tcgagaaaaa    300
gtcaaggact ttttactccc gtctaaaaaa tatattggcc caaaggaga tttaaaatgg    360 ttacagttta ttctaaaaac aattgtatgc aatgcaaaat ggtcaaaaaa tggctttctg    420
aacacgaaat tgcatttaac gaaatcaata ttgatgaaca gcctgaattt gtcgaaaaag    480
taattgaaat gggttttcga gctgctcctg taatcacaaa agatgatttc gccttttctg    540
gtttccgtcc ttctgaatta gcaaagttgg cttaatatga acttgctta ttcagtgtg    600 actggacaaa cgcgtcgttt tgtttctaaa acagacttgc cgaatgtcga aattacacct    660
gacgatgatt tagagatgga cgagcctttc cttttgataa ctccctctta tgctgaagaa    720
tcaccaaccg tttctaaatc aatagacgtt atggactcgg ttttttgactt tatggcttat    780 aatgataatt ataaacattg tcgtggaatt atcggcactg gaaatcgtaa ttttgctggc    840
atctatattt ttaccgctaa agaagtttca gcaaatatc aaattccact tttatatgat    900
tttgagttta atggtacgcc agctgatgtt gctgctgttg aaaaactcgc tgcacagctt    960
gatcaaggag cgaaagtcac ctttaaaaat ccgctgtgat ttttatggc ttcaccctat   1020 ttgagtgaag ctt                                                      1033

<210> SEQ ID NO 5
<211> LENGTH: 3811
<212> TYPE: DNA
<213> ORGANISM: Escherichia coli

<400> SEQUENCE: 5
cagctgtact ggcataacga catttatact gtcgtataaa attcgactgg caaatctggc     60
actctctccg gccaggtgaa ccagtcgttt tttttgaat tttataagag ctataaaaaa    120
cggtgcgaac gctgttttct taagcacttt tccgcacaac ttatcttcat tcgtgctgtg    180
gactgcaggc tttaatgata agatttgtgc gctaaatacg tttgaatatg atcgggatgg    240
caataacgtg agtggaatac tgacgcgctg gcgacagttt ggtaaacgct acttctggcc    300
gcatctctta ttagggatgg ttgcggcgag tttaggtttg cctgcgctca gcaacgccgc    360
```

```
cgaaccaaac gcgcccgcaa aagcgacaac ccgcaaccac gagccttcag ccaaagttaa    420
ctttggtcaa ttggccttgc tggaagcgaa cacacgccgc ccgaattcga actattccgt    480
tgattactgg catcaacatg ccattcgcac ggtaatccgt catctttctt tcgcaatggc    540
accgcaaaca ctgcccgttg ctgaagaatc tttgcctctt caggcgcaac atcttgcatt    600
actggatacg ctcagcgcgc tgctgaccca ggaaggcacg ccgtctgaaa agggttatcg    660
cattgattat gcgcatttta ccccacaagc aaaattcagc acgcccgtct ggataagcca    720
ggcgcaaggc atccgtgctg gccctcaacg cctcacctaa caacaataaa cctttacttc    780 atttttattaa ctccgcaacg cggggcgttt gagattttat tatgctaatc aaattgttaa    840
ctaaagtttt cggtagtcgt aacgatcgca ccctgcgccg gatgcgcaaa gtggtcaaca    900
tcatcaatgc catggaaccg gagatggaaa aactctccga cgaagaactg aaagggaaaa    960
ccgcagagtt tcgtgcacgt ctggaaaaag gcgaagtgct ggaaaatctg atcccggaag   1020 cttttcgccgt ggtacgtgag gcaagtaagc gcgtctttgg tatgcgtcac ttcgacgttc   1080
agttactcgg cggtatggtt cttaacgaac gctgcatcgc cgaaatgcgt accggtgaag   1140
gaaaaaccct gaccgcaacc ctccctcctt acctgaacgc actaaccggt aaaggcgtgc   1200
acgtagttac cgtcaacgac tacctggcgc aacgtgacgc cgaaaacaac cgtccgctgt   1260
ttgaattcct tggcctgact gtcggtatca acctgccggg catgccagca ccggcaaagc   1320
gcgaagctta cgcagctgac atcacttacg gtaccaacaa cgaatacggc tttgactacc   1380
tgcgcgacaa catggcgttc agccctgaag aacgtgtaca gcgtaaactg cactatgcgc   1440
tggtggacga agtggactcc atcctgatcg atgaagcgcg taccgctg atcatttccg   1500 gcccggcaga agacagctcg gaaatgtata acgcgtgaa taaaattatt ccgcacctga   1560
tccgtcagga aaagaagac tccgaaacct tccagggcga aggccacttc tcggtggacg   1620
aaaaatctcg ccaggtgaac ctgaccgaac gtggtctggt gctgattgaa gaactgctgg   1680
tgaaagaggg catcatggat gaaggggagt ctctgtactc tccggccaac atcatgctga   1740
tgcaccacgt aacggcggcg ctgcgcgctc atgcgctgtt tacccgtgac gtcgactaca   1800
tcgttaaaga tggtgaagtt atcatcgttg acgaacacac cggtcgtacc atgcagggcc   1860
gtcgctggtc cgatggtctg caccaggctg tggaagcgaa agaaggtgtg cagatccaga   1920
acgaaaacca aacgctggct tcgatcacct tccagaacta cttccgtctg tatgaaaaac   1980
tggcggggat gaccggtact gctgataccg aagctttcga atttagctca atctacaagc   2040
tggataccgt cgttgttccg accaaccgtc caatgattcg taaagatctg ccggacctgg   2100
tctacatgac tgaagcggaa aaaattcagg cgatcattga agatatcaaa gaacgtactg   2160
cgaaaggcca gccggtgctg gtgggtacta tctccatcga aaatcggag ctggtgtcaa   2220 acgaactgac caaagccggt attaagcaca acgtcctgaa cgccaaattc cacgccaacg   2280
aagcggcgat tgttgctcag gcaggttatc cggctgcggt gactatcgcg accaatatgg   2340
cgggtcgtgg tacagatatt gtgctcggt gtagctggca ggcagaagtt gccgcgctgg   2400
aaaatccgac cgcagagcaa attgaaaaaa ttaaagccga ctggcaggta cgtcacgatg   2460
cggtactgga agcaggtggc ctgcatatca tcggtaccga gcgtcacgaa tcccgtcgta   2520
tcgataacca gttgcgcggt cgttctggtc gtcaggggga tgctggttct tcccgtttct   2580
acctgtcgat ggaagatgcg ctgatgcgta ttttgcttc cgaccgagta tccggcatga   2640
tgcgtaaact gggtatgaag ccaggcgaag ccattgaaca cccgtgggtg actaaagcga   2700
ttgccaacgc ccagcgtaaa gttgaaagcc gtaacttcga cattcgtaag caactgctgg   2760
```

-continued

```
aatatgatga cgtggctaac gatcagcgtc gcgccattta ctcccagcgt aacgaactgt   2820
tggatgtcag cgatgtgagc gaaaccatta acagcattcg tgaagatgtg ttcaaagcga   2880
ccattgatgc ctacattcca ccacagtcgc tggaagaaat gtgggatatt ccggggctgc   2940
aggaacgtct gaagaacgat ttcgacctcg atttgccaat tgccgagtgg ctggataaag   3000
aaccagaact gcatgaagag acgctgcgtg acggcattct ggcgcagtcc atcgaagtgt   3060
atcagcgtaa agaagaagtg gttggtgctg agatgatgcg tcacttcgag aaaggcgtca   3120
tgctgcaaac gcttgactcc ctgtggaaag agcacctggc agcgatggac tatctgcgtc   3180
agggtatcca cctgcgtggc tacgcacaga aagatccgaa gcaggaatac aaacgtgaat   3240
cgttctccat gtttgcagcg atgctggagt cgttgaaata tgaagttatc agtacgctga   3300
gcaaagttca ggtacgtatg cctgaagagg ttgaggagct ggaacaacag cgtcgtatgg   3360
aagccgagcg tttagcgcaa atgcagcagc ttagccatca ggatgacgac tctgcagccg   3420
cagctgcact ggcggcgcaa accggagagc gcaaagtagg acgtaacgat ccttgcccgt   3480
gcggttctgg taaaaaatac aagcagtgcc atggccgcct gcaataaaag ctaactgttg   3540
aagtaaaagg cgcaggattc tgcgcctttt ttataggttt aagacaatga aaaagctgca   3600
aattgcggta ggtattattc gcaacgagaa caatgaaatc tttataacgc gtcgcgcagc   3660
agatgcgcac atggcgaata aactggagtt tcccggcggt aaaattgaaa tgggtgaaac   3720
gccggaacag gcggtggtgc gtgaacttca ggaagaagtc gggattaccc cccaacattt   3780
ttcgctattt gaaaaactgg aatatgaatt c                                   3811
```

<210> SEQ ID NO 6
<211> LENGTH: 4045
<212> TYPE: DNA
<213> ORGANISM: Mycobacterium bovis

<400> SEQUENCE: 6

```
gatctacggc agaactcgtc gcttggagcg ttcgaccgac catctacctg ttcgacgtcg     60
aactcgacca ctgaacgtaa tcgccgccag cgcaagtcct gtcagcgcgt ggagatcacc    120
gcgcgtgggc gagggccggt ggtgcgaggt gaggcctgcg ccgacagctt ctatgccgcg    180
cttgaatcag cggtcgtcaa actggagagc gtgcgccgcg gtaaggatcg ccgcaaggtg    240
cactacggcg acaaaacccc ggtttcgctg gccgaggcga ccgcggtggt gccagcgccg    300
gagaacggct tcaacaccag accagccgag gcacacgatc acgacggtgc cgtcgtcgag    360
cgggagcctg ggcggatcgt tcgcaccaaa gaacacccgg ccaagccgat gtcggtcgat    420
gacgcgctct accagatgga gctggttgga cacgacttct tcttgttcta cgacaaggac    480
accgaacggc cgtcggtggt ctaccgccgg cacgcctacg actacggctt gatccgtctg    540
gcgtgatcgg cggcgcgcgc cgctcgtcac ctaccatggg agtcgcctta tctaaagact    600
cctacacatg cggggacata gctgtgctgt cgaagttgct gcgccttggc gaaggtcgca    660
tggtcaagcg cctcaagaag gtggcggact atgtcggcac tttgtccgac gatgtcgaga    720
aactcaccga cgccgagctg agggcgaaaa ccgacgagtt caagcggcgg ctggccgacc    780
agaaaaaccc agaaaccctc gacgacctgt tgcccgaggc cttcgccgtg gcccgcgagg    840
ccgcctggcg ggtgctggac cagcggccgt tcgacgtgca ggtgatgggt gcggccgccc    900
tgcacctggg caacgttgcc gagatgaaga ccggtgaagg caagaccctg acctgtgtgt    960
tgcccgctta cctcaatgcg ctggccggca acggcgtgca catcgtcacc gtcaacgact   1020
```

-continued

```
acctggctaa acgcgacagt gagtggatgg gccgcgtgca ccgcttcctc gggcttcagg    1080
tcggggtgat tttcgccacc atgacacccg atgaacgccg ggtggcctat aacgccgaca    1140
tcacctacgg caccaataac gagtttgggt tcgactacct gcgcgacaac atggcgcact    1200
cactggatga tctggtgcag cgcgggcacc attacgccat tgtcgacgag gtcgattcca    1260
tcctgatcga cgaggcccgc accccgctga tcatctccgg tcccgccgac ggcctccaac    1320
tggtacaccg agttcgccgg ttggcgccgc tgatggaaaa ggacgtccac tacgaggtcg    1380
atctacgcaa acgcaccgtc ggcgtgcacg agaagggtgt ggaattcgtc gaagaccagc    1440
tcggcatcga caacctgtac gaggccgcca actcgccgtt ggtcagctat ctcaacaacg    1500
ctctgaaggc caagagctg ttcagccgcg acaaggacta catcgtccgc gatggtgagg    1560
tgctcatcgt cgacgagttc accggccggg tgctgatcgg ccgccgctac aacgagggca    1620
tcgaccaggc catcgaggcc aaggagcacg tcgagatcaa ggccgagaac cagacgctgg    1680
ccaccatcac gctgcagaac tacttccggc tctacgacaa gctcgccggc atgaccggca    1740
ccgcccagac ggaggcggcc gagctgcacg agatctacaa gctgggcgtg gtcagcatcc    1800
cgaccaacat gccgatgatc cgtgaagacc agtccgacct gatctacaag accgaggagg    1860
ccaagtacat cgcggtggtc gacgacgtcg ccgagcgcta cgcgaaggga cagccggtgc    1920
tgatcggcac caccagcgtg gagcgctcgg agtatctgtc gcggcagttc accaagcggc    1980
gcatcccgca caatgtgctc aacgccaagt accacgagca agaggcgacc atcatcgcgg    2040
tggcgggccg ccgcggcggc gtcaccgtcg ccaccaacat ggccggtcgc ggcaccgaca    2100
ttgtgctggg cggcaacgtc gactttctca ccgatcagcg gctgcgcgaa cggcctggat    2160
ccggtggaga cgcccgagga gtacgaggcg gcctggcact ccgaactgcc catcgtcaaa    2220
gaggaagcca gcaaggaggc caaggaagta atcgaggccg gcggctgtac gtgctgggca    2280
ccgagcggcc acgagtcgcg gcggatcgac aaccagttgc gtggccggtc cggccgccag    2340
gggaccccgg ggagtcgcgc ttctatttgt cgctgggtga cgagctgatg cgccgcttca    2400
atggcgcggc cttggagacc ttgttgacca ggctgaacct gccgacgac gtgccgatcg    2460
aagccaagat ggtcacccgg gccatcaaga gcgcccagac ccaggtcgag cagcagaact    2520
ttgaggtccg caagaacgtc ctcaaatacg acgaggtgat gaaccagcag cgcaaggtca    2580
tctacgccga gcgccggcgc atcctcgaag gcgaaaacct caaggaccag gcgctggaca    2640
tggtccgcga tgtcatcacc gcctacgtcg acggcgcgac cggcgaaggc tatgccgaag    2700
attgggatct ggacgcgttg tggacggcac tcaaaaccct ctatccggag gggatcaccg    2760
ccgactcgct gacccgcaag gaccacgaat tcgagcgcga cgatctcacc cgcgaggagt    2820
tgctggaggc actactcaag gacgccgaac gtgcctatgc cgcacgggaa gccgaactcg    2880
aggaaatcgc cggcgagggt gcgatgcgcc agctggaacg caacgtgctg ctcaacgtca    2940
tagaccgtaa gtggcgtgaa cacctctacg agatggacta cctcaaggag ggtatcgggc    3000
tgcgcgcgat ggcgcacggc gatccgttgg tcgagtacca gcgtgagggc tacgacatgt    3060
tcatggccat gctcgacggc atgaaagagg aatcggtcgg cttcctgttc aacgtcaccg    3120
tggaggcggt ccccgccccg ccggttgccc cggctgccga accgcagag cttgccgaat    3180
tcgccgccgc ggccgcagcc gcgggcagca acgcagcgcg gtcgatggtg gcgcgcgcga    3240
aagagctcca agtgcattac gcgccaaggg tgttgccagc gagtcgcccg ctttgaccta    3300
ttccggtccc gcggaggatg gctcggctca ggtgcagcgc aacggcggtg gagcccacaa    3360
gacgccggcc ggagtgccgg ccggtgctag ccggcgcgag cggcgcgaac gcgcccgccg    3420
```

-continued

```
acaaggccgc ggcgccaagc cgccgaaatc ggtcaagaag cgttagcgcg taggttgcag      3480
atgggtgtat cggtttctca gttcccagaa gtcacttccc ggcacacccc ggccccggcg      3540
cgcatgcaca tttcgttgca cggcgggcaa ggggttcgct aatctcaccc gttcgtcgac      3600
cttcgtcggc gtcggttctg ctggtagcgg ggttcggcgc tttcctggcg tttctcgact      3660
cgacaatcgt caacatcgcg ttcccggata tccagcgttc cttcccgtcc tacgacatcg      3720
ggagcctgtc ctggattctg aacggctata acatgctctt cgccgccttc atggttgcgg      3780
ccggcaggtt ggccgatttg ctgggccgca gacgacattc ctgtccggtg tgctggtgtt      3840
caccattgcg tccgggctgt gcgccgtcgc cggcagtgtc gagcagttgg tggcgttccg      3900
ggtgctgcag ggcatcgggg ctgcgatact cgtgcctcgt cgctcgcac tggtcgttga      3960 gggcttcgac cgggccgccg cgcgcacgct atcggcctgt ggggtgcggc ggcagcgatc      4020
cactagttct agagcggcgc accgc                                            4045
```

<210> SEQ ID NO 7
<211> LENGTH: 1433
<212> TYPE: DNA
<213> ORGANISM: Mycobacterium tuberculosis

<400> SEQUENCE: 7

```
tcaaacacca gaccagaagg aggcaacacg atcacggacg gtgccgttcg tcgagcggga       60
gcctggggcg gatcgttcgc accaaagaac aacccggcca cgccgatgtc ggtcgatgac      120
gcgctctacc agatggagct ggttggacac gacttcttct tgttctacga caaggacacc      180
gaacggccgt cggtggtcta ccgccggcac gcctacgact acggcttgat ccgtctggcg      240
tcatcggcgg cgcgcgccgc gtcgtcacct accatgggag tcgccttatc taaagactcc      300
tacacatgcg gggacatagc tgtgctgtcg aagttgctgc gccttggcga aggtcgcatg      360
gtcaagcgcc tcaagaaggt ggccgactat gtcggcactt tgtccgacga tgtcgagaaa      420
ctcaccgacg ccgagctgag ggcgaaaacc gacgagttca gcaggctgg ccgaccagaa      480 aaacccagaa accctcgacg acctgttgcc cgaggccttc accgtgcccc gcgagacccg      540
cctgccgggt gctggaccaa cgaccgttcg acgtgcaggt gatgggtacg accgccctgc      600
acctgggcga cgttgccgag atgtagaccg gtgaaggcaa gaccctgacc tgtgttttac      660
ccgcttacct caatgccctg gccgccaacg gcgtgcacgt agttaccgtc aacgactacc      720
tggctaaacg cgacagtgag tggatgggcc gcgtgcaccg cttcctcggg cttcaggtcg      780
gggtgatttt ggccaccatg acacccgatg aacgccgggt ggcctataac gccgacatca      840
cctacggcac caataacgag tttgggttcg actacctgcg cgacaacatg gcgcactcac      900
tggatgatct ggtgcagcgc gggcaccatt acgccattgt cgacgaaggt cgattccatc      960
ctgatcgacg agggcgggc cccccccca tctccgcccg gggcgccgc ctccaactgg      1020 ttcaccgagt tcgcccggtt ggcgtgccgc ggctggtttt ggacgtccac tacgaggtcg      1080
atctacgcaa acgcaccgtc ggcgtgcacg agaagggtgt ggaattcgtc gaagaccagc      1140
tcggcatcga caacctgtac gagaccgcca actgccgtt ggtcagctat ctcaacaacg      1200
ctctgaaggc caaagagctg ttcagccgcg acaaggacta catcgtccgc gatggtgagg      1260
tgctcatcgt cgacgagttc accggccggg tgctgatcgg ccgccgctac aacgagggca      1320 tgcaccagge catcgaggcc aaggagcacg tcgagatcaa ggccgagaac cagacgctgg      1380
ccaccatcac gctgcagaac tacttccggc tctaggagaa gctcgccggg atg            1433
```

<210> SEQ ID NO 8
<211> LENGTH: 3124
<212> TYPE: DNA
<213> ORGANISM: Staphylococcus aureus

<400> SEQUENCE: 8

| | | | | | |
|---|---|---|---|---|---|
| tggcttgatt | caaactagtg | aacaataaat | taagtttaaa | gcacttgtgt | ttttgcacaa | 60 |
| gttttttat | actccaaaag | caaattatga | ctatttcata | gttcgataat | gtaatttgtt | 120 |
| gaatgaaaca | tagtgactat | gctaatgtta | atggatgtat | atatttgaat | gttaagttaa | 180 |
| taatagtatg | tcagtctatt | gtatagtccg | agtcgaaaat | cgtaaaatat | ttataatata | 240 |
| atttattagg | aagtataatt | gcgtattgag | aatatattta | ttagtgataa | acttgttgac | 300 |
| aacagaatgt | gaatgaagta | tgtcataaat | atatttatat | tgattctaca | aatgagtaaa | 360 |
| taagtataat | tttctaacta | taaatgataa | gatatattgt | tgtaggccaa | acagtttttt | 420 |
| agctaaagga | gcgaacgaaa | tgggattttt | atcaaaaatt | cttgatggca | ataataaaga | 480 |
| aattaaacag | ttaggtaaac | ttgctgataa | agtaatcgct | ttagaagaaa | aaacggcaat | 540 |
| tttaactgat | gaagaaattc | gtaataaaac | gaaacaattc | caaacagaat | tagctgacat | 600 |
| tgataatgtc | aaaaagcaaa | atgattattt | acataaaatt | ttaccagaag | catatgcact | 660 |
| tgttagagaa | ggctctaaac | gtgtattcaa | tatgacacca | tataaagttc | aaattatggg | 720 |
| tggtattgca | attcataaag | gtgatatcgc | tgagatgaga | acaggtgaag | gtaaaacatt | 780 |
| aacagcgaca | atgccaacat | acttaaatgc | attagctggt | agaggtgttc | acgttattac | 840 |
| agtcaatgaa | tacttatcaa | gtgttcaaag | tgaagaaatg | gctgagttat | ataacttctt | 900 |
| aggtttgact | gtcggattaa | acttaaacag | taagacgaca | gaggaaaaac | gtgaagcata | 960 |
| cgcacaagac | attacttaca | gtactaataa | tgagctaggt | tttgattact | acgagataa | 1020 |
| catggtgaat | tattctgaag | atagggtaat | gcgtccatta | cattttgcaa | tcattgatga | 1080 |
| ggtggactca | attttaatcg | acgaggcacg | tacgccatta | attatttctg | gtgaagctga | 1140 |
| aaagtcaacg | tcactttata | cacaagcaaa | tgtttttgcg | aaaatgttaa | acaggacga | 1200 |
| tgattataaa | tacgatgaaa | aaacgaaagc | tgtacattta | acagaacaag | gtgcggataa | 1260 |
| agctgaacgt | atgttcaaag | ttgaaaactt | atatgatgta | caaaatgttg | atgttattag | 1320 |
| tcatatcaac | acagctttac | gtgcgcacgt | tacattacaa | cgtgacgtag | actatatggt | 1380 |
| tgttgatggc | gaagtattaa | ttgtcgatca | atttacagga | cgtacaatgc | caggccgtcg | 1440 |
| tttctcggaa | ggtttacacc | aagctattga | agcgaaggaa | ggcgttcaaa | ttcaaaatga | 1500 |
| atctaaaact | atggcgtcta | ttacattcca | aaactatttc | agaatgtaca | ataaacttgc | 1560 |
| gggtatgaca | ggtacagcta | aaactgaaga | agaagaattt | agaaatattt | ataacatgac | 1620 |
| agtaactcaa | attccgacaa | ataaacctgt | gcaacgtaac | gataagtctg | atttaattta | 1680 |
| cattagccaa | aaaggtaaat | ttgatgcagt | agtagaagat | gttgttgaaa | acacaaggc | 1740 |
| agggcaacca | gtgctattag | gtactgttgc | agttgagact | tctgaatata | tttcaaattt | 1800 |
| acttaaaaaa | cgtggtatcc | gtcatgatgt | gttaaatgcg | aaaaatcatg | aacgtgaagc | 1860 |
| tgaaattgtt | gcaggcgctg | gacaaaaagg | tgccgttact | attgccacta | acatggctgg | 1920 |
| tcggggtaca | gatatcaaat | taggtgaagg | cgtagaggaa | ttaggcggtt | tagcagtaat | 1980 |
| aggtacagag | cgacatgaat | ctcgtcgtat | tgatgaccag | ttacgtggtc | gttctggacg | 2040 |
| tcaaggtgat | aaagggggata | gtcgcttcta | ttattcatta | caagatgaat | taatgattcg | 2100 |
| ttttggttct | gaacgtttac | agaaaatgat | gagccgacta | ggtttagatg | actctacacc | 2160 |

-continued

```
aattgaatca aaaatggtat caagagctgt tgaatcagca caaaaacgtg tagaaggtaa      2220
taacttcgac gcgcgtaaac gtatcttaga atacgatgaa gtattacgta aacaacgtga      2280
aattatctat aacgaaagaa atagtattat tgatgaagaa gacagctctc aagttgtaga      2340
tgcaatgcta cgttcaacgt tacaacgtag tatcaattac tatattaata cagcagatga      2400
cgagcctgaa tatcaaccat tcatcgacta cattaatgac atcttcttac aagaaggtga      2460
cattacagag gatgatatca aaggtaaaga tgctgaagat attttcgaag tcgtttgggc      2520
taagattgaa gcagcatatc aaagtcaaaa agatatctta gaagaacaaa tgaatgagtt      2580
tgagcgtatg attttacttc gttctattga tagccattgg actgatcata tcgacacaat      2640
ggatcaatta cgtcaaggta ttcacttacg ttcttatgca caacaaaatc cattacgtga      2700
ctatcaaaat gaaggtcatg aattatttga tatcatgatg caaatatattg aagaagatac      2760 ttgtaaattc attttaaaat ctgtagtaca agttgaagat aatattgaac gtgaaaaaac      2820
aacagagttt ggtgaagcga agcacgtttc agctgaagat ggtaaagaaa agtgaaacc      2880 gaaaccaatc gttaaaggcg atcaagttgg tcgtaacgat gattgtccat gtggtagtgg      2940
taaaaaattc aaaaattgcc atggaaaata atgatataa aataactcct tccaattaaa      3000
cacctatagt ttgtgttatg ggaggagtct ttttatttta caagcgttaa atactttaaa      3060
aaatgtgaag aagttgttaa acgttgttat gtacttagtt ttaaaaaatc ggtttaggca      3120
tatg                                                                   3124
```

<210> SEQ ID NO 9
<211> LENGTH: 3589
<212> TYPE: DNA
<213> ORGANISM: Staphylococcus carnosus

<400> SEQUENCE: 9

```
cttgaacgtt acttcactaa tgtgccgaat gtgaatgcac atgtaaaagt gaaaacttat        60
gcaaattcta gcacaaaatc gaagttacaa ttccgcttaa tgacgtgaca cttcgtgcag       120
aagaaagaaa cgatgattta tgctggaatt gacaagatca ctaacaaatt agaatgtcaa       180
gttcgtaaat acaaaacacg tgtcaatcgt aagaaacgta agaaaagcga acatgaacca       240
ttcccagcaa ctccggaaac tccgccggaa acagctgttg atcatgataa agatgatgaa       300
attgaaatca tccgttctaa acaattcagc ttgaaaccaa tggattctga agaagcggta       360
ttacaaatgg atttacttgg tactgatttc ttcatcttca atgaccgtga aactgatggt       420
acaagcattg tttaccgccg taaagacgga aaatatggtt tgattgaaac tgttgaaaaa       480
ctaatatgtg atatttgaaa gggctcttgc tgcatttttct gctgcaagag tttctttttt       540
tgagaaagcc cttattaaga tttgattaat aaaaatacaa ttgattgatt tacacggggt       600
gtccatgtca aaataagagg gatgtattaa gttcataatt gtaatgtgag ctccgatgag       660
tgagcggcat atgattatga tatccatgtg gcacatgatg ttaacaaaaa gagaatgaaa       720
ctgtgagaag tacatcttga taaacacaac taggcagttt attaaaaat aatgaacagt       780 atcctatgag tttttaagta taaattaagc catataaatg gtaagataaa ttgttgtaag       840
ccaaacagtt tttataccaa aggagcgaac agaatggggt tttaacaaa aattgttgac       900 ggcaataaga gagaaatcaa acgcctaagt aagcaagctg acaaagtaat ctcattagaa       960
gaagaaatgt caattcttac tgatgaagaa attagaaata aaacaaaagc attccaagaa      1020
agattgcaag cagaagaaca tgtaagcaaa caagataaaa ttttagaaga aatattacct      1080
```

-continued

| | |
|---|---|
| gaagcatttg cgcttgtccg tgaaggagct aaacgtgtat ttaatatgac acctatcca | 1140 |
| gttcaaatca tgggtggtat cgccattcat aatggtgaca tttcagaaat gagaacaggt | 1200 |
| gaaggtaaaa cattaactgc aacgatgccg acttatttaa acgccttagc agcacgtggt | 1260 |
| gtgcatgtta ttacagtcaa tgaatacttg gcaagttctc aaagagaaga aatggccgag | 1320 |
| ttatataatt tccttggttt atcagtcgga ttgaacttga acagcttatc aacagaacaa | 1380 |
| aagcgtgaag cttataatgc agatattacg tatagtacaa ataatgaatt aggcttcgac | 1440 |
| tatttacgcg ataacatggt gaattattca gaagaacgtg ttatgcgtcc gcttcatttc | 1500 |
| gctatcattg atgaggtcga ctctatttta atcgatgaag cgcgtacacc attgattatt | 1560 |
| tcaggggaag ctgaaaaatc aacatctctt tatacacaag caaatgtttt cgctaaaatg | 1620 |
| ttaaaagcag aagatgatta taattatgat gaaaaaacaa aatcagtaca attaacagat | 1680 |
| caaggtgctg ataaagctga acgtatgttc aagttagata acttatatga tttgaaaaac | 1740 |
| gttgatatta tcacgcatat caatacagca ttacgtgcta actatacatt gcaacgcgat | 1800 |
| gtagattaca tggttgtaga tggagaagta ttgattgtcg accaatttac aggtcgaaca | 1860 |
| atgccaggtc gtcgattctc tgaaggactt caccaagcga ttgaggctaa agaagggtt | 1920 |
| caaattcaaa atgaatctaa aacaatggct tctatcacat tccaaaacta cttccgtatg | 1980 |
| tataataaat tagccggtat gacaggtact gctaaaacag aggaagaaga attccgtaac | 2040 |
| atttataata tgacagttac acaaattcca acgaaccgtc ctgttcaacg tgaagataga | 2100 |
| cctgacttga ttttcatcag ccaaaaaggc aagttcgatg ctgttgttga agatgttgtt | 2160 |
| gaaaaacata aaaaaggcca accaattctt ttaggtactg tagcggttga acaagtgaa | 2220 |
| tacatttcac aactattgaa aaaacgcggt gtgcgtcatg atgtcttaaa cgctaaaaac | 2280 |
| catgaacgcg aagctgaaat cgtatctaca gcaggtcaaa aaggtgcagt cacaatcgca | 2340 |
| acaaacatgg ctggtcgtgg taccgatatt aaattaggcg aaggtgttga agaattaggc | 2400 |
| ggccttgctg ttattggtac agaacgtcat gaatcacgcc gtatcgatga tcagttgcgt | 2460 |
| ggtcgttctg gacgacaagg tgaccgcgga gaaagccgtt tctatttatc attacaagat | 2520 |
| gagttgatgg tacgtttcgg ttctgaacgt ctgcaaaaaa tgatgggccg attaggtatg | 2580 |
| gatgactcta caccgattga atcaaaaatg gtatctcgag ctgttgaatc tgcacaaaaa | 2640 |
| cgtgttgaag gtaacaactt cgatgcacgt aaacgtatct agaatacga tgaagtttta | 2700 |
| cgtaaacaac gtgaaatcat ttatggtgaa cgtaataata ttatcgattc agaatcaagt | 2760 |
| tctgaattag tcattacaat gatacgctct acattagatc gtgcaatcag ttattatgta | 2820 |
| aatgaagaat tggaagaaat tgactatgcg ccgtttatta ttttgtgga agatgttttc | 2880 |
| ttdcacgaag gtgaagtcaa agaagatgaa atcaaaggta aaggtaaaga tcgtgaggat | 2940 |
| attttcgata cagtatgggc taaaattgaa aaagcttatg aagcacaaaa agccaatata | 3000 |
| cccgaccaat tcaatgaatt cgaacgtatg attttattac gttctattga tggaagatgg | 3060 |
| acagaccata tcgatacaat ggatcaatta cgtcaaggta tccatttacg ttcatacggt | 3120 |
| caacaaaacc cacttcgcga ctatcaaaat gaagggcacc aactatttga tacaatgatg | 3180 |
| gtcaatattg aagaagacgt cagcaaatat atccttgaaat caattatcac agtagatgat | 3240 |
| gatattgaac gtgataaagc aaaagaatat caaggacaac atgtatcagc tgaagatgga | 3300 |
| aaagaaaaag taaaaccgca accagttgtt aaagataatc acatcggaag aaatgatcct | 3360 |
| tgtccatgcg gcagcggtaa aaagtataaa aattgctgcg gtaaatagta agttgtatta | 3420 |
| ggaccactgt taaatagctt taagagagat gctcaattga aattgggtta tctttctaag | 3480 |

-continued

| | |
|---|---|
| ggctgtcagc ggtctttttt caatccaaca aaaatatgga tatatgctaa aataatagag | 3540 |
| taatctggaa aattaaactg gaattggaga gatatgaaaa tggaattat | 3589 |

<210> SEQ ID NO 10
<211> LENGTH: 1242
<212> TYPE: DNA
<213> ORGANISM: Bovine herpes virus

<400> SEQUENCE: 10

| | |
|---|---|
| cagtcaatgt cgctcttcgt gaccgagcca atggacggaa aggtgcccgc ctcccagatc | 60 |
| atgaacctcc tagtgtacgc ctataagaag ggccttaaga cggggctcta ctactgcaag | 120 |
| atccgcaagg ccaccaacaa cggcgtcttc acgggcggcg acctcgtgtg ctctgggtgc | 180 |
| cacctgtagc gacgcgcgcc gagcgcgatg gccgaggcgg cggacgcggc gaccctcacg | 240 |
| cgtaaataca aatactttta cgagaccgag tgccccgacc tagatcactt gcggtcgctc | 300 |
| agcgtcgcaa accgctggct ggagaccgag tttcccctag cggacgacgc caaggacgtg | 360 |
| gcgcggctca gcggcgccga gctggagttt taccgctttc tgttcgcgtt cctctcggcc | 420 |
| gccgatgacc tcgtgaacgt caacctcggg gacctgtccg agctgttcac ccaaaaagac | 480 |
| atcctgcatt actatatcga gcaggagtcc atcgaagtgg tgcactcgcg ggtgtacagc | 540 |
| gccatacagc tgctgctctt tagaaacgac gcggtggcgc gcgcgggcta cgtagagggc | 600 |
| gccctcggcg accggcggt ccggcgcaag gtggactggc tcgagcggcg cgtggccgcg | 660 |
| gcagagtcgg tggccgaaaa gtacgtgctc atgattctaa tcgagggcat ttttttctcc | 720 |
| tcctcgtttg cggcgattgc ctacctgcgc acccacaacc ttttcgtcgt gacgtgccaa | 780 |
| accaacgacc tcatcagccg cgacgaagcc gtgcacacgg ccgcgtcgtg ctgcatcttc | 840 |
| gacaactacc tcggcgggga gcggccgccg ccggcccgca tctacgagct gttccgcgaa | 900 |
| gcgtggaaat tgagcgcgag tttatttggt tgcgcgccgc gcggcagtca tatacttgac | 960 |
| gtggaggcta tttctgcgta cgtcgagtac agcgcggacc gcctgctcgc tgctatccag | 1020 |
| ctgcctcctc tgtttggcac cccgcctcct gggaccgatt ttcctttggc cctgatgact | 1080 |
| gccgagaagc acacgaactt ctttgagcgc cgcagcacca actacacagg caccgtaatc | 1140 |
| aacgacctgt agggcacccc cgctgccctg ccagagcgcc ccgcctttcc tcctccttct | 1200 |
| caccccacg ccgcgaataa aaaatgttcc atgtcaacga aa | 1242 |

<210> SEQ ID NO 11
<211> LENGTH: 3518
<212> TYPE: DNA
<213> ORGANISM: Herpes simplex virus 1

<400> SEQUENCE: 11

| | |
|---|---|
| tcgagcccgc cgaaacccgc cgcgtctgtt gaaatggcca gccgcccagc cgcatcctct | 60 |
| cccgtcgaag cgcgggcccc ggttggggga caggaggccg gcggcccag cgcagccacc | 120 |
| caggggagg ccgccgggc ccctctcgcc cacggccacc acgtgtactg ccagcgagtc | 180 |
| aatggcgtga tggtgctttc gacaagacg cccgggtccg cgtcctaccg catcagcgat | 240 |
| agcaactttg tccaatgtgg ttccaactgc accatgatca tcgacggaga cgtggtgcgc | 300 |
| gggcgccccc aggacccggg ggccgcggca tccccgctc ccttcgttgc ggtgacaaac | 360 |
| atcggagccg gcagcgacgg cggaccgcc gtcgtggcat tcggggaac ccacgtcgc | 420 |
| tcggcgggga cgtctaccgg tacccagacg gccgacgtcc ccaccgaggc ccttgggggc | 480 |

-continued

| | |
|---|---|
| cccctcctc ctccccgctt cacccgtggt ggcggctgtt gttcctgtcg cgacacacgg | 540 |
| cgccgctctg cggtattcgg gggggagggg gatccagtcg gccccgcgga gttcgtctcg | 600 |
| gacgaccggt cgtccgattc cgactcggat gactcggagg acacggactc ggagacgctg | 660 |
| tcacacgcct cctcggacgt gtccggcggg gccacgtacg acgacgccct tgactccgat | 720 |
| tcgtcatcgg atgactccct gcagatagat ggccccgtgt gtcgcccgtg gagcaatgac | 780 |
| accgcgcccc tggatgtttg ccccgggacc cccggcccgg gcgccgacgc cggtggtccc | 840 |
| tcagcggtag acccacacgc gccgacgcca gaggccggcc tggtcttgc ggccgatccc | 900 |
| gccgtggccc gggaagacgc ggaggggctt tcggaccccc ggccacgtct gggaacgggc | 960 |
| acggcctacc ccgtcccct ggaactcacg cccgagaacg cggaggccgt ggcgcgcttt | 1020 |
| ctgggagatg ccgtgaaccg cgaacccgcg ctcatgctgg agtacttttg ccggtgcgcc | 1080 |
| cgcgaggaaa ccaagcgtgt cccccccagg acattcggca gccccctcg cctcacggag | 1140 |
| gacgactttg ggcttctcaa ctacgcgctc gtggagatgc agcgcctgtg tctggacgtt | 1200 |
| cctccggtcc cgccgaacgc atacatgccc tattatctca gggagtatgt gacgcggctg | 1260 |
| gtcaacgggt tcaagccgct ggtgagccgg tccgctcgcc tttaccgcat cctgggggtt | 1320 |
| ctggtgcacc tgcggatccg gacccgggag gcctccttg aggagtggct gcgatccaag | 1380 |
| gaagtggccc tggattttgg cctgacgaa aggcttcgcg agcacgaagc ccagctggtg | 1440 |
| atcctggccc aggctctgga ccattacgac tgtctgatcc acagcacacc gcacacgctg | 1500 |
| gtcgagcggg ggctgcaatc ggccctgaag tatgaggagt tttacctaaa gcgttttggc | 1560 |
| gggcactaca tggagtccgt cttccagatg tacacccgca tcgccggctt tttggcctgc | 1620 |
| cgggccacgc gcggcatgcg ccacatcgcc ctggggcgag aggggtcgtg gtgggaaatg | 1680 |
| ttcaagttct ttttccaccg cctctacgac caccagatcg taccgtcgac ccccgccatg | 1740 |
| ctgaacctgg ggaccgcaa ctactacacc tccagctgct acctggtaaa cccccaggcc | 1800 |
| accacaaaca aggcgaccct gcgggccatc accagcaacg tcagtgccat cctcgcccgc | 1860 |
| aacgggggca tcgggctatg cgtgcaggcg tttaacgact ccggcccgg gaccgccagc | 1920 |
| gtcatgcccg ccctcaaggt ccttgactcg ctggtggcgg cgcacaacaa agagagcgcg | 1980 |
| cgtccgaccg gcgcgtgcgt gtacctggag ccgtggcaca ccgacgtgcg ggccgtgctc | 2040 |
| cggatgaagg gggtcctcgc cggcgaagag gcccagcgct gcgacaatat cttcagcgcc | 2100 |
| ctctggatgc cagacctgtt tttcaagcgc ctgattcgcc acctggacgg cgagaagaac | 2160 |
| gtcacatgga ccctgttcga ccgggacacc agcatgtcgc tcgccgactt tcacggggag | 2220 |
| gagttcgaga agctctacca gcacctcgag gtcatggggt tcggcgagca gatacccatc | 2280 |
| caggagctgg cctatggcat tgtgcgcagt gcggccacga ccgggagccc cttcgtcatg | 2340 |
| ttcaaagacg cggtgaaccg ccactacatc tacgacaccc agggggcggc catcgccggc | 2400 |
| tccaacctct gcaccgagat cgtccatccg gcctccaagc gatccagtgg ggtctgcaac | 2460 |
| ctggaagcg tgaatctggc ccgatgcgtc tccaggcaga cgtttgactt tgggcggctc | 2520 |
| cgcgacgccg tgcaggcgtg cgtgctgatg gtgaacatca tgatcgacag cacgctacaa | 2580 |
| cccacgcccc agtgcacccg cggcaacgac aacctgcggt ccatgggaat cggcatgcag | 2640 |
| ggcctgcaca cggcctgcct gaagctgggg ctggatctga gtctgccga atttcaggac | 2700 |
| ctgaacaaac acatcgccga ggtgatgctg ctgtcggcga tgaagaccag caacgcgctg | 2760 |
| tgcgttcgcg gggcccgtcc cttcaaccac tttaagcgca gcatgtatcg cgccggccgc | 2820 |
| tttcactggg agcgctttcc ggacgcccgg ccgcggtacg agggcgagtg ggagatgcta | 2880 |

-continued

```
cgccagagca tgatgaaaca cggcctgcgc aacagccagt tgtcgcgct gatgcccacc    2940 gccgcctcgg cgcagatctc ggacgtcagc gagggctttg ccccctgtt caccaacctg    3000 ttcagcaagg tgacccggga cggcgagacg ctgcgcccca acacgctcct gctaaaggaa    3060
ctggaacgca cgtttagcgg gaagcgcctc ctggaggtga tggacagtct cgacgccaag    3120
cagtggtccg tgccgcaggc gctcccgtgc ctggagccca ccaccccct ccggcgattc    3180 aagaccgcgt ttgactacga ccagaagttg ctgatcgacc tgtgtgcgga ccgcgccccc    3240
tacgtcgacc atagccaatc catgaccctg tatgtcacgg agaaggcgga cgggaccctc    3300
ccagcctcca ccctggtccg ccttctggtc cacgcatata agcgcggact aaaaacaggg    3360
atgtactact gcaaggttcg caaggcgacc aacagcgggg tctttggcgg cgacgacaac    3420
attgtctgca tgagctgcgc gctgtgaccg acaaaccccc tccgcgccag gcccgccgcc    3480
actgtcgtcg ccgtcccaag ctctcccctg ctgccatg                            3518
```

<210> SEQ ID NO 12
<211> LENGTH: 5956
<212> TYPE: DNA
<213> ORGANISM: Herpes simplex virus 2

<400> SEQUENCE: 12

```
gtgtgtttgg cgtgtgtctc tgaaatggcg gaaacccaca tgcaaatggg attcatggac     60
acgttacacc cccctgactc aggagatagg catatcctcc ttagattgac tcagcacacg    120
atcgcacccc acccctgtgt gccggggata aagccaacg cgcgcggtct gggttaccac    180
aacaggtggg tgcttcgggg acttgacggt cgccactctc ctgcgagccc tcacgtcttc    240
gcccaccgat tcctgttgcg ttcctgtcgg ccggtgctgt cctgtcgaca gattgttggc    300
gactgcccgg gtgattcgtc ggccggtgcg tcctttcggt cgtaccgccc accccgcctc    360
ccacgggccc gccgctgttt ccgttcatcg cgtccgagcc accgtcacct tggttccaat    420
ggccaaccgc cctgccgcat ccgccctcgc cggagcgcgg tctccgtccg aacgacagga    480
accccgggag cccgaggtcg cccccctgg cggcgaccac gtgttttgca ggaaagtcag    540
cggcgtgatg gtgcttttcca gcgatccccc cggccccgcg gcctaccgca ttagcgacag    600
cagctttgtt caatgcggct ccaactgcag tatgataatc gacggagacg tggcgcgcgg    660
tcatttgcgt gacctcgagg gcgctacgtc caccggcgcc ttcgtcgcga tctcaaacgt    720
cgcagccggc ggggatggcc gaaccgccgt cgtggcgctc ggcggaacct cgggcccgtc    780
cgcgactaca tccgtgggga cccagacgtc cggggagttc ctccacggga acccaaggac    840
ccccgaaccc caaggacccc aggctgtccc ccgccccct cctccccct ttccatgggg    900 ccacgagtgc tgcgcccgtc gcgatgccag gggcggcgcc gagaaggacg tcggggccgc    960
ggagtcatgg tcagacggcc cgtcgtccga ctccgaaacg gaggactcgg actcctcgga   1020
cgaggatacg ggctcgggtt cggagacgct gtctcgatcc tcttcgatct gggccgcagg   1080
ggcgactgac gacgatgaca cgactccga ctcgcggtcg acgactccg tgcagcccga   1140 cgttgtcgtt cgtcgcagat ggagcgacgg ccctgccccc gtggccttc ccaagccccg   1200 gcgcccggc gactcccccg gaaacccgg cctgggcgcc ggcaccgggc cgggctccgc   1260
gacggacccg cgcgcgtcgg ccgactccga ttccgcggcc cacgccgccg cacccccaggc   1320 ggacgtggcg ccggttctgg acagccagcc cactgtggga acggacccg gctacccagt   1380 cccccctagaa ctcacgcccg agaacgcgga ggcggtggcg cggtttctgg gggacgccgt   1440
```

-continued

```
cgaccgcgag cccgcgctca tgctggagta cttctgtcgg tgcgcccgcg aggagagcaa    1500
gcgcgtgccc ccacgaacct tcggcagcgc ccccgcctc acggaggacg actttgggct     1560
cctgaactac gcgctcgctg agatgcgacg cctgtgcctg gaccttcccc cggtcccccc    1620
caacgcatac acgccctatc atctgaggga gtatgcgacg cggctggtta acgggttcaa    1680
accccctggtg cggcggtccg cccgcctgta tcgcatcctg gggattctgg ttcacctgcg   1740
catccgtacc cgggaggcct cctttgagga atggatgcgc tccaaggagg tggacctgga    1800
cttcgggctg acgaaaaggc ttcgcgaaca cgaggcccag ctaatgatcc tggcccaggc    1860
cctgaacccc tacgactgtc tgatccacag caccccgaac acgctcgtcg agcgggggct    1920
gcagtcggcg ctgaagtacg aagagtttta cctcaagcgc ttcggcgggc actacatgga    1980
gtccgtcttc cagatgtaca cccgcatcgc cgggttcctg gcgtgccggg cgacccgcgg    2040
catgcgccac atcgcctgg ggcgacaggg gtcgtggtgg gaaatgttca agttcttttt     2100
ccaccgcctc tacgaccacc agatcgtgcc gtccacccc gccatgctga acctcggaac    2160
ccgcaactac tacacgtcca gctgatacct ggtaaacccc caggccacca ctaaccaggc    2220
caccctccgg gccatcaccg gcaacgtgag cgccatcctc gcccgcaacg ggggcatcgg    2280
gctgtgcatg caggcgttca acgacgccag ccccggcacc gccagcatca tgccggccct    2340
gaaggtcctg gactccctgg tggcggcgca caacaaacag agcacgcgcc ccaccggggc    2400
gtgcgtgtac ctggaaccct ggcacagcga cgttcgggcc gtgctcagaa tgaagggcgt    2460
cctcgccgg gaggaggccc agcgctgcga caacatcttc agcgccctct ggatgccgga    2520
cctgttcttc aagcgcctga tccgccacct cgacggcgag aaaaacgtca cctggtccct    2580
gttcgaccgg gacaccagca tgtcgctcgc cgactttcac ggcgaggagt tcgagaagct    2640
gtacgagcac ctcgaggcca tggggttcgg cgaaacgatc cccatccagg acctggcgta    2700
cgccatcgtg cgcagcgcgg ccaccaccgg aagccccttc atcatgttta aggacgcggt    2760
aaacagccac tacatctacg acacgcaagg ggcggccatt gccggctcca acctctgcac    2820
ggagatcgtc caccgtcct ccaaacgctc agcggggtc tgcaacctgg gcagcgtgaa     2880
tctggcccga tgcgtctccc ggcggacgtt cgattttggc atgctccgcg acgccgtgca    2940
ggcgtgcgtg ctaatggtta atatcatgat agacagcacg ctgcagccga cgccccagtg    3000
cgcccgcggc cacgacaacc tgcggtccat gggcattggc atgcagggcc tgcacacggc    3060
gtgcctgaag atgggcctgg atctggagtc ggccgagttc cgggacctga acacacacat    3120
cgccgaggtg atgctgctcg cggccatgaa gaccagtaac gcgctgtgcg ttcgcggggc    3180
gcgtcccttc agccactta agcgcagcat gtaccgggcc ggccgctttc actgggagcg    3240
cttttcgaac gccagcccgc ggtacgaggg cgagtgggag atgctacgcc agagcatgat    3300
gaaacacggc ctgcgcaaca gccagttcat cgcgctcatg cccaccgccg cctcggccca    3360
gatctcggac gtcagccagg gctttgcccc cctgttcacc aacctgttca gcaaggtgac    3420
cagggacggc gagacgctgc gccccaacac gctcttgctg aaggaactcg agcgcacgtt    3480
cggcgggaag cggctcctgg acgcgatgga cgggctcgag gccaagcagt ggtctgtggc    3540
ccaggccctg ccttgcctgg accccgccca cccctccgg cggttcaaga cggccttcga    3600
ctacgaccag gaactgctga tcgacctgtg tgcagaccgc gcccctatg ttgatcacag    3660
ccaatccatg actctgtatg tcacagagaa ggcggacggg acgctccccg cctccaccct    3720
ggtccgcctt ctcgtccacg catataagcg cggcctgaag acggggatgt actactgcaa    3780
ggttcgcaag gcgaccaaca gcggggtgtt cgccggcgac gacaacatcg tctgcacaag    3840
```

```
ctgcgcgctg taagcaacag cgctccgatc ggggtcaggc gtcgctctcg gtcccgcata    3900
tcgccatgga tcccgccgtc tcccccgcga gcaccgaccc cctagatacc cacgcgtcgg    3960
gggccggggc ggccccgatt ccggtgtgcc ccaccccga  gcggtacttc tacacctccc    4020
agtgccccga catcaaccac cttcgctccc tcagcatcct gaaccgctgg ctggagaccg    4080
agctcgtgtt cgtcgggac  gaggaggacg tctccaagct ctccgagggc gagctcggct    4140
tctaccgctt tctgtttgcc ttcctgtcgg ccgcggacga cctggtgacg gaaaacctgg    4200
gcggcctctc cggcctcttc gaacagaagg acattcttca ctactacgtg gagcaggaat    4260
gcatcgaggt cgtccactcc cgcgtctaca acatcatcca gctggtgctc tttcacaaca    4320
acgaccaggc gcgccgcgcc tatgtggccc gcaccatcaa ccacccggcc attcgcgtca    4380
aggtggactg gctggaggcg cgggtgcggg aatgcgactc gatcccggag aagttcatcc    4440
tcatgatcct catcgagggc gtcttttttg ccgcctcgtt cgccgccatc gcgtacctgc    4500
gcaccaacaa cctcctgcgg gtcacctgcc agtcgaacga cctcatcagc cgccacgagg    4560
ccgtgcatac gacagcctcg tgctacatct acaacaacta cctcggggc  cacgccaagc    4620 ccgaggcggc gcgcgtgtac cggctgtttc gggaggcggt ggatatcgag atcgggttca    4680
tccgatccca ggccccgacg gacagctcta tcctgagtcc gggggccctg gcggccatcg    4740
agaactacgt gcgattcagc gcggatcgcc tgctgggcct gatccatatg cagcccctgt    4800
attccgcccc cgccccgac  gccagctttc ccctcagcct catgtccacc gacaaacaca    4860
ccaacttctt cgagtgccgc agcacctcgt acgccgggc  cgtcgtcaac gatctgtgag    4920
ggtctgggcg cccttgtagc gatgtctaac cgaaataaag gggtcgaaac ggactgttgg    4980
gtctccggtg tgattattac gcaggggagg ggggtggcgg ctggggaaag ggaaggaacg    5040
cccgaaacca gagaaaagga ccaaaaggga acgcgtcca  accgataaat caagcgccga    5100
ccagaacccc gagatgcata ataacaaacg attttattac tcttattatt aacaggtcgg    5160
gcatcgggag gggatggggg cgcgcgtttc ctccgttccg gctactcgtc ccagaattta    5220
gccaggacgt ccttgtaaaa cgcgggcggg ggcgcgtggg cccacacctg cgccagaaac    5280
cggtcggcga tgtccgggc  ggtgatatga cgagtcacga tggagcgcgc taaatcttcg    5340
tcgcggaggt cctgatagat gggcagtctt tttagaagag tccagggtcc ccgctccttg    5400
gggctgataa gcgatatgac gtacttgacg tatctgtgct ccaccagctc ggcgatggtc    5460
atcggatcgg gcagccagtc cagggcctcc ggggcgtcgt ggatgacgtg gcggcgacgt    5520
ccggcgacat agccgcggtg ttccgcgacc cgctgcgcgt tggggacctg cacgagctcg    5580
ggcggggtga gtatctccga ggaggacgac cgggcgccgt cgcgcggccc accggcgacg    5640
tccgggggct ggagggggg  gtcttcttcg tagtcgtcct cgcccgcgat ctgttgggcc    5700
agaatttcgg tccacgagat gcgcgtctcg aggccgaccg gggccgcggt cagcgtaggc    5760
atgctctcca gggagcgcga gttggcgcgc tcccgccggg ccgccggcg  ggcctgggat    5820 cggctcgggg cggtccagtg acactcgcgc agcacgtcct cgacgacgc  gtaggtgtta    5880 ttggggtgca ggtctgtgtg gcagcggacg aacagcgcca ggaactgcgg gtaactcatc    5940
ttgaagtacc ctgcag                                                   5956
```

<210> SEQ ID NO 13
<211> LENGTH: 3678
<212> TYPE: DNA
<213> ORGANISM: Equine herpesvirus 4

```
<400> SEQUENCE: 13
aaaccactgt tctttacact ttatgctcta gttttggta  atagtgtctt ggaacacttt      60
taccctaaac gaaattatgg ctttggattt tttgagcacc gactgtccac tgggattgt     120
ttccgatatt atatccaacg tgaataccat caaagagtat ggatattcca gcgaattatc    180
aacaacgctg gcacctcgcc cgtctcgaga acaggtgtta gagtatatca ccagagtcgt    240
ggataaactc aagccgctgt gcagagtcga cgaacgcctt tacattgcgt gcggggagct    300
tgtacaccta cgaattaaag cacgcaacac agacctgaaa tattggctaa aatcgtctga    360
gattgatctt agcgatgtcg tggaacaggc catattggaa cacattgact tgttcagaa    420
aaccctcaac tcgtttgaaa catcggaata ccgagatttg tgttcattag gcctgcaatc    480
tgcgctaaag tatgaagaaa tgtatttagc caaaatgcga ggcggacgtc tagagtccat    540
ggggcaattt tttcttagac ttgcaactac tgctacgcac tatactatgg aacaaccagc    600
aatggctcgc gtgttggtta cggtgaggt  tggctggaca tatattttca gagccttttt    660
tactgcgcta ccggacagg  ttgtcattcc ggccacgcca attatgctgt ttggtgggag    720
agactgtggg tctatggcca gctgttattt gctaaacccc agggtaacag atatgaactc    780
tgcaattccg gctcttatgg aagaggttgg acccattttg tgcaaccgag gaggaattgg    840
actgtcttta cagaggttta acactccacc cacagaaggt tgttcacggg gtgtcatggc    900
tctcctaaag ctactagact ctatgaccat ggccattaac agcgacggtg aaagaccaac    960
aggagtgtgt gttatttcg  aaccctggca cgcagacatc cgcgccattt taaatatgcg   1020
cggaatgctg gccagagacg aaactgtgcg ctgcgacaac atctttgctt gtatgtggac   1080
cccagacctg ttttttgacc gctatcaacg gtacgtcgat ggagaaagcg gcataatgtg   1140
gactctgttt gatgatactg catcgcacct ctgccatatg tacggaaatg atttcacacg   1200
ggaatatgag cgcctggagc ggtgtggatt tgggatagac gctattccca tacaggacat   1260
ggcctttatc atagttagaa gtgctgtaat gacaggaagc ccattttttga tgtttaaaga   1320
cgcgtgcaac aggcactacc actttgacat gcggcagaga ggtgcgataa tggggtctaa   1380
tctatgcaca gaaattatcc agcatgccga cgaaacccaa acggggtgtg gtaatctagc   1440
cagcatcaac ctcccaaaat gtctagccct tccacctcca aatattgcag gtgtgccata   1500
ttttgacttc gccgctctgg ccgcgctgc  cgcaactgcc acaattttttg tcaatgcgat   1560
gatgtgtgcc agcacatatc caactgttaa atcccagaaa ggcgttgaag aaaaccggtc   1620
gctgggactt ggaattcagg ggctacatac cacgttttttg atgctggacc tggatatggc   1680
atctccagag gcgcaccaac taaacaagca aatagcagaa aggctgttat tgaactctat   1740
gaaggccagc gcaacgctct gcaagctggg tatgcaaccc tttaaagggt ttgaagacag   1800
caagtacagt cggggggaac tacccttttga tgcctaccca aatgtaacac taacaaaccg   1860
caacgcctgg cgtagacttc gcactgacat aaaacaatac ggcttgtaca attctcagtt   1920
tgtagcctat atgccaacag tatcttcgtc acaggttacc gagagcagcg aggggttttc   1980
tcctgtttac acaaacctgt ttagcaaagt tactgctacc ggggaagtac tcaggcccaa   2040
tgtactgcta atgcgcacca tcagaagtat ttttccacag gaatgcgcgc gcttacaagc   2100
gctatctacg ctagaagctg cgaaatggtc agttgtggga gcgtttggtg atttgccagt   2160
tggtcacccc ctcagtaagt ttaaaacagc atttgagtac gaccagacta tgctaattaa   2220
catgtgtgct gacagggctg cgtttgtgga ccagagccaa tccatgtctt tgtttataac   2280
tgagcctgct gacggaaaac tccccgcctc cagaattatg aatcttttgg tccacgcata   2340
```

-continued

```
taaacgcgga cttaaaacag gcatgtacta ctgcaaaatc aagaaggcaa caaacaacgg    2400
agtctttgtt ggcggagacc tagtctgcac cagctgcagc ttgtagggca gcctcgccat    2460
tttgcccagg gcgggaaaat aattatggcc ctcgaaaact ctaaaaaaac agattttgct    2520
gacgagttat tgataaatgc gtatttctat acgccggaat gtcccgatat tgaacaccta    2580
cgcttgttga gcgttgccaa ccgctggctg gatacggacc ttccaatttc tgatgacctc    2640
aaggacgttg ctaaactcgc gccagccgag cgagagtttt accggttttt gtttgccttt    2700
ttatctgctg ctgacgactt ggtaaattta aacctgggag atttatccgc actatttact    2760
caaaaggaca ttcttcacta ctacattgag caagagtcta ttgaagtaac gcactccaga    2820
gtatatagcg ctatacagct tatgttgttt ggaaacgacg caacagcgcg cgctaggtat    2880
gtcgcatctg ttgtcaaaga cgtggccata gacctaaagg tatcttggtt gcaagcaaag    2940
gtgcgagaat gcaaatctgt ggcggaaaag tatattttga tgatattaat agagggcgtt    3000
ttcttcgcgt cgtcctttcc gtccatcgca tatcttcgca cccacaatct ctttgtggta    3060
acctgtcaaa gtaatgattt aattagccgc gacgaagcaa ttcacaccaa cgcctcgtgc    3120
tgtatctaca acaactacct tgggcgtttt gaaaagccag ctccaacgag gatttatgcg    3180
ctgttttctg aggccgtaaa catcgagtgt gaattttgc tttcccatgc ccccaaaagc    3240
agccacctgt tggacattga agccatcata tgctacgtac gctatagcgc ggacaggctt    3300
ttgggggaaa ttggactatc tccgctgttt aatgctccca acccccacc aagcttcccc    3360 ctagctttca tgactgtgga aaaacatacc aacttttttg aaaggcgaag caccgcatac    3420
tcgggaactc ttataaacga tctgtaatgt aaaaataaaa actaattttg attcacttat    3480
ttgtcttgtt tgcgtgttgg atgtacgcga tttaaaaaaa tactgagaaa agatactccc    3540
gatttaactt tatttaagac cattgtcttc ggtgtccaca gtcatcccag tagttaacca    3600
acacagtgtt gtaatcagtg ggggtgggaa tgtggttcca aaacatatta gcaagctctc    3660
tgacaatttc gtgttcgg                                                  3678
```

<210> SEQ ID NO 14
<211> LENGTH: 20
<212> TYPE: DNA
<213> ORGANISM: Escherichia coli

<400> SEQUENCE: 14

```
ccgtcgcgct ttgtcaccag                                                  20
```

<210> SEQ ID NO 15
<211> LENGTH: 20
<212> TYPE: DNA
<213> ORGANISM: Escherichia coli

<400> SEQUENCE: 15

```
ctgtgctacc gtcgcgcttt                                                  20
```

<210> SEQ ID NO 16
<211> LENGTH: 20
<212> TYPE: DNA
<213> ORGANISM: Escherichia coli

<400> SEQUENCE: 16

```
tgatgcgctc tgtgctaccg                                                  20
```

<210> SEQ ID NO 17

<211> LENGTH: 20
<212> TYPE: DNA
<213> ORGANISM: Escherichia coli

<400> SEQUENCE: 17
tttgtcgaga ttgatgcgct                                              20

<210> SEQ ID NO 18
<211> LENGTH: 20
<212> TYPE: DNA
<213> ORGANISM: Escherichia coli

<400> SEQUENCE: 18
agaacgcgat ggattttgtc                                              20

<210> SEQ ID NO 19
<211> LENGTH: 20
<212> TYPE: DNA
<213> ORGANISM: Escherichia coli

<400> SEQUENCE: 19
tgccgcccaa tccagaacgc                                              20

<210> SEQ ID NO 20
<211> LENGTH: 20
<212> TYPE: DNA
<213> ORGANISM: Escherichia coli

<400> SEQUENCE: 20
agtccttctg ccgcccaatc                                              20

<210> SEQ ID NO 21
<211> LENGTH: 20
<212> TYPE: DNA
<213> ORGANISM: Escherichia coli

<400> SEQUENCE: 21
aaactgaatg tgggagcgca                                              20

<210> SEQ ID NO 22
<211> LENGTH: 20
<212> TYPE: DNA
<213> ORGANISM: Escherichia coli

<400> SEQUENCE: 22
ataatggttt cgtggatgtc                                              20

<210> SEQ ID NO 23
<211> LENGTH: 20
<212> TYPE: DNA
<213> ORGANISM: Escherichia coli

<400> SEQUENCE: 23
cggcagcctt gataatggtt                                              20

<210> SEQ ID NO 24
<211> LENGTH: 20
<212> TYPE: DNA
<213> ORGANISM: Escherichia coli

<400> SEQUENCE: 24
atactgataa tccggcgcat                                              20

-continued

```
<210> SEQ ID NO 25
<211> LENGTH: 20
<212> TYPE: DNA
<213> ORGANISM: Escherichia coli

<400> SEQUENCE: 25
tacgcaggtg gaagatcgcc                                                   20

<210> SEQ ID NO 26
<211> LENGTH: 20
<212> TYPE: DNA
<213> ORGANISM: Escherichia coli

<400> SEQUENCE: 26
ggtcgtacag cgcaggcggc                                                   20

<210> SEQ ID NO 27
<211> LENGTH: 20
<212> TYPE: DNA
<213> ORGANISM: Escherichia coli

<400> SEQUENCE: 27
gcccatctcg accattttca                                                   20

<210> SEQ ID NO 28
<211> LENGTH: 20
<212> TYPE: DNA
<213> ORGANISM: Escherichia coli

<400> SEQUENCE: 28
tatcgtattt gcccatctcg                                                   20

<210> SEQ ID NO 29
<211> LENGTH: 20
<212> TYPE: DNA
<213> ORGANISM: Escherichia coli

<400> SEQUENCE: 29
cggcagcata agagaaggtc                                                   20

<210> SEQ ID NO 30
<211> LENGTH: 20
<212> TYPE: DNA
<213> ORGANISM: Escherichia coli

<400> SEQUENCE: 30
ccttccagct gcttaacggc                                                   20

<210> SEQ ID NO 31
<211> LENGTH: 20
<212> TYPE: DNA
<213> ORGANISM: Escherichia coli

<400> SEQUENCE: 31
ccagatattt gccttccagc                                                   20

<210> SEQ ID NO 32
<211> LENGTH: 20
<212> TYPE: DNA
<213> ORGANISM: Escherichia coli

<400> SEQUENCE: 32
atagatttcg ccggtcacgc                                                   20
```

<210> SEQ ID NO 33
<211> LENGTH: 20
<212> TYPE: DNA
<213> ORGANISM: Escherichia coli

<400> SEQUENCE: 33
ggaactgggc gctctcatag                                               20

<210> SEQ ID NO 34
<211> LENGTH: 20
<212> TYPE: DNA
<213> ORGANISM: Escherichia coli

<400> SEQUENCE: 34
gaatataaag gaactgggcg                                               20

<210> SEQ ID NO 35
<211> LENGTH: 20
<212> TYPE: DNA
<213> ORGANISM: Escherichia coli

<400> SEQUENCE: 35
gcacgcggca actagaatat                                               20

<210> SEQ ID NO 36
<211> LENGTH: 20
<212> TYPE: DNA
<213> ORGANISM: Escherichia coli

<400> SEQUENCE: 36
ttcgagaaca agcacgcggc                                               20

<210> SEQ ID NO 37
<211> LENGTH: 20
<212> TYPE: DNA
<213> ORGANISM: Escherichia coli

<400> SEQUENCE: 37
tttcacgcgg gtagttcgag                                               20

<210> SEQ ID NO 38
<211> LENGTH: 20
<212> TYPE: DNA
<213> ORGANISM: Escherichia coli

<400> SEQUENCE: 38
acgcttcaca tattgcaggc                                               20

<210> SEQ ID NO 39
<211> LENGTH: 20
<212> TYPE: DNA
<213> ORGANISM: Escherichia coli

<400> SEQUENCE: 39
ggaaaccgcg tcgtaaaaac                                               20

<210> SEQ ID NO 40
<211> LENGTH: 20
<212> TYPE: DNA
<213> ORGANISM: Escherichia coli

<400> SEQUENCE: 40
ttaaatgtgg aaaccgcgtc                                               20

<210> SEQ ID NO 41
<211> LENGTH: 20
<212> TYPE: DNA
<213> ORGANISM: Escherichia coli

<400> SEQUENCE: 41
catgattggc gtcggcagcg                                          20

<210> SEQ ID NO 42
<211> LENGTH: 20
<212> TYPE: DNA
<213> ORGANISM: Escherichia coli

<400> SEQUENCE: 42
cgcacgccgg acatgattgg                                          20

<210> SEQ ID NO 43
<211> LENGTH: 20
<212> TYPE: DNA
<213> ORGANISM: Escherichia coli

<400> SEQUENCE: 43
cgagtcgggg tacgcacgcc                                          20

<210> SEQ ID NO 44
<211> LENGTH: 20
<212> TYPE: DNA
<213> ORGANISM: Escherichia coli

<400> SEQUENCE: 44
tcgatcagta cgcaggagct                                          20

<210> SEQ ID NO 45
<211> LENGTH: 20
<212> TYPE: DNA
<213> ORGANISM: Escherichia coli

<400> SEQUENCE: 45
gctgtcaccg cactcgatca                                          20

<210> SEQ ID NO 46
<211> LENGTH: 20
<212> TYPE: DNA
<213> ORGANISM: Escherichia coli

<400> SEQUENCE: 46
ggaatccagg ctgtcaccgc                                          20

<210> SEQ ID NO 47
<211> LENGTH: 20
<212> TYPE: DNA
<213> ORGANISM: Escherichia coli

<400> SEQUENCE: 47
ggaggtggcg ttgatggaat                                          20

<210> SEQ ID NO 48
<211> LENGTH: 20
<212> TYPE: DNA
<213> ORGANISM: Escherichia coli

<400> SEQUENCE: 48
aacaatcgcg ctggaggtgg                                                  20

<210> SEQ ID NO 49
<211> LENGTH: 20
<212> TYPE: DNA
<213> ORGANISM: Escherichia coli

<400> SEQUENCE: 49
ctacccagcg cacgaatacg                                                  20

<210> SEQ ID NO 50
<211> LENGTH: 20
<212> TYPE: DNA
<213> ORGANISM: Escherichia coli

<400> SEQUENCE: 50
atgcagccgg tatggaacgc                                                  20

<210> SEQ ID NO 51
<211> LENGTH: 20
<212> TYPE: DNA
<213> ORGANISM: Escherichia coli

<400> SEQUENCE: 51
ttgtagaacg gaatgcagcc                                                  20

<210> SEQ ID NO 52
<211> LENGTH: 20
<212> TYPE: DNA
<213> ORGANISM: Escherichia coli

<400> SEQUENCE: 52
ccgctgtctg gaaatgtttg                                                  20

<210> SEQ ID NO 53
<211> LENGTH: 20
<212> TYPE: DNA
<213> ORGANISM: Escherichia coli

<400> SEQUENCE: 53
aggatttcac cgctgtctgg                                                  20

<210> SEQ ID NO 54
<211> LENGTH: 20
<212> TYPE: DNA
<213> ORGANISM: Escherichia coli

<400> SEQUENCE: 54
cgcacaccgc cctgagagca                                                  20

<210> SEQ ID NO 55
<211> LENGTH: 20
<212> TYPE: DNA
<213> ORGANISM: Escherichia coli

<400> SEQUENCE: 55
cacatcgggt agaacagcgt                                                  20

<210> SEQ ID NO 56
<211> LENGTH: 20
<212> TYPE: DNA
<213> ORGANISM: Escherichia coli

<400> SEQUENCE: 56
ctttccactt ccagatgcca                                               20

<210> SEQ ID NO 57
<211> LENGTH: 20
<212> TYPE: DNA
<213> ORGANISM: Escherichia coli

<400> SEQUENCE: 57
ttgccttcca caccacggtt                                               20

<210> SEQ ID NO 58
<211> LENGTH: 20
<212> TYPE: DNA
<213> ORGANISM: Escherichia coli

<400> SEQUENCE: 58
cacgcggttg ccttccacac                                               20

<210> SEQ ID NO 59
<211> LENGTH: 20
<212> TYPE: DNA
<213> ORGANISM: Escherichia coli

<400> SEQUENCE: 59
ccatatgacg cacgcggttg                                               20

<210> SEQ ID NO 60
<211> LENGTH: 20
<212> TYPE: DNA
<213> ORGANISM: Escherichia coli

<400> SEQUENCE: 60
ttcacctttc agcagacggg                                               20

<210> SEQ ID NO 61
<211> LENGTH: 20
<212> TYPE: DNA
<213> ORGANISM: Escherichia coli

<400> SEQUENCE: 61
cgggctgaac agggtgatat                                               20

<210> SEQ ID NO 62
<211> LENGTH: 20
<212> TYPE: DNA
<213> ORGANISM: Escherichia coli

<400> SEQUENCE: 62
cggacgggct gaacagggtg                                               20

<210> SEQ ID NO 63
<211> LENGTH: 20
<212> TYPE: DNA
<213> ORGANISM: Escherichia coli

<400> SEQUENCE: 63
gtcggacggg ctgaacaggg                                               20

<210> SEQ ID NO 64
<211> LENGTH: 20
<212> TYPE: DNA
<213> ORGANISM: Escherichia coli -continued

```
<400> SEQUENCE: 64
aaactcttcc tgatcggcga                                                    20

<210> SEQ ID NO 65
<211> LENGTH: 20
<212> TYPE: DNA
<213> ORGANISM: Escherichia coli

<400> SEQUENCE: 65
gcggatgctg tcgtctttct                                                    20

<210> SEQ ID NO 66
<211> LENGTH: 20
<212> TYPE: DNA
<213> ORGANISM: Escherichia coli

<400> SEQUENCE: 66
gctgcttgcg gatgctgtcg                                                    20

<210> SEQ ID NO 67
<211> LENGTH: 20
<212> TYPE: DNA
<213> ORGANISM: Escherichia coli

<400> SEQUENCE: 67
ggctttcaca cgctgcttgc                                                    20

<210> SEQ ID NO 68
<211> LENGTH: 20
<212> TYPE: DNA
<213> ORGANISM: Escherichia coli

<400> SEQUENCE: 68
gctcaacggc tttcacacgc                                                    20

<210> SEQ ID NO 69
<211> LENGTH: 20
<212> TYPE: DNA
<213> ORGANISM: Escherichia coli

<400> SEQUENCE: 69
gaccggtaga cgcacgttcc                                                    20

<210> SEQ ID NO 70
<211> LENGTH: 20
<212> TYPE: DNA
<213> ORGANISM: Escherichia coli

<400> SEQUENCE: 70
gggctatggg tattgcagtg                                                    20

<210> SEQ ID NO 71
<211> LENGTH: 20
<212> TYPE: DNA
<213> ORGANISM: Escherichia coli

<400> SEQUENCE: 71
aaacgggcta tgggtattgc                                                    20

<210> SEQ ID NO 72
<211> LENGTH: 20
<212> TYPE: DNA
<213> ORGANISM: Escherichia coli
```

<400> SEQUENCE: 72
cggatcaaac gggctatggg                                               20

<210> SEQ ID NO 73
<211> LENGTH: 20
<212> TYPE: DNA
<213> ORGANISM: Escherichia coli

<400> SEQUENCE: 73
gggctatctc caggcacagg                                               20

<210> SEQ ID NO 74
<211> LENGTH: 20
<212> TYPE: DNA
<213> ORGANISM: Escherichia coli

<400> SEQUENCE: 74
ggcagggcta tctccaggca                                               20

<210> SEQ ID NO 75
<211> LENGTH: 20
<212> TYPE: DNA
<213> ORGANISM: Escherichia coli

<400> SEQUENCE: 75
tggtcggcag ggctatctcc                                               20

<210> SEQ ID NO 76
<211> LENGTH: 20
<212> TYPE: DNA
<213> ORGANISM: Escherichia coli

<400> SEQUENCE: 76
gcggtttggt cggcagggct                                               20

<210> SEQ ID NO 77
<211> LENGTH: 20
<212> TYPE: DNA
<213> ORGANISM: Escherichia coli

<400> SEQUENCE: 77
ttcagcggtt tggtcggcag                                               20

<210> SEQ ID NO 78
<211> LENGTH: 20
<212> TYPE: DNA
<213> ORGANISM: Escherichia coli

<400> SEQUENCE: 78
acgtcgttca gcggtttggt                                               20

<210> SEQ ID NO 79
<211> LENGTH: 20
<212> TYPE: DNA
<213> ORGANISM: Escherichia coli

<400> SEQUENCE: 79
tttcaccgtt ctcgtcgttg                                               20

<210> SEQ ID NO 80
<211> LENGTH: 20
<212> TYPE: DNA

<213> ORGANISM: Escherichia coli

<400> SEQUENCE: 80
cagcgcgatt tcaccgttct                                                20

<210> SEQ ID NO 81
<211> LENGTH: 20
<212> TYPE: DNA
<213> ORGANISM: Escherichia coli

<400> SEQUENCE: 81
cgtacacagc gcgatttcac                                                20

<210> SEQ ID NO 82
<211> LENGTH: 20
<212> TYPE: DNA
<213> ORGANISM: Escherichia coli

<400> SEQUENCE: 82
agcagacagc gtacacagcg                                                20

<210> SEQ ID NO 83
<211> LENGTH: 20
<212> TYPE: DNA
<213> ORGANISM: Escherichia coli

<400> SEQUENCE: 83
caggttgaaa gcagacagcg                                                20

<210> SEQ ID NO 84
<211> LENGTH: 20
<212> TYPE: DNA
<213> ORGANISM: Escherichia coli

<400> SEQUENCE: 84
aattgcgccc aggttgaaag                                                20

<210> SEQ ID NO 85
<211> LENGTH: 20
<212> TYPE: DNA
<213> ORGANISM: Escherichia coli

<400> SEQUENCE: 85
ccaggttatt aattgcgccc                                                20

<210> SEQ ID NO 86
<211> LENGTH: 20
<212> TYPE: DNA
<213> ORGANISM: Escherichia coli

<400> SEQUENCE: 86
ttgccagctc ttccagttca                                                20

<210> SEQ ID NO 87
<211> LENGTH: 20
<212> TYPE: DNA
<213> ORGANISM: Escherichia coli

<400> SEQUENCE: 87
accgccagaa ttgccagctc                                                20

<210> SEQ ID NO 88
<211> LENGTH: 20

```
<212> TYPE: DNA
<213> ORGANISM: Escherichia coli

<400> SEQUENCE: 88
gtcaagtgca cgaaccgcca                                              20

<210> SEQ ID NO 89
<211> LENGTH: 20
<212> TYPE: DNA
<213> ORGANISM: Escherichia coli

<400> SEQUENCE: 89
atccagcagc gcgtcaagtg                                              20

<210> SEQ ID NO 90
<211> LENGTH: 20
<212> TYPE: DNA
<213> ORGANISM: Escherichia coli

<400> SEQUENCE: 90
tgataatcca gcagcgcgtc                                              20

<210> SEQ ID NO 91
<211> LENGTH: 20
<212> TYPE: DNA
<213> ORGANISM: Escherichia coli

<400> SEQUENCE: 91
gatcacacca atacccagcg                                              20

<210> SEQ ID NO 92
<211> LENGTH: 20
<212> TYPE: DNA
<213> ORGANISM: Escherichia coli

<400> SEQUENCE: 92
tcgttcgcca ggtagtaagc                                              20

<210> SEQ ID NO 93
<211> LENGTH: 20
<212> TYPE: DNA
<213> ORGANISM: Escherichia coli

<400> SEQUENCE: 93
cgtttaccgt cgttcgccag                                              20

<210> SEQ ID NO 94
<211> LENGTH: 20
<212> TYPE: DNA
<213> ORGANISM: Escherichia coli

<400> SEQUENCE: 94
tgccgtcgga gtagcgttta                                              20

<210> SEQ ID NO 95
<211> LENGTH: 20
<212> TYPE: DNA
<213> ORGANISM: Escherichia coli

<400> SEQUENCE: 95
tatgcgtcag gttgttggcg                                              20

<210> SEQ ID NO 96
```

-continued

```
<211> LENGTH: 20
<212> TYPE: DNA
<213> ORGANISM: Escherichia coli

<400> SEQUENCE: 96
cgaaggtttt atgcgtcagg                                               20

<210> SEQ ID NO 97
<211> LENGTH: 20
<212> TYPE: DNA
<213> ORGANISM: Escherichia coli

<400> SEQUENCE: 97
gttaaaccac gggcacgcgc                                               20

<210> SEQ ID NO 98
<211> LENGTH: 20
<212> TYPE: DNA
<213> ORGANISM: Escherichia coli

<400> SEQUENCE: 98
ttcgcgtaag tggtttcgtt                                               20

<210> SEQ ID NO 99
<211> LENGTH: 20
<212> TYPE: DNA
<213> ORGANISM: Escherichia coli

<400> SEQUENCE: 99
tataggtatc gatcggcagg                                               20

<210> SEQ ID NO 100
<211> LENGTH: 20
<212> TYPE: DNA
<213> ORGANISM: Escherichia coli

<400> SEQUENCE: 100
cagtcgtaat gcagcggctc                                               20

<210> SEQ ID NO 101
<211> LENGTH: 20
<212> TYPE: DNA
<213> ORGANISM: Escherichia coli

<400> SEQUENCE: 101
cgcagagctt cccagtcgta                                               20

<210> SEQ ID NO 102
<211> LENGTH: 20
<212> TYPE: DNA
<213> ORGANISM: Escherichia coli

<400> SEQUENCE: 102
tcagagcaga aagcgtggag                                               20

<210> SEQ ID NO 103
<211> LENGTH: 20
<212> TYPE: DNA
<213> ORGANISM: Escherichia coli

<400> SEQUENCE: 103
tcggacggca tcagagcaga                                               20
```

-continued

```
<210> SEQ ID NO 104
<211> LENGTH: 20
<212> TYPE: DNA
<213> ORGANISM: Escherichia coli

<400> SEQUENCE: 104
ggcgttagag atctgcgaag                                                    20

<210> SEQ ID NO 105
<211> LENGTH: 20
<212> TYPE: DNA
<213> ORGANISM: Escherichia coli

<400> SEQUENCE: 105
tttgatgctg acgtaaccgc                                                    20

<210> SEQ ID NO 106
<211> LENGTH: 20
<212> TYPE: DNA
<213> ORGANISM: Escherichia coli

<400> SEQUENCE: 106
tcgacgcttt gatgctgacg                                                    20

<210> SEQ ID NO 107
<211> LENGTH: 20
<212> TYPE: DNA
<213> ORGANISM: Escherichia coli

<400> SEQUENCE: 107
cctggcgcaa aataccgtct                                                    20

<210> SEQ ID NO 108
<211> LENGTH: 20
<212> TYPE: DNA
<213> ORGANISM: Escherichia coli

<400> SEQUENCE: 108
tagtccggca ccacctggcg                                                    20

<210> SEQ ID NO 109
<211> LENGTH: 20
<212> TYPE: DNA
<213> ORGANISM: Escherichia coli

<400> SEQUENCE: 109
gcaggtgctc gtagtccggc                                                    20

<210> SEQ ID NO 110
<211> LENGTH: 20
<212> TYPE: DNA
<213> ORGANISM: Escherichia coli

<400> SEQUENCE: 110
cgtcgtgcag gtgctcgtag                                                    20

<210> SEQ ID NO 111
<211> LENGTH: 20
<212> TYPE: DNA
<213> ORGANISM: Escherichia coli

<400> SEQUENCE: 111
gctcataggc gtcgtgcagg                                                    20
```

<210> SEQ ID NO 112
<211> LENGTH: 20
<212> TYPE: DNA
<213> ORGANISM: Escherichia coli

<400> SEQUENCE: 112
cccacagcag ctcataggcg                                              20

<210> SEQ ID NO 113
<211> LENGTH: 20
<212> TYPE: DNA
<213> ORGANISM: Escherichia coli

<400> SEQUENCE: 113
cggcatttcc cacagcagct                                              20

<210> SEQ ID NO 114
<211> LENGTH: 20
<212> TYPE: DNA
<213> ORGANISM: Escherichia coli

<400> SEQUENCE: 114
catcgttacc cggcatttcc                                              20

<210> SEQ ID NO 115
<211> LENGTH: 20
<212> TYPE: DNA
<213> ORGANISM: Escherichia coli

<400> SEQUENCE: 115
ggatcgtagt tggtgttggc                                              20

<210> SEQ ID NO 116
<211> LENGTH: 20
<212> TYPE: DNA
<213> ORGANISM: Escherichia coli

<400> SEQUENCE: 116 tcggcactttt tcctgacggg                                             20

<210> SEQ ID NO 117
<211> LENGTH: 20
<212> TYPE: DNA
<213> ORGANISM: Escherichia coli

<400> SEQUENCE: 117
aggcggtgag caggtctttc                                              20

<210> SEQ ID NO 118
<211> LENGTH: 20
<212> TYPE: DNA
<213> ORGANISM: Escherichia coli

<400> SEQUENCE: 118
cgaatttgta ggcggtgagc                                              20

<210> SEQ ID NO 119
<211> LENGTH: 20
<212> TYPE: DNA
<213> ORGANISM: Escherichia coli

<400> SEQUENCE: 119
gtgttttgac cccgaatttg                                              20

<210> SEQ ID NO 120
<211> LENGTH: 20
<212> TYPE: DNA
<213> ORGANISM: Escherichia coli

<400> SEQUENCE: 120
cgtcttgtgc gtcttcagcg                                         20

<210> SEQ ID NO 121
<211> LENGTH: 20
<212> TYPE: DNA
<213> ORGANISM: Escherichia coli

<400> SEQUENCE: 121
tcttacatgc gccgctttcg                                         20

<210> SEQ ID NO 122
<211> LENGTH: 20
<212> TYPE: DNA
<213> ORGANISM: Escherichia coli

<400> SEQUENCE: 122
cggctgacca aagaacatcg                                         20

<210> SEQ ID NO 123
<211> LENGTH: 20
<212> TYPE: DNA
<213> ORGANISM: Escherichia coli

<400> SEQUENCE: 123
ccacgttgac cggctgacca                                         20

<210> SEQ ID NO 124
<211> LENGTH: 20
<212> TYPE: DNA
<213> ORGANISM: Escherichia coli

<400> SEQUENCE: 124
tagcgagcca cgttgaccgg                                         20

<210> SEQ ID NO 125
<211> LENGTH: 20
<212> TYPE: DNA
<213> ORGANISM: Escherichia coli

<400> SEQUENCE: 125
cggacgccag aagaaagaga                                         20

<210> SEQ ID NO 126
<211> LENGTH: 20
<212> TYPE: DNA
<213> ORGANISM: Escherichia coli

<400> SEQUENCE: 126
caacttcttc cggacgccag                                         20

<210> SEQ ID NO 127
<211> LENGTH: 20
<212> TYPE: DNA
<213> ORGANISM: Escherichia coli

<400> SEQUENCE: 127

-continued aatctatacg gtcgcgggag					20

<210> SEQ ID NO 128
<211> LENGTH: 20
<212> TYPE: DNA
<213> ORGANISM: Escherichia coli

<400> SEQUENCE: 128
tgtgtttttc gtgctccggc					20

<210> SEQ ID NO 129
<211> LENGTH: 20
<212> TYPE: DNA
<213> ORGANISM: Escherichia coli

<400> SEQUENCE: 129
gcaatagcgc cacgttcggg					20

<210> SEQ ID NO 130
<211> LENGTH: 20
<212> TYPE: DNA
<213> ORGANISM: Escherichia coli

<400> SEQUENCE: 130
agaaataagc ggcaatagcg					20

<210> SEQ ID NO 131
<211> LENGTH: 20
<212> TYPE: DNA
<213> ORGANISM: Escherichia coli

<400> SEQUENCE: 131
cggaatagaa ataagcggca					20

<210> SEQ ID NO 132
<211> LENGTH: 20
<212> TYPE: DNA
<213> ORGANISM: Escherichia coli

<400> SEQUENCE: 132
acccaggttt ccagttccgg					20

<210> SEQ ID NO 133
<211> LENGTH: 20
<212> TYPE: DNA
<213> ORGANISM: Escherichia coli

<400> SEQUENCE: 133
ataggaacgg gaatgaatcg					20

<210> SEQ ID NO 134
<211> LENGTH: 20
<212> TYPE: DNA
<213> ORGANISM: Escherichia coli

<400> SEQUENCE: 134
tcccttccgc acgtttctgg					20

<210> SEQ ID NO 135
<211> LENGTH: 20
<212> TYPE: DNA
<213> ORGANISM: Escherichia coli

<400> SEQUENCE: 135
cgcccagcag atgccagtag                    20

<210> SEQ ID NO 136
<211> LENGTH: 20
<212> TYPE: DNA
<213> ORGANISM: Escherichia coli

<400> SEQUENCE: 136
gtaccttcgc ccagcagatg                    20

<210> SEQ ID NO 137
<211> LENGTH: 20
<212> TYPE: DNA
<213> ORGANISM: Escherichia coli

<400> SEQUENCE: 137
cgcaggctaa cggtcacagt                    20

<210> SEQ ID NO 138
<211> LENGTH: 20
<212> TYPE: DNA
<213> ORGANISM: Escherichia coli

<400> SEQUENCE: 138
tttcttcagc tcgcgcaggc                    20

<210> SEQ ID NO 139
<211> LENGTH: 20
<212> TYPE: DNA
<213> ORGANISM: Escherichia coli

<400> SEQUENCE: 139
gcaaatgcga aggaacaagc                    20

<210> SEQ ID NO 140
<211> LENGTH: 20
<212> TYPE: DNA
<213> ORGANISM: Escherichia coli

<400> SEQUENCE: 140
atcaattcgc gttctgcaaa                    20

<210> SEQ ID NO 141
<211> LENGTH: 20
<212> TYPE: DNA
<213> ORGANISM: Escherichia coli

<400> SEQUENCE: 141
gcgaataatt ttggcgttgc                    20

<210> SEQ ID NO 142
<211> LENGTH: 20
<212> TYPE: DNA
<213> ORGANISM: Escherichia coli

<400> SEQUENCE: 142
gcgggcaatc aggcgaataa                    20

<210> SEQ ID NO 143
<211> LENGTH: 20
<212> TYPE: DNA
<213> ORGANISM: Escherichia coli

<400> SEQUENCE: 143
cagggcttcg tcgcgggcaa                                         20

<210> SEQ ID NO 144
<211> LENGTH: 20
<212> TYPE: DNA
<213> ORGANISM: Escherichia coli

<400> SEQUENCE: 144
cggtcaggtg cagggcttcg                                         20

<210> SEQ ID NO 145
<211> LENGTH: 20
<212> TYPE: DNA
<213> ORGANISM: Escherichia coli

<400> SEQUENCE: 145
tgctgggtgc cggtcaggtg                                         20

<210> SEQ ID NO 146
<211> LENGTH: 20
<212> TYPE: DNA
<213> ORGANISM: Escherichia coli

<400> SEQUENCE: 146
catatgctgg gtgccggtca                                         20

<210> SEQ ID NO 147
<211> LENGTH: 20
<212> TYPE: DNA
<213> ORGANISM: Escherichia coli

<400> SEQUENCE: 147
gcaatttccg ccatctcagg                                         20

<210> SEQ ID NO 148
<211> LENGTH: 20
<212> TYPE: DNA
<213> ORGANISM: Escherichia coli

<400> SEQUENCE: 148
tcctgcttac actcttcggc                                         20

<210> SEQ ID NO 149
<211> LENGTH: 20
<212> TYPE: DNA
<213> ORGANISM: Escherichia coli

<400> SEQUENCE: 149
atccgcccag tctttctcct                                         20

<210> SEQ ID NO 150
<211> LENGTH: 20
<212> TYPE: DNA
<213> ORGANISM: Escherichia coli

<400> SEQUENCE: 150
gaacagataa tccgcccagt                                         20

<210> SEQ ID NO 151
<211> LENGTH: 20
<212> TYPE: DNA
<213> ORGANISM: Escherichia coli

```
<400> SEQUENCE: 151
gggttggagc gcgtctggaa                                               20

<210> SEQ ID NO 152
<211> LENGTH: 20
<212> TYPE: DNA
<213> ORGANISM: Escherichia coli

<400> SEQUENCE: 152
cgggatcggg ttggagcgcg                                               20

<210> SEQ ID NO 153
<211> LENGTH: 20
<212> TYPE: DNA
<213> ORGANISM: Escherichia coli

<400> SEQUENCE: 153
cacgggatcg ggttggagcg                                               20

<210> SEQ ID NO 154
<211> LENGTH: 20
<212> TYPE: DNA
<213> ORGANISM: Escherichia coli

<400> SEQUENCE: 154
ctgacttcca cttcctgcgg                                               20

<210> SEQ ID NO 155
<211> LENGTH: 20
<212> TYPE: DNA
<213> ORGANISM: Escherichia coli

<400> SEQUENCE: 155
tgcccgacca gataagaact                                               20

<210> SEQ ID NO 156
<211> LENGTH: 20
<212> TYPE: DNA
<213> ORGANISM: Escherichia coli

<400> SEQUENCE: 156
ttccgagtca atctgcccga                                               20

<210> SEQ ID NO 157
<211> LENGTH: 20
<212> TYPE: DNA
<213> ORGANISM: Escherichia coli

<400> SEQUENCE: 157
aatcgtcggt gtccacttcc                                               20

<210> SEQ ID NO 158
<211> LENGTH: 20
<212> TYPE: DNA
<213> ORGANISM: Escherichia coli

<400> SEQUENCE: 158
gaccactttg cgcatccggc                                               20

<210> SEQ ID NO 159
<211> LENGTH: 20
<212> TYPE: DNA
```

-continued

```
<213> ORGANISM: Escherichia coli

<400> SEQUENCE: 159
gatgttgacc actttgcgca                                          20

<210> SEQ ID NO 160
<211> LENGTH: 20
<212> TYPE: DNA
<213> ORGANISM: Escherichia coli

<400> SEQUENCE: 160
atctccggtt ccatggcatt                                          20

<210> SEQ ID NO 161
<211> LENGTH: 20
<212> TYPE: DNA
<213> ORGANISM: Escherichia coli

<400> SEQUENCE: 161
tttttccatc tccggttcca                                          20

<210> SEQ ID NO 162
<211> LENGTH: 20
<212> TYPE: DNA
<213> ORGANISM: Escherichia coli

<400> SEQUENCE: 162
ccctttcagt tcttcgtcgg                                          20

<210> SEQ ID NO 163
<211> LENGTH: 20
<212> TYPE: DNA
<213> ORGANISM: Escherichia coli

<400> SEQUENCE: 163 gcggtttttcc ctttcagttc                                         20

<210> SEQ ID NO 164
<211> LENGTH: 20
<212> TYPE: DNA
<213> ORGANISM: Escherichia coli

<400> SEQUENCE: 164
actctgcggt ttccctttc                                           20

<210> SEQ ID NO 165
<211> LENGTH: 20
<212> TYPE: DNA
<213> ORGANISM: Escherichia coli

<400> SEQUENCE: 165 cgccttttc cagacgtgca                                           20

<210> SEQ ID NO 166
<211> LENGTH: 20
<212> TYPE: DNA
<213> ORGANISM: Escherichia coli

<400> SEQUENCE: 166
cacttcgcct ttttccagac                                          20

<210> SEQ ID NO 167
<211> LENGTH: 20
```

-continued

```
<212> TYPE: DNA
<213> ORGANISM: Escherichia coli

<400> SEQUENCE: 167
tttccagcac ttcgccttt                                              20

<210> SEQ ID NO 168
<211> LENGTH: 20
<212> TYPE: DNA
<213> ORGANISM: Escherichia coli

<400> SEQUENCE: 168
cagattttcc agcacttcgc                                             20

<210> SEQ ID NO 169
<211> LENGTH: 20
<212> TYPE: DNA
<213> ORGANISM: Escherichia coli

<400> SEQUENCE: 169
acttgcctca cgtaccacgg                                             20

<210> SEQ ID NO 170
<211> LENGTH: 20
<212> TYPE: DNA
<213> ORGANISM: Escherichia coli

<400> SEQUENCE: 170
gacgcgctta cttgcctcac                                             20

<210> SEQ ID NO 171
<211> LENGTH: 20
<212> TYPE: DNA
<213> ORGANISM: Escherichia coli

<400> SEQUENCE: 171
gtgacgcata ccaaagacgc                                             20

<210> SEQ ID NO 172
<211> LENGTH: 20
<212> TYPE: DNA
<213> ORGANISM: Escherichia coli

<400> SEQUENCE: 172
taagaaccat accgccgagt                                             20

<210> SEQ ID NO 173
<211> LENGTH: 20
<212> TYPE: DNA
<213> ORGANISM: Escherichia coli

<400> SEQUENCE: 173
atttcggcga tgcagcgttc                                             20

<210> SEQ ID NO 174
<211> LENGTH: 20
<212> TYPE: DNA
<213> ORGANISM: Escherichia coli

<400> SEQUENCE: 174
ttccttcacc ggtacgcatt                                             20

<210> SEQ ID NO 175
```

<211> LENGTH: 20
<212> TYPE: DNA
<213> ORGANISM: Escherichia coli

<400> SEQUENCE: 175
gtttttcctt caccggtacg                                               20

<210> SEQ ID NO 176
<211> LENGTH: 20
<212> TYPE: DNA
<213> ORGANISM: Escherichia coli

<400> SEQUENCE: 176
cgttgcggtc agggtttttc                                               20

<210> SEQ ID NO 177
<211> LENGTH: 20
<212> TYPE: DNA
<213> ORGANISM: Escherichia coli

<400> SEQUENCE: 177
tcaggtaagc aggcagcgtt                                               20

<210> SEQ ID NO 178
<211> LENGTH: 20
<212> TYPE: DNA
<213> ORGANISM: Escherichia coli

<400> SEQUENCE: 178
taccggttag tgcgttcagg                                               20

<210> SEQ ID NO 179
<211> LENGTH: 20
<212> TYPE: DNA
<213> ORGANISM: Escherichia coli

<400> SEQUENCE: 179
ttgcgccagg tagtcgttga                                               20

<210> SEQ ID NO 180
<211> LENGTH: 20
<212> TYPE: DNA
<213> ORGANISM: Escherichia coli

<400> SEQUENCE: 180
gtcacgttgc gccaggtagt                                               20

<210> SEQ ID NO 181
<211> LENGTH: 20
<212> TYPE: DNA
<213> ORGANISM: Escherichia coli

<400> SEQUENCE: 181
agcggacggt tgttttcggc                                               20

<210> SEQ ID NO 182
<211> LENGTH: 20
<212> TYPE: DNA
<213> ORGANISM: Escherichia coli

<400> SEQUENCE: 182
ggaattcaaa cagcggacgg                                               20

-continued

```
<210> SEQ ID NO 183
<211> LENGTH: 20
<212> TYPE: DNA
<213> ORGANISM: Escherichia coli

<400> SEQUENCE: 183
aggccaagga attcaaacag                                                   20

<210> SEQ ID NO 184
<211> LENGTH: 20
<212> TYPE: DNA
<213> ORGANISM: Escherichia coli

<400> SEQUENCE: 184
ataccgacag tcaggccaag                                                   20

<210> SEQ ID NO 185
<211> LENGTH: 20
<212> TYPE: DNA
<213> ORGANISM: Escherichia coli

<400> SEQUENCE: 185
ttcgcgcttt gccggtgctg                                                   20

<210> SEQ ID NO 186
<211> LENGTH: 20
<212> TYPE: DNA
<213> ORGANISM: Escherichia coli

<400> SEQUENCE: 186
agccgtattc gttgttcgta                                                   20

<210> SEQ ID NO 187
<211> LENGTH: 20
<212> TYPE: DNA
<213> ORGANISM: Escherichia coli

<400> SEQUENCE: 187
cgcaggtagt caaagccgta                                                   20

<210> SEQ ID NO 188
<211> LENGTH: 20
<212> TYPE: DNA
<213> ORGANISM: Escherichia coli

<400> SEQUENCE: 188
atgttgtcgc gcaggtagtc                                                   20

<210> SEQ ID NO 189
<211> LENGTH: 20
<212> TYPE: DNA
<213> ORGANISM: Escherichia coli

<400> SEQUENCE: 189
gccatgttgt cgcgcaggta                                                   20

<210> SEQ ID NO 190
<211> LENGTH: 20
<212> TYPE: DNA
<213> ORGANISM: Escherichia coli

<400> SEQUENCE: 190
gtccacttcg tccaccagcg                                                   20
```

<210> SEQ ID NO 191
<211> LENGTH: 20
<212> TYPE: DNA
<213> ORGANISM: Escherichia coli

<400> SEQUENCE: 191
ggtgtacgcg cttcatcgat                                      20

<210> SEQ ID NO 192
<211> LENGTH: 20
<212> TYPE: DNA
<213> ORGANISM: Escherichia coli

<400> SEQUENCE: 192
cggtgtacgc gcttcatcga                                      20

<210> SEQ ID NO 193
<211> LENGTH: 20
<212> TYPE: DNA
<213> ORGANISM: Escherichia coli

<400> SEQUENCE: 193
gcgtttatac atttccgagc                                      20

<210> SEQ ID NO 194
<211> LENGTH: 20
<212> TYPE: DNA
<213> ORGANISM: Escherichia coli

<400> SEQUENCE: 194
cggatcaggt gcggaataat                                      20

<210> SEQ ID NO 195
<211> LENGTH: 20
<212> TYPE: DNA
<213> ORGANISM: Escherichia coli

<400> SEQUENCE: 195
ttcacctggc gagattttc                                       20

<210> SEQ ID NO 196
<211> LENGTH: 20
<212> TYPE: DNA
<213> ORGANISM: Escherichia coli

<400> SEQUENCE: 196
cagcaccaga ccacgttcgg                                      20

<210> SEQ ID NO 197
<211> LENGTH: 20
<212> TYPE: DNA
<213> ORGANISM: Escherichia coli

<400> SEQUENCE: 197
gccctctttc accagcagtt                                      20

<210> SEQ ID NO 198
<211> LENGTH: 20
<212> TYPE: DNA
<213> ORGANISM: Escherichia coli

<400> SEQUENCE: 198
cccttcatcc atgatgccct                                      20

<210> SEQ ID NO 199
<211> LENGTH: 20
<212> TYPE: DNA
<213> ORGANISM: Escherichia coli

<400> SEQUENCE: 199
ttggccggag agtacagaga					20

<210> SEQ ID NO 200
<211> LENGTH: 20
<212> TYPE: DNA
<213> ORGANISM: Escherichia coli

<400> SEQUENCE: 200
agcatgatgt tggccggaga					20

<210> SEQ ID NO 201
<211> LENGTH: 20
<212> TYPE: DNA
<213> ORGANISM: Escherichia coli

<400> SEQUENCE: 201
agcgccgccg ttacgtggtg					20

<210> SEQ ID NO 202
<211> LENGTH: 20
<212> TYPE: DNA
<213> ORGANISM: Escherichia coli

<400> SEQUENCE: 202
gtcacgggta aacagcgcat					20

<210> SEQ ID NO 203
<211> LENGTH: 20
<212> TYPE: DNA
<213> ORGANISM: Escherichia coli

<400> SEQUENCE: 203
caccttcttt cgcttccaca					20

<210> SEQ ID NO 204
<211> LENGTH: 20
<212> TYPE: DNA
<213> ORGANISM: Escherichia coli

<400> SEQUENCE: 204
cagcgtttgg ttttcgttct					20

<210> SEQ ID NO 205
<211> LENGTH: 20
<212> TYPE: DNA
<213> ORGANISM: Escherichia coli

<400> SEQUENCE: 205
ggtgatcgaa gccagcgttt					20

<210> SEQ ID NO 206
<211> LENGTH: 20
<212> TYPE: DNA
<213> ORGANISM: Escherichia coli

<400> SEQUENCE: 206

-continued gacggaagta gttctggaag					20

<210> SEQ ID NO 207
<211> LENGTH: 20
<212> TYPE: DNA
<213> ORGANISM: Escherichia coli

<400> SEQUENCE: 207
cccgccagtt tttcatacag					20

<210> SEQ ID NO 208
<211> LENGTH: 20
<212> TYPE: DNA
<213> ORGANISM: Escherichia coli

<400> SEQUENCE: 208
tcatccccgc cagtttttca					20

<210> SEQ ID NO 209
<211> LENGTH: 20
<212> TYPE: DNA
<213> ORGANISM: Escherichia coli

<400> SEQUENCE: 209
gaacaacgac ggtatccagc					20

<210> SEQ ID NO 210
<211> LENGTH: 20
<212> TYPE: DNA
<213> ORGANISM: Escherichia coli

<400> SEQUENCE: 210
gcctttcgca gtacgttctt					20

<210> SEQ ID NO 211
<211> LENGTH: 20
<212> TYPE: DNA
<213> ORGANISM: Escherichia coli

<400> SEQUENCE: 211
tagtacccac cagcaccggc					20

<210> SEQ ID NO 212
<211> LENGTH: 20
<212> TYPE: DNA
<213> ORGANISM: Escherichia coli

<400> SEQUENCE: 212
cggctttggt cagttcgttt					20

<210> SEQ ID NO 213
<211> LENGTH: 20
<212> TYPE: DNA
<213> ORGANISM: Escherichia coli

<400> SEQUENCE: 213
tgtgcttaat accggctttg					20

<210> SEQ ID NO 214
<211> LENGTH: 20
<212> TYPE: DNA
<213> ORGANISM: Escherichia coli

<400> SEQUENCE: 214
gttggcgtgg aatttggcgt    20

<210> SEQ ID NO 215
<211> LENGTH: 20
<212> TYPE: DNA
<213> ORGANISM: Escherichia coli

<400> SEQUENCE: 215
gcctgagcaa caatcgccgc    20

<210> SEQ ID NO 216
<211> LENGTH: 20
<212> TYPE: DNA
<213> ORGANISM: Escherichia coli

<400> SEQUENCE: 216
ctgtaccacg acccgccata    20

<210> SEQ ID NO 217
<211> LENGTH: 20
<212> TYPE: DNA
<213> ORGANISM: Escherichia coli

<400> SEQUENCE: 217
tatctgtacc acgacccgcc    20

<210> SEQ ID NO 218
<211> LENGTH: 20
<212> TYPE: DNA
<213> ORGANISM: Escherichia coli

<400> SEQUENCE: 218
ctgcctgcca gctaccaccg    20

<210> SEQ ID NO 219
<211> LENGTH: 20
<212> TYPE: DNA
<213> ORGANISM: Escherichia coli

<400> SEQUENCE: 219
tttccagcgc ggcaacttct    20

<210> SEQ ID NO 220
<211> LENGTH: 20
<212> TYPE: DNA
<213> ORGANISM: Escherichia coli

<400> SEQUENCE: 220
tttgctctgc ggtcggattt    20

<210> SEQ ID NO 221
<211> LENGTH: 20
<212> TYPE: DNA
<213> ORGANISM: Escherichia coli

<400> SEQUENCE: 221
tttttcaatt tgctctgcgg    20

<210> SEQ ID NO 222
<211> LENGTH: 20
<212> TYPE: DNA
<213> ORGANISM: Escherichia coli -continued

```
<400> SEQUENCE: 222
accgcatcgt gacgtacctg                                              20

<210> SEQ ID NO 223
<211> LENGTH: 20
<212> TYPE: DNA
<213> ORGANISM: Escherichia coli

<400> SEQUENCE: 223
ccagtaccgc atcgtgacgt                                              20

<210> SEQ ID NO 224
<211> LENGTH: 20
<212> TYPE: DNA
<213> ORGANISM: Escherichia coli

<400> SEQUENCE: 224
gcttccagta ccgcatcgtg                                              20

<210> SEQ ID NO 225
<211> LENGTH: 20
<212> TYPE: DNA
<213> ORGANISM: Escherichia coli

<400> SEQUENCE: 225
accgatgata tgcaggccac                                              20

<210> SEQ ID NO 226
<211> LENGTH: 20
<212> TYPE: DNA
<213> ORGANISM: Escherichia coli

<400> SEQUENCE: 226
acgaccagaa cgaccgcgca                                              20

<210> SEQ ID NO 227
<211> LENGTH: 20
<212> TYPE: DNA
<213> ORGANISM: Escherichia coli

<400> SEQUENCE: 227
cccctgacga ccagaacgac                                              20

<210> SEQ ID NO 228
<211> LENGTH: 20
<212> TYPE: DNA
<213> ORGANISM: Escherichia coli

<400> SEQUENCE: 228 catcccctg acgaccagaa                                               20

<210> SEQ ID NO 229
<211> LENGTH: 20
<212> TYPE: DNA
<213> ORGANISM: Escherichia coli

<400> SEQUENCE: 229
gaaacgggaa gaaccagcat                                              20

<210> SEQ ID NO 230
<211> LENGTH: 20
<212> TYPE: DNA
<213> ORGANISM: Escherichia coli
```

```
<400> SEQUENCE: 230
cgacaggtag aaacgggaag                                              20

<210> SEQ ID NO 231
<211> LENGTH: 20
<212> TYPE: DNA
<213> ORGANISM: Escherichia coli

<400> SEQUENCE: 231
ggaagcaaaa atacgcatca                                              20

<210> SEQ ID NO 232
<211> LENGTH: 20
<212> TYPE: DNA
<213> ORGANISM: Escherichia coli

<400> SEQUENCE: 232
ggtcggaagc aaaaatacgc                                              20

<210> SEQ ID NO 233
<211> LENGTH: 20
<212> TYPE: DNA
<213> ORGANISM: Escherichia coli

<400> SEQUENCE: 233
cggatactcg gtcggaagca                                              20

<210> SEQ ID NO 234
<211> LENGTH: 20
<212> TYPE: DNA
<213> ORGANISM: Escherichia coli

<400> SEQUENCE: 234
acccagttta cgcatcatgc                                              20

<210> SEQ ID NO 235
<211> LENGTH: 20
<212> TYPE: DNA
<213> ORGANISM: Escherichia coli

<400> SEQUENCE: 235
acgggtgttc aatggcttcg                                              20

<210> SEQ ID NO 236
<211> LENGTH: 20
<212> TYPE: DNA
<213> ORGANISM: Escherichia coli

<400> SEQUENCE: 236
atcgctttag tcacccacgg                                              20

<210> SEQ ID NO 237
<211> LENGTH: 20
<212> TYPE: DNA
<213> ORGANISM: Escherichia coli

<400> SEQUENCE: 237
ctttcaactt tacgctgggc                                              20

<210> SEQ ID NO 238
<211> LENGTH: 20
<212> TYPE: DNA
```

-continued

```
<213> ORGANISM: Escherichia coli

<400> SEQUENCE: 238
acggctttca actttacgct                                               20

<210> SEQ ID NO 239
<211> LENGTH: 20
<212> TYPE: DNA
<213> ORGANISM: Escherichia coli

<400> SEQUENCE: 239
tggtttcgct cacatcgctg                                               20

<210> SEQ ID NO 240
<211> LENGTH: 20
<212> TYPE: DNA
<213> ORGANISM: Escherichia coli

<400> SEQUENCE: 240
gtaggcatca atggtcgctt                                               20

<210> SEQ ID NO 241
<211> LENGTH: 20
<212> TYPE: DNA
<213> ORGANISM: Escherichia coli

<400> SEQUENCE: 241
ccacatttct tccagcgact                                               20

<210> SEQ ID NO 242
<211> LENGTH: 20
<212> TYPE: DNA
<213> ORGANISM: Escherichia coli

<400> SEQUENCE: 242
atcccacatt tcttccagcg                                               20

<210> SEQ ID NO 243
<211> LENGTH: 20
<212> TYPE: DNA
<213> ORGANISM: Escherichia coli

<400> SEQUENCE: 243
tcacgcagcg tctcttcatg                                               20

<210> SEQ ID NO 244
<211> LENGTH: 20
<212> TYPE: DNA
<213> ORGANISM: Escherichia coli

<400> SEQUENCE: 244
cctttctcga agtgacgcat                                               20

<210> SEQ ID NO 245
<211> LENGTH: 20
<212> TYPE: DNA
<213> ORGANISM: Escherichia coli

<400> SEQUENCE: 245
ccacagggag tcaagcgttt                                               20

<210> SEQ ID NO 246
<211> LENGTH: 20
```

```
<212> TYPE: DNA
<213> ORGANISM: Escherichia coli

<400> SEQUENCE: 246
tcgctgccag gtgctctttc                                               20

<210> SEQ ID NO 247
<211> LENGTH: 20
<212> TYPE: DNA
<213> ORGANISM: Escherichia coli

<400> SEQUENCE: 247
gtccatcgct gccaggtgct                                               20

<210> SEQ ID NO 248
<211> LENGTH: 20
<212> TYPE: DNA
<213> ORGANISM: Escherichia coli

<400> SEQUENCE: 248
acgcagatag tccatcgctg                                               20

<210> SEQ ID NO 249
<211> LENGTH: 20
<212> TYPE: DNA
<213> ORGANISM: Escherichia coli

<400> SEQUENCE: 249
cttcggatct ttctgtgcgt                                               20

<210> SEQ ID NO 250
<211> LENGTH: 20
<212> TYPE: DNA
<213> ORGANISM: Escherichia coli

<400> SEQUENCE: 250
cgtttgtatt cctgcttcgg                                               20

<210> SEQ ID NO 251
<211> LENGTH: 20
<212> TYPE: DNA
<213> ORGANISM: Escherichia coli

<400> SEQUENCE: 251
atcgctgcaa acatggagaa                                               20

<210> SEQ ID NO 252
<211> LENGTH: 20
<212> TYPE: DNA
<213> ORGANISM: Escherichia coli

<400> SEQUENCE: 252
ccatacgacg ctgttgttcc                                               20

<210> SEQ ID NO 253
<211> LENGTH: 20
<212> TYPE: DNA
<213> ORGANISM: Escherichia coli

<400> SEQUENCE: 253
ggcttccata cgacgctgtt                                               20

<210> SEQ ID NO 254
```

-continued

```
<211> LENGTH: 20
<212> TYPE: DNA
<213> ORGANISM: Escherichia coli

<400> SEQUENCE: 254
cgctaaacgc tcggcttcca                                              20

<210> SEQ ID NO 255
<211> LENGTH: 20
<212> TYPE: DNA
<213> ORGANISM: Escherichia coli

<400> SEQUENCE: 255
gctaagctgc tgcatttgcg                                              20

<210> SEQ ID NO 256
<211> LENGTH: 20
<212> TYPE: DNA
<213> ORGANISM: Escherichia coli

<400> SEQUENCE: 256
ctactttgcg ctctccggtt                                              20

<210> SEQ ID NO 257
<211> LENGTH: 20
<212> TYPE: DNA
<213> ORGANISM: Escherichia coli

<400> SEQUENCE: 257
ttacgtccta ctttgcgctc                                              20

<210> SEQ ID NO 258
<211> LENGTH: 20
<212> TYPE: DNA
<213> ORGANISM: Escherichia coli

<400> SEQUENCE: 258
aaccgcacgg gcaaggatcg                                              20

<210> SEQ ID NO 259
<211> LENGTH: 20
<212> TYPE: DNA
<213> ORGANISM: Escherichia coli

<400> SEQUENCE: 259
accagaaccg cacgggcaag                                              20

<210> SEQ ID NO 260
<211> LENGTH: 20
<212> TYPE: DNA
<213> ORGANISM: Escherichia coli

<400> SEQUENCE: 260
tttttaccag aaccgcacgg                                              20

<210> SEQ ID NO 261
<211> LENGTH: 20
<212> TYPE: DNA
<213> ORGANISM: Escherichia coli

<400> SEQUENCE: 261
caggtagtcg ttgacggtaa                                              20
```

```
<210> SEQ ID NO 262
<211> LENGTH: 18
<212> TYPE: DNA
<213> ORGANISM: Escherichia coli

<400> SEQUENCE: 262
caggtagtcg ttgacggt                                                 18

<210> SEQ ID NO 263
<211> LENGTH: 20
<212> TYPE: DNA
<213> ORGANISM: Escherichia coli

<400> SEQUENCE: 263
cggaagtagt tctggaaggt                                               20

<210> SEQ ID NO 264
<211> LENGTH: 20
<212> TYPE: DNA
<213> ORGANISM: Escherichia coli

<400> SEQUENCE: 264
cgaccgcgca actggttatc                                               20

<210> SEQ ID NO 265
<211> LENGTH: 20
<212> TYPE: DNA
<213> ORGANISM: Escherichia coli

<400> SEQUENCE: 265
ccgcacgggc aaggatcgtt                                               20
```

1
ANTISENSE OLIGONUCLEOTIDE SEQUENCES AS INHIBITORS OF MICROORGANISMS

REFERENCE TO RELATED APPLICATIONS

This application claims benefit of U.S. Provisional Application Serial No. 60/052,160, filed Jul. 10, 1997, which application is incorporated herein by reference in its entirety.

BACKGROUND OF THE INVENTION

1. Field of the Invention

This invention relates to antisense oligonucleotides which modulate the activity of the ribonucleotide reductase genes and the secA genes in microorganisms. This invention is also related to methods of using such compounds in inhibiting the growth of microorganisms.

These antisense oligonucleotides are particularly useful in treating pathological conditions in mammals which are mediated by the growth of microorganisms. Accordingly, this invention also relates to pharmaceutical compositions comprising a pharmaceutically acceptable excipient and an effective amount of a compound of this invention.

These antisense oligonucleotides may also be used as anti-microbial agents for agricultural applications such as crop protection.

2. References

The following publications, patent applications and patents are cited in this application as superscript numbers:

1. Nordlund and Eklund "Structure and function of the *Escherichia coli* ribonucleotide reductase protein R2", *J. Mol. Biol.* (1993) 232:123–164;
2. Carlson et al., "Primary structure of the *Escherichia coli* ribonucleoside diphosphate reductase operon", *PNAS USA* (1984) 81:4294–4297;
3. Nilsson et al., "Nucleotide sequence of the gene coding for the large subunit of ribonucleotide reductase of *Escherichia coli* Correction", *Nucleic Acids Research* (1988) 16:4174;
4. P. Reichard, "The anaerobic ribonucleotide reductase from *Escherichia coli*", *J. Biol. Chem.* (1993) 268:8383–8386;
5. Nordlund et al., *Nature* (1990) 345:593–598;
6. der Blaauwen et al., "Inhibition of preprotein translocation and reversion of the membrane inserted state of secA by a carboxyl terminus binding Mab", *Biochemistry* (1997) 36:9159–9168;
7. McNicholas et al., "Dual regulation of *Escherichia coli* secA translation by distinct upstream elements", *J. Mol. Biol.* (1997) 265:128–141;
8. U.S. Pat. No. 5,294,533;
9. Gasparro et al., "Photoactivatable antisense DNA: Suppression of ampicillin resistance in normally resistant *Escherichia coli*", *Antisense Research and Development* (1991) 1:117–140;
10. White et al., "Inhibition of the multiple antibiotic resistance (mar) operon in *Escherichia coli* by antisense DNA analogs", *Antimicrobial Agents and Chemotherapy* (1997) 41:2699–2704;
11. Nielsen et al., *Science* (1991) 354:1497;
12. Good and Nielsen, "Inhibition of translation and bacterial growth by peptide nucleic acid targeted to ribosomal RNA", *PNAS USA* (1998) 95:2073–2076;
13. Buchardt, deceased, et al., U.S. Pat. No. 5,766,855;
14. Buchardt, deceased, et al., U.S. Pat. No. 5,719,262;
15. U.S. Pat. No. 5,034,506;
16. Altschul, et al., "Basic local alignment search tool", *J. Mol. Biol.* (1990) 215:403–10;
17. Devereux. et al., "A comprehensive set of sequence analysis programs for the VAX", *Nucleic Acids Res.* (1984) 12:387–395;
18. Sambrook et al., *Molecular Cloning: A Laboratory Manual*, Cold Spring Harbor Laboratory, New York (1989, 1992);
19. Ausubel et al., *Current Protocols in Molecular Biology*, John Wiley and Sons, Baltimore Md. (1989);
20. Chang et al., Somatic Gene Therapy, CRC Press, Ann Arbor Mich. (1995);
21. Vega et al., *Gene Targeting*, CRC Press, Ann Arbor Mich. (1995);
22. *Vectors: A Survey of Molecular Cloning Vectors and Their Uses*, Butterworths, Boston Mass. (1988)
23. U.S. Pat. No. 5,023,252, issued June 11, 1991
24. Felgner et al., U.S. Pat. No. 5,580,859.
25. U.S. Pat. No. 5,011,472
26. *Remington's Pharmaceutical Sciences*, Mace Publishing Company, Philadelphia Pa. 17$^{th}$ ed. (1985);
27. Perbal, *A Practical Guide to Molecular Cloning*, John Wiley & Sons, New York (1988).
28. *PCR Protocols: A Guide To Methods And Applications*, Academic Press, San Diego, Calif. (1990).
29. Dower, W. J., *Nucleic Acids Res.* (1988) 16:6127;
30. Neuman et al., *EMBO J.* (1982) 1:841;
31. Taketo A., *Biochim Biophys. Acta* (1988) 949:318;
32. Miller J. H. *Experiments in Molecular Genetics*, Cold Spring Harbor Laboratory Press, Cold Spring Harbor, N.Y. (1972);
33. Horwitz J. P., *J. Med. Chem.* (1964) 7:574;
34. Mann et al., *Biochem.*(1991) 30:1939;
35. Olsvik, et al., *Acta Pathol. Microbiol. Immunol. Scand.* [B] (1982) 90:319;
36. Laemmli, U. K., *Nature* (1970) 227:680;
37. Choy et al., *Cancer Res.*(1988) 48:2029;
38. Wright and Anazodo, *Cancer J.* (1988) 8:185–189;
39. Chan et al., *Biochemistry* (1993) 32:12835–12840;
40. Carpentier P. L., *Microbiology* 4$^{th}$ ed. W.B.Saunders Company (1977); and
41. Wright et al., *Adv. Enzyme Regul.* (1981) 19:105–127.

All of the above publications, patent applications and patents are herein incorporated by reference in their entirety to the same extent as if each individual publication, patent application or patent was specifically and individually indicated to be incorporated by reference in its entirety.

3. State of the Art

Ribonucleotide reductase catalyzes the de novo production of deoxyribonucleotides. The enzyme reduces the four main ribonucleotides to the corresponding deoxyribonucleotides required for DNA synthesis and repair (Wright et al.[41]).

In mammalian and bacterial cells, de novo production of deoxyribonucleotides by ribonucleotide reductase is usually highly regulated on different levels in order to produce the correct amount of deoxyribonucleotides for DNA synthesis. In the DNA viruses, the metabolism of the host cell is directed towards production of viral DNA by virus encoded ribonucleotide reductases (Nordlund and Eklund[1]).

Mammalian cells and many DNA viruses and prokaryotes, have a heterodimeric iron-containing ribonucleotide reductase enzyme of the $\alpha_2\beta_2$ type. For example, ribonucleotide reductase from *E. coli* is a multi-subunit $\alpha_2\beta_2$ enzyme where the two homo-dimeric proteins are denoted R1 and R2. The larger $\alpha_2$ protein, R1, contains the binding sites for substrate and allosteric effectors and also the redox-active cysteine residues. Protein R1 has a molecular mass of 2×86,000 where each subunit contains 761 residues. The smaller $\beta_2$ protein, denoted R2, contains the dinuclear ferric center and a stable free tyrosyl radical necessary for the enzymatic activity. The R2 protein has a molecular mass of 2×43,500, where each subunit contains 375 amino acid residues (Nordlund and Eklund[1]).

The nucleotide sequence of the *E. coli* K-12 DNA comprising the operon for the structural genes of the subunits of ribonucleotide reductase has been determined. The DNA sequence includes a total length of 8557 nucleotides. An open reading frame between nucleotides 3506 and 5834 has been identified as the nrdA gene. An open reading frame between nucleotides 6012 and 7139 encoding a 375-amino acid polypeptide has been identified as the nrdB gene (Carlson et al.[2], and Nilsson et al.[3]). The sequences of the nrdA and nrdB genes for *E. coli* are shown in FIGS. 1 and 2.

In *E. coli*, the synthesis of ribonucleotide reductase is controlled at the level of transcription. The nrdA and nrdB genes direct the synthesis of a 3.2 kilobase polycistronic mRNA. Perturbations in DNA replication, either a shift up in growth conditions or an inhibition of DNA synthesis leads to increased synthesis of nrd MRNA (Carlson et al.[2]).

A separate anaerobic ribonucleotide reductase has also been identified from *E.coli*. The anaerobic *E. coli* reductase has a molecular mass of 145 kD and is a homodimer. The gene for the anaerobic reductase (nrdD) has been cloned and sequenced (P. Reichard[4]).

The ribonucleotide reductase R2 genomic or cDNA sequences are known for several other species such as bacteriophage T4, clam, mouse, *Saccharomyces cerevisiae*, vaccinia, herpes simplex virus types 1 and 2, varicella and Epstein-Barr virus (Nordlund et al.[5]). The sequence of the nrdE and nrdF which code for the ribonucleotide reductase genes of *S. typhimurium* are shown in FIG. 3. The sequence of the ribonucleotide reductase gene of *Lactococcus lactis* is shown in FIG. 4.

The secA gene of *E. coli* encodes for one component of a multi-component system for the secretion of proteins across the inner membrane of *E. coli* (der Blaauwen et al.[6]). The complete system consists of the SecB protein, a cytosolic chaperone, the SecA protein, the translocation ATPase and the heterotrimeric integral membrane SecY/SecE/SecG complex, which along with SecA serves as the preprotein channel. SecA protein plays a central role in the secretion process by binding the preprotein, secB protein, anionic phospholipids and SecY/SecE/SecG protein. These interactions allow SecA to recognize soluble preprotein and recruit it to translocation sites in the inner membrane. Once such protein translocation complexes have assembled; further steps require an ATP-driven cycle of insertion and de-insertion of secA protein with the inner membrane, where each cycle appears to be coupled to the translocation of a segment of the preprotein.

SecA is the only component of the secretion apparatus that has been shown to be regulated. SecA is the second gene in the geneX-secA operon and its translation varies over a tenfold range depending on the status of protein secretion in the cell. During protein-export proficient conditions secA auto-represses its translation by binding to a site that overlaps the secA ribosome-binding site of genes-secA RNA. SecA protein can also dissociate a preformed 30 S-tRNA$^{MET}$-genes-secA RNA ternary complex in vitro. However, during a protein export block secA translation increases substantially although the mechanism responsible for this regulatory response has not been elucidated (McNicholas et al.[7]). The sequence of the secA gene of *E. coli* is shown in FIG. 5.

The secA gene sequence has been identified for a number of other species including *Mycobacterium bovis* (FIG. 6), *Mycobacterium tuberculosis* (FIG. 7), *Staphylococcus aureus* (FIG. 8), *Staphylococcus carnosus* (FIG. 9), *Bacillus subtilis, Bacillus firnus, Listeria monocytogenes, Mycobacterium smegmatis, Borrelia burgdorferi, P. sativum, S. griseus*, and Synechoccus sp.

Antibiotics are important pharmaceuticals for the treatment of infectious diseases in a variety of animals including man. The tremendous utility and efficacy of antibiotics results from the interruption of bacterial (prokaryotic) cell growth with minimal damage or side effects to the eukaryotic host harboring the pathogenic organisms. In general, antibiotics destroy bacteria by interfering with the DNA replication, DNA to RNA transcription, translation (that is RNA to protein) or cell wall synthesis.

Although bacterial antibiotic resistance has been recognized since the advent of antimicrobial agents, the consequence of the emergence of resistant microorganisms, such resistance was historically controlled by the continued availability of effective alternative drugs. Now, drug resistance has emerged as a serious medical problem in the community, leading to increasing morbidity and mortality. The problem is worsened by the growing number of pathogens resistant to multiple, structurally unrelated drugs. The situation has become so desperate that antibiotics once removed from use because of toxic effects may be prescribed in an attempt to deal with the otherwise untreatable drug resistant bacteria.

Antisense oligonucleotides have been used to decrease the expression of specific genes by inhibiting transcription or translation of the desired gene and thereby achieving a phenotypic effect based upon the expression of that gene (Wright and Anazado[38]). For example, antisense RNA is important in plasmid DNA copy number control, in development of bacteriophage P22. Antisense RNA's have been used experimentally to specifically inhibit in vitro translation of mRNA coding specifically from Drosophila hsp23, to inhibit Rous sarcoma virus replication and to inhibit 3T3 cell proliferation when directed toward the oncogene c-fos. Furthermore, it is not necessary to use the entire antisense MRNA since a short antisense oligonucleotide can inhibit gene expression. This is seen in the inhibition of chloramphenicol acetyltransferase gene expression and in the inhibition of specific antiviral activity to vesicular stomatitus virus by inhibiting the N-protein initiation site. Antisense oligonucleotides directed to the macromolecular synthesis operon of bacteria, containing the rpsU gene, the rpoD gene and the dnaG gene have been used for the detection of bacteria. (U.S. Pat. No. 5,294,533[8]). Furthermore, photoactivatable antisense DNA complementary to a segment of the P-lactamase gene has been used to suppress ampicillin resistance in normally resistant *E. coli* (Gasparro et al.[9]). Antisense DNA analogs have also been used to inhibit the multiple antibiotic resistant (mar) operon in *Escherichia coli* (White et al.[10]).

Accordingly, there is a need to develop antisense oligonucleotides which will act to inhibit the growth of microorganisms.

SUMMARY OF THE INVENTION

This invention is directed to antisense oligonucleotides which modulate the expression of the ribonucleotide reductase and secA genes in microorganisms and pharmaceutical compositions comprising such antisense oligonucleotides. This invention is also related to methods of using such antisense oligonucleotides for inhibiting the growth of microorganisms.

Accordingly, in one of its composition aspects, this invention is directed to an antisense oligonucleotide, which oligonucleotide is nuclease resistant and comprises from about 3 to about 50 nucleotides, which nucleotides are complementary to the ribonucleotide reductase gene or the secA gene of a microorganism. The antisense oligonucleotide may have one or more phosphorothioate internucleotide linkages.

In another of its composition aspects, this invention is directed to an antisense oligonucleotide comprising from about 3 to about 50 nucleotides which is capable of binding to the ribonucleotide reductase gene or the secA gene of a microorganism, wherein the oligonucleotide comprises all or part of a sequence selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; SEQ ID NO:152; SEQ ID NO:164; SEQ ID NO:176; SEQ ID NO:186; SEQ ID NO:188; SEQ ID NO:189; SEQ ID NO: 191; SEQ ID NO: 192; SEQ ID NO:195; SEQ ID NO:197; SEQ ID NO:206; SEQ ID NO:212; SEQ ID NO:220; SEQ ID NO:229; SEQ ID NO:235; SEQ ID NO:254; SEQ ID NO:261; SEQ ID NO:262; SEQ ID NO:263; SEQ ID NO:264; and SEQ ID NO:265.

In still another of its composition aspects, this invention is directed to a pharmaceutical composition comprising a pharmaceutically acceptable excipient and an effective amount of an antisense oligonucleotide, which oligonucleotide is nuclease resistant and comprises from about 3 to about 50 nucleotides, which nucleotides are complementary to the ribonucleotide reductase gene or the secA gene of a microorganism. The oligonucleotide may be modified, for example, the oligonucleotide may have one or more phosphorothioate internucleotide linkages.

In one of its method aspects, this invention is directed to a method for inhibiting the expression of the ribonucleotide reductase gene in a microorganism having a ribonucleotide reductase gene comprising, administering to said microorganism or to a cell infected with said microorganism an effective amount of an antisense oligonucleotide comprising from at least about 3 nucleotides which are complementary to the ribonucleotide reductase gene of the microorganism under conditions such that the expression of the ribonucleotide reductase gene is inhibited.

In another of its method aspects, this invention is directed to a method for inhibiting the expression of the secA gene in a microorganism having a secA gene, comprising administering to said microorganism an effective amount of an antisense oligonucleotide comprising from at least about 3 nucleotides which are complementary to the secA gene of the microorganism under conditions such that expression of the secA gene is inhibited.

In one of its method aspects, this invention is directed to a method for inhibiting the growth of a microorganism encoding a ribonucleotide reductase gene or a secA gene, which method comprises administering to said microorganism or a cell infected with said microorganism an effective amount of an antisense oligonucleotide comprising from at least about 3 nucleotides which are complementary to either the ribonucleotide reductase gene or the secA gene of the microorganism under conditions such that the growth of the microorganism is inhibited. Preferably, the antisense oligonucleotide is selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; SEQ ID NO:152; SEQ ID NO:164; SEQ ID NO:176; SEQ ID NO:186; SEQ ID NO:188; SEQ ID NO:189; SEQ ID NO:191; SEQ ID NO:192; SEQ ID NO:195; SEQ ID NO:197; SEQ ID NO:206; SEQ ID NO:212; SEQ ID NO:220; SEQ ID NO:229; SEQ ID NO:235; SEQ ID NO:254; SEQ ID NO:261; SEQ ID NO:262; SEQ ID NO:263; SEQ ID NO:264; and SEQ ID NO:265.

In another of its method aspects, this invention is directed to a method for treating a mammalian pathologic condition mediated by a microorganism, which method comprises identifying a mammal having a pathologic condition mediated by a microorganism having a ribonucleotide reductase gene or a secA gene and administering to said mammal an effective amount of an antisense oligonucleotide comprising from at least about 3 nucleotides which are complementary to either the ribonucleotide reductase gene or the secA gene of the microorganism under conditions such that the growth of the microorganism is inhibited.

BRIEF DESCRIPTION OF THE DRAWINGS

FIG. 1 is the sequence of the *E. coli* nrdA gene encoding the ribonucleotide reductase R1 subunit [SEQ ID NO:1].

FIG. 2 is the sequence of the *E. coli* nrdB gene encoding the ribonucleotide reductase R2 subunit [SEQ ID NO:2]. The nrdB gene is encoded by nucleotides 7668 to 8798 of SEQ ID NO:2.

FIG. 3 is the sequence of the *S. typhimurium* nrdE and nrdF genes encoding the ribonucleotide reductase subunits [SEQ ID NO:3]. The nrdE gene is encoded by nucleotides 836 to 2980 and the nrdF gene is encoded by nucleotides 2991 to 3950 of SEQ ID NO:3.

FIG. 4 is the sequence of the *Lactococcus lactis* nrdEF operon encoding ribonucleotide reductase [SEQ ID NO:4].

FIG. 5 is the sequence of the *E. coli* secA gene [SEQ ID NO:5].

FIG. 6 is the sequence of the *Mycobacterium bovis* secA gene [SEQ ID NO:6].

FIG. 7 is the sequence of the *Mycobacterium tuberculosis* secA gene [SEQ ID NO:7].

FIG. 8 is the sequence of the *Staphylococcus aureus* secA gene [SEQ ID NO:8].

FIG. 9 is the sequence of the *Staphylococcus carnosus* secA gene [SEQ ID NO:9].

FIG. 10 is the sequence of the bovine herpes virus ribonucleotide reductase small subunit gene [SEQ ID NO:10].

FIG. 11 is the sequence of the Herpes simplex virus type 1 UL39 gene encoding ribonucleotide reductase 1 [SEQ ID NO:11].

FIG. 12 is the sequence of the Herpes simplex type 2 ribonucleotide reductase gene [SEQ ID NO:12]. The ribonucleotide reductase gene is encoded by nucleotides 419 to 3853 of SEQ ID NO:12.

FIG. 13 is the sequence of the equine herpes virus 4 ribonucleotide reductase large subunit and small subunit [SEQ ID NO:13]. The large subunit is encoded by nucleotides 77 to 2446 and the small subunit by nucleotides 2485–3447 of SEQ ID NO:13.

FIG. 19a shows the growth after treatment with 16 μM or 80 μM of antisense ES799 [SEQ ID NO:195]. FIG. 19b shows the growth after treatment with 20 AM of antisense ES1739 [SEQ ID NO:229]. FIG. 19c shows the growth after treatment with 80 μM of antisense ES851 [SEQ ID NO:197]. FIG. 19d shows the growth after treatment with 80 μM of antisense ES553 [SEQ ID NO:188]. FIG. 19e shows the growth after treatment with 80 μM of antisense ES646 [SEQ ID NO:191]. FIG. 19f shows the growth after treatment with 80 μM of antisense ES1845 [SEQ ID NO:235]. FIG. 19g shows the growth after treatment with 80 μM of antisense ES2537 [SEQ ID NO:254].

DETAILED DESCRIPTION OF THE INVENTION

Figure 15:
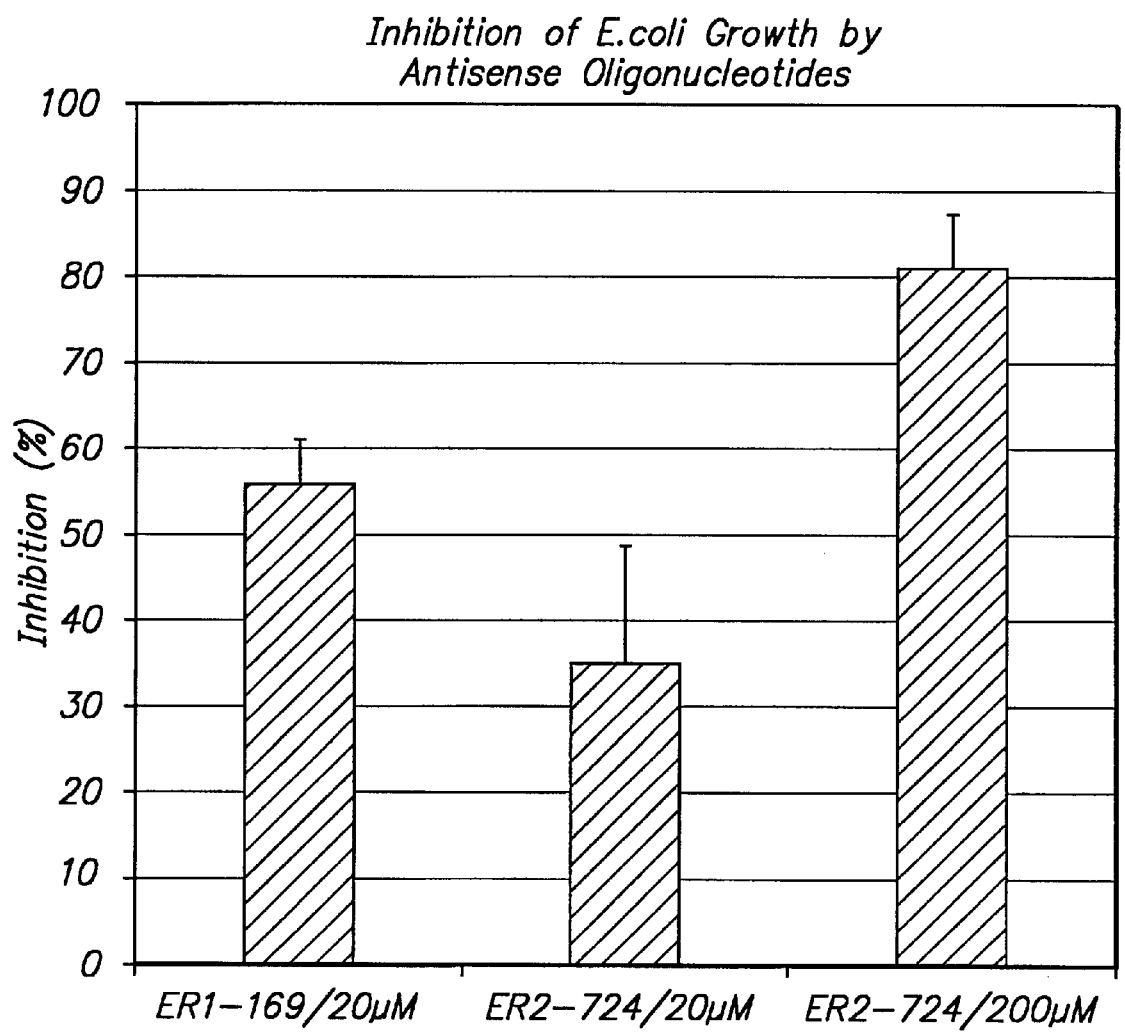
FIG. 15 is a graph of the inhibition of *E. coli* growth after treatment of *E. coli* cells with ribonculeotide reductase antisense oligonucleotides.

The present invention provides compounds that inhibit the growth of microbes by inhibiting the expression of a ribonucleotide reductase protein or the secA protein. Without being limited to any theory, the compounds inhibit the expression of the ribonucleotide reductase or the secA protein by inhibiting the transcription of the gene or the translation of the mRNA to protein. Such compounds include antisense oligonucleotides.

Definitions

As used herein, the following terms have the following meanings:

The term "antisense oligonucleotide" as used herein means a nucleotide sequence that is complementary to the MRNA for the desired gene. Preferably, the antisense oligonucleotide is complementary to the MRNA for ribonucleotide reductase or secA.

The term "oligonucleotide" refers to an oligomer or polymer of nucleotide or nucleoside monomers consisting of naturally occurring bases, sugars, and inter-sugar (backbone) linkages. The term also includes modified or substituted oligomers comprising non-naturally occurring monomers or portions thereof, which function similarly. Such modified or substituted oligomers may be preferred over naturally occurring forms because of the properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) or two or more oligonucleotides of the invention may be joined to form a chimeric oligonucleotide.

The antisense oligonucleotides of the present invention may be ribonucleic or deoxyribonucleic acids and may contain naturally occurring or synthetic monomeric bases, including adenine, guanine, cytosine, thymine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines or guanines, 5-trifluoromethyl uracil and 5-trifluoro cytosine.

The antisense oligonucleotides of the invention may also comprise modified phosphorus oxygen heteroatoms in the phosphate backbone, short chain alkyl or cycloalkyl inter-sugar linkages or short chain heteroatom or heterocyclic intersugar linkages. For example, the antisense oligonucleotides may contain methyl phosphonates, phosphorothioates, phosphorodithioates, phosphotriesters, and morpholino oligomers. In one embodiment of the invention, the antisense oligonucleotides comprise phosphorothioate bonds linking between the four to six 3'-terminus nucleotides. In another embodiment, the phosphorothioate bonds link all the nucleotides. The antisense oligonucleotides may also have sugar mimetics.

The antisense oligonucleotides of the invention may also comprise nucleotide analogues wherein the structure of the nucleotide is fundamentally altered. An example of such an oligonucleotide analogue is a peptide nucleic acid (PNA) wherein the deoxyribose (or ribose) phosphate backbone in DNA (or RNA) is replaced with a polyamide backbone which is similar to that found in peptides (Nielsen et al.[11]; Good and Nielsen[12]; Buchardt, deceased, et al.[13], U.S. Pat. No. 5,766,855; Buchardt, deceased, et al.[14], U.S. Pat. No. 5,719,262). PNA analogues have been shown to be resistant to degradation by enzymes and to have extended lives in vivo and in vitro. PNAs also bind more strongly to a complementary DNA sequence than to a naturally occurring nucleic acid molecule due to the lack of charge repulsion between the PNA strand and the DNA strand.

The oligonucleotides of the present invention may also include other nucleotides comprising polymer backbones, cyclic backbones, or acyclic backbones. For example, the nucleotides may comprise morpholino backbone structures (U.S. Pat. No. 5,034,506[15]).

The oligonucleotides of the present invention are "nuclease resistant" when they have either been modified such that they are not susceptible to degradation by DNA and RNA nucleases or alternatively they have been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example liposomes.

The oligonucleotides of the present invention may also contain groups, such as groups for improving the pharmacokinetic properties of an oligonucleotides, or groups for improving the pharmacodynamic properties of an oligonucleotide. Preferably, the oligonucleotides do not contain reporter groups or labels, such as fluorescent dyes or radioactive labels.

The antisense oligonucleotides may be complementary to the complete ribonucleotide reductase or secA gene including the introns. Preferably, the antisense oligonucleotides are complimentary to the mRNA region from the ribonucleotide reductase gene or the secA gene.

The antisense oligonucleotides may be selected from the sequence complementary to the ribonucletide reductase or secA genes such that the sequence exhibits the least likelihood of showing duplex formation, hair-pin formation, and homooligomer/sequence repeats but has a high to moderate potential to bind to the ribonucleotides reductase gene or the secA gene sequence and contains a GC clamp. These properties may be determined using the computer modeling program OLIGO Primer Analysis Software, Version 5.0 (distributed by National Biosciences, Inc., Plymouth, Minn.). This computer program allows the determination of a qualitative estimation of these five parameters.

Alternatively, the antisense oligonucleotides may also be selected on the basis that the sequence is highly conserved for either the ribonucleotide reductase or the secA genes between two or more microbial species. These properties may be determined using the BLASTN program (Altschul, et al.[16]) of the University of Wisconsin Computer group (GCG) software (Devereux J. et al.[17]) with the National Center for Biotechnology Information (NCBI) databases.

The antisense oligonucleotides generally comprise from at least about 3 nucleotides or nucleotide analogs, preferably from about 3 to about 50 nucleotides or nucleotide analogs, more preferably, from about 7 to about 35 nucleotides or nucleotide analogs, most preferably from about 15 to about 25 nucleotide or nucleotide analogs.

Preferably, the antisense oligonucleotides comprise from 3 to about 50 nucleotides or nucleotide analogs, more preferably from 20 to about 50 nucleotides or nucleotide analogs and further comprise all or part of the sequences set forth in Tables 1, 2, 3, and 4 (below). Preferably, the oligonucleotides complementary to the ribonucleotide reductase gene comprise SEQ ID NOS.: 14 to 157 as shown in Tables 1 and 2. Preferably, the antisense oligonucleotides complementary to the secA gene comprise the SEQ ID NOS.: 158 to 265 as shown in Tables 3 and 4.

TABLE 1

Antisense oligonucleotides that target the *Escherichia coli* K12 ribonucleotide reductase large subunit (R1)

| SEQ ID No.: | Name | Sequence 5'→3' | Tm (° C.) | ΔG (kcal/mol) |
|---|---|---|---|---|
| 14 | ER1-16 | CCGTCGCGCTTTGTCACCAG | 61.1 | −43.0 |
| 15 | ER1-24 | CTGTGCTACCGTCGCGCTTT | 57.8 | −42.0 |
| 16 | ER1-33 | TGATGCGCTCTGTGCTACCG | 57.2 | −40.2 |
| 17 | ER1-44 | TTTGTCGAGATTGAT GCGCT | 53.3 | −38.7 |
| 18 | ER1-58 | AGAACGCGATGGATTTTGTC | 51.7 | −38.4 |
| 19 | ER1-71 | TGCCGCCCAATCCAGAACGC | 64.6 | −46.0 |
| 20 | ER1-79 | AGTCCTTCTGCCGCCCAATC | 57.7 | −42.2 |
| 21 | ER1-128 | AAACTGAATGTGGGAGCGCA | 55.5 | −39.8 |
| 22 | ER1-169 | ATAATGGTTTCGTGGATGTC | 55.5 | −35.4 |
| 23 | ER1-180 | CGGCAGCCTTGATAATGGTT | 54.2 | −40.6 |
| 24 | ER1-218 | ATACTGATAATCCGGCGCAT | 51.4 | −39.4 |
| 25 | ER1-252 | TACGCAGGTGGAAGATCGCC | 57.3 | −41.4 |
| 26 | ER1-294 | GGTCGTACAGCGCAGGCGGC | 64.4 | −45.9 |
| 27 | ER1-320 | GCCCATCTCGACCATTTTCA | 54.7 | −39.7 |
| 28 | ER1-330 | TATCGTATTTGCCCATCTCG | 50.4 | −38.1 |
| 29 | ER1-423 | CGGCAGCATAAGAGAAGGTC | 51.6 | −38.5 |
| 30 | ER1-439 | CCTTCCAGCTGCTTAACGGC | 56.4 | −41.9 |
| 31 | ER1-450 | CCAGATATTTGCCTTCCAGC | 51.5 | −38.8 |
| 32 | ER1-479 | ATAGATTTCGCCGGTCACGC | 56.4 | −41.8 |
| 33 | ER1-495 | GGAACTGGGCGCTCTCATAG | 53.9 | −39.7 |
| 34 | ER1-504 | GAATATAAAGGAACTGGGCG | 48.5 | −38.0 |
| 35 | ER1-518 | GCACGCGGCAACTAGAATAT | 52.2 | −39.4 |

TABLE 1-continued

Antisense oligonucleotides that target the *Escherichia coli* K12 ribonucleotide reductase large subunit (R1)

| SEQ ID No.: | Name | Sequence 5'→3' | Tm (° C.) | ΔG (kcal/mol) |
|---|---|---|---|---|
| 36 | ER1-529 | TTCGAGAACAAGCACGCGGC | 60.8 | −43.3 |
| 37 | ER1-543 | TTTCACGCGGGTAGTTCGAG | 55.2 | −40.5 |
| 38 | ER1-566 | ACGCTTCACATATTGCAGGC | 52.2 | −38.7 |
| 39 | ER1-584 | GGAAACCGCGTCGTAAAAAC | 53.9 | −40.8 |
| 40 | ER1-592 | TTAAATGTGGAAACCGCGTC | 52.7 | −39.3 |
| 41 | ER1-617 | CATGATTGGCGTCGGCAGCG | 64.0 | −44.9 |
| 42 | ER1-628 | CGCACGCCGGACATGATTGG | 63.8 | −44.6 |
| 43 | ER1-640 | CGAGTCGGGGTACGCACGCC | 64.2 | −45.8 |
| 44 | ER1-667 | TCGATCAGTACGCAGGAGCT | 52.4 | −38.1 |
| 45 | ER1-680 | GCTGTCACCGCACTCGATCA | 56.9 | −39.1 |
| 46 | ER1-689 | GGAATCCAGGCTGTCACCGC | 59.0 | −41.9 |
| 47 | ER1-704 | GGAGGTGGCGTTGATGGAAT | 56.0 | −40.6 |
| 48 | ER1-716 | AACAATCGCGCTGGAGGTGG | 59.5 | −42.7 |
| 49 | ER1-778 | CTACCCAGCGCACGAATACG | 55.7 | −40.9 |
| 50 | ER1-817 | ATGCAGCCGGTATGGAACGC | 59.4 | −43.1 |
| 51 | ER1-829 | TTGTAGAACGGAATGCAGCC | 52.8 | −38.8 |
| 52 | ER1-846 | CCGCTGTCTGGAAATGTTTG | 53.1 | −38.6 |
| 53 | ER1-855 | AGGATTTCACCGCTGTCTGG | 54.0 | −39.2 |
| 54 | ER1-874 | CGCACACCGCCCTGAGAGCA | 63.9 | −44.0 |
| 55 | ER1-907 | CACATCGGGTAGAACAGCGT | 52.5 | −38.1 |
| 56 | ER1-925 | CTTTCCACTTCCAGATGCCA | 52.5 | −38.1 |
| 57 | ER1-964 | TTGCCTTCCACACCACGGTT | 57.5 | −40.8 |
| 58 | ER1-971 | CACGCGGTTGCCTTCCACAC | 60.8 | −42.5 |
| 59 | ER1-981 | CCATATGACGCACGCGGTTG | 59.4 | −42.1 |
| 60 | ER1-1034 | TTCACCTTTCAGCAGACGGG | 55.0 | −39.6 |
| 61 | ER1-1055 | CGGGCTGAACAGGGTGATAT | 53.8 | −39.6 |
| 62 | ER1-1059 | CGGACGGGCTGAACAGGGTG | 62.1 | −43.7 |
| 63 | ER1-1061 | GTCGGACGGGCTGAACAGGG | 61.2 | −43.4 |
| 64 | ER1-1106 | AAACTCTTCCTGATCGGCGA | 53.8 | −39.7 |
| 65 | ER1-1148 | GCGGATGCTGTCGTCTTTCT | 54.3 | −39.4 |
| 66 | ER1-1155 | GCTGCTTGCGGATGCTGTCG | 61.3 | −43.0 |
| 67 | ER1-1166 | GGCTTTCACACGCTGCTTGC | 58.2 | −41.4 |
| 68 | ER1-1173 | GCTCAACGGCTTTCACACGC | 58.0 | −41.3 |
| 69 | ER1-1212 | GACCGGTAGACGCACGTTCC | 56.7 | −40.8 |
| 70 | ER1-1255 | GGGCTATGGGTATTGCAGTG | 52.1 | −38.7 |
| 71 | ER1-1259 | AAACGGGCTATGGGTATTGC | 53.3 | −40.7 |
| 72 | ER1-1265 | CGGATCAAACGGGCTATGGG | 58.7 | −43.4 |
| 73 | ER1-1311 | GGGCTATCTCCAGGCACAGG | 55.9 | −40.7 |
| 74 | ER1-1315 | GGCAGGGCTATCTCCAGGCA | 58.7 | −42.5 |
| 75 | ER1-1320 | TGGTCGGCAGGGCTATCTCC | 58.6 | −42.4 |
| 76 | ER1-1326 | GCGGTTTGGTCGGCAGGGCT | 64.9 | −47.0 |
| 77 | ER1-1330 | TTCAGCGGTTTGGTCGGCAG | 60.5 | −43.1 |
| 78 | ER1-1336 | ACGTCGTTCAGCGGTTTGGT | 56.8 | −40.9 |
| 79 | ER1-1356 | TTTCACCGTTCTCGTCGTTG | 53.5 | −38.5 |
| 80 | ER1-1364 | CAGCGCGATTTCACCGTTCT | 57.5 | −41.7 |
| 81 | ER1-1370 | CGTACACAGCGCGATTTCAC | 54.2 | −38.9 |
| 82 | ER1-1379 | AGCAGACAGCGTACACAGCG | 54.0 | −38.2 |
| 83 | ER1-1388 | CAGGTTGAAAGCAGACAGCG | 53.4 | −38.4 |
| 84 | ER1-1397 | AATTGCGCCCAGGTTGAAAG | 56.5 | −41.9 |
| 85 | ER1-1407 | CCAGGTTATTAATTGCGCCC | 53.8 | −41.3 |
| 86 | ER1-1428 | TTGCCAGCTCTTCCAGTTCA | 53.3 | −38.2 |
| 87 | ER1-1438 | ACCGCCAGAATTGCCAGCTC | 58.8 | −42.5 |
| 88 | ER1-1451 | GTCAAGTGCACGAACCGCCA | 59.1 | −41.0 |
| 89 | ER1-1463 | ATCCAGCAGCCGCTCAAGTG | 58.5 | −41.2 |
| 90 | ER1-1468 | TGATAATCCAGCAGCGCGTC | 56.1 | −40.4 |
| 91 | ER1-1535 | GATCACACCAATACCCAGCG | 52.6 | −38.1 |
| 92 | ER1-1561 | TCGTTCGCCAGGTAGTAAGC | 52.2 | −39.0 |
| 93 | ER1-1570 | CGTTTACCGTCGTTCGCCAG | 57.9 | −42.2 |
| 94 | ER1-1584 | TGCCGTCGGAGTAGCGTTTA | 55.8 | −41.0 |
| 95 | ER1-1605 | TATGCGTCAGGTTGTTGGCG | 56.8 | −40.5 |
| 96 | ER1-1614 | CGAAGGTTTTATGCGTCAGG | 52.5 | −39.3 |
| 97 | ER1-1688 | GTTAAACCACGGGCACGCGC | 62.0 | −45.0 |
| 98 | ER1-1705 | TTCGCGTAAGTGGTTTCGTT | 52.6 | −39.3 |
| 99 | ER1-1731 | TATAGGTATCGATCGGCAGG | 49.5 | −38.0 |
| 100 | ER1-1777 | CAGTCGTAATGCAGCGGCTC | 55.8 | −40.2 |
| 101 | ER1-1789 | CGCAGAGCTTCCCAGTCGTA | 55.4 | −40.0 |
| 102 | ER1-1839 | TCAGAGCAGAAAGCGTGGAG | 53.0 | −38.1 |
| 103 | ER1-1849 | TCGGACGGCATCAGAGCAGA | 58.9 | −40.9 |
| 104 | ER1-1874 | GGCGTTAGAGATCTGCGAAG | 51.8 | −38.7 |
| 105 | ER1-1916 | TTTGATGCTGACGTAACCGC | 53.7 | −39.0 |
| 106 | ER1-1923 | TCGACGCTTTGATGCTGACG | 57.1 | −40.2 |
| 107 | ER1-1944 | CCTGGCGCAAAATACCGTCT | 56.5 | −42.0 |

TABLE 1-continued

Antisense oligonucleotides that target the *Escherichia coli* K12 ribonucleotide reductase large subunit (R1)

| SEQ ID No.: | Name | Sequence 5'→3' | Tm (° C.) | ΔG (kcal/mol) |
|---|---|---|---|---|
| 108 | ER1-1957 | TAGTCCGGCACCACCTGGCG | 62.5 | −44.2 |
| 109 | ER1-1968 | GCAGGTGCTCGTAGTCCGGC | 59.3 | −42.4 |
| 110 | ER1-1974 | CGTCGTGCAGGTGCTCGTAG | 56.7 | −39.9 |
| 111 | ER1-1983 | GCTCATAGGCGTCGTGCAGG | 58.0 | −41.4 |
| 112 | ER1-1992 | CCCACAGCAGCTCATAGGCG | 58.0 | −41.5 |
| 113 | ER1-2000 | CGGCATTTCCCACAGCAGCT | 59.7 | −42.8 |
| 114 | ER1-2010 | CATCGTTACCCGGCATTTCC | 56.5 | −41.9 |
| 115 | ER1-2083 | GGATCGTAGTTGGTGTTGGC | 51.8 | −39.9 |
| 116 | ER1-2112 | TCGGCACTTTTCCTGACGGG | 59.5 | −42.8 |
| 117 | ER1-2145 | AGGCGGTGAGCAGGTCTTTC | 55.7 | −40.5 |
| 118 | ER1-2154 | CGAATTTGTAGGCGGTGAGC | 54.8 | −40.5 |
| 119 | ER1-2166 | GTGTTTTGACCCCGAATTTG | 51.9 | −38.6 |
| 120 | ER1-2211 | CGTCTTGTGCGTCTTCAGCG | 56.8 | −40.0 |
| 121 | ER1-2262 | TCTTACATGCGCCGCTTTCG | 58.6 | −42.8 |

TABLE 2

Antisense oligonucleotides that target the *Escherichia coli* K12 ribonucleotide reductase small subunit (R2)

| SEQ ID No.: | Name | Sequence 5'→3' | Tm (° C.) | ΔG (kcal/mol) |
|---|---|---|---|---|
| 122 | ER2-50 | CGGCTGACCAAAGAACATCG | 55.5 | −40.0 |
| 123 | ER2-60 | CCACGTTGACCGGCTGACCA | 61.2 | −42.2 |
| 124 | ER2-67 | TAGCGAGCCACGTTGACCGG | 60.6 | −43.2 |
| 125 | ER2-134 | CGGACGCCAGAAGAAAGAGA | 54.4 | −39.8 |
| 126 | ER2-144 | CAACTTCTTCCGGACGCCAG | 57.0 | −41.3 |
| 127 | ER2-168 | AATCTATACGGTCGCGGGAG | 53.4 | −40.5 |
| 128 | ER2-198 | TGTGTTTTTCGTGCTCCGGC | 58.3 | −41.6 |
| 129 | ER2-273 | GCAATAGCGCCACGTTCGGG | 62.1 | −45.2 |
| 130 | ER2-284 | AGAAATAAGCGGCAATAGCG | 51.8 | −40.3 |
| 131 | ER2-290 | CGGAATAGAAATAAGCGGCA | 52.4 | −40.3 |
| 132 | ER2-307 | ACCCAGGTTTCCAGTTCCGG | 57.4 | −42.0 |
| 133 | ER2-350 | ATAGGAACGGGAATGAATCG | 50.7 | −38.8 |
| 134 | ER2-441 | TCCCTTCCGCACGTTCTGG | 59.5 | −42.8 |
| 135 | ER2-498 | CGCCCAGCAGATGCCAGTAG | 58.0 | −41.5 |
| 136 | ER2-505 | GTACCTTCGCCCAGCAGATG | 54.6 | −39.7 |
| 137 | ER2-544 | CGCAGGCTAACGGTCACAGT | 55.2 | −39.7 |
| 138 | ER2-557 | TTTCTTCAGCTCGCGCAGGC | 60.2 | −43.4 |
| 139 | ER2-640 | GCAAATGCGAAGGAACAAGC | 54.9 | −40.4 |
| 140 | ER2-655 | ATCAATTCGCGTTCTGCAAA | 53.4 | −39.3 |
| 141 | ER2-680 | GCGAATAATTTTGGCGTTGC | 54.9 | −41.6 |
| 142 | ER2-692 | GCGGGCAATCAGGCGAATAA | 59.5 | −44.0 |
| 143 | ER2-704 | CAGGGCTTCGTCGCGGGCAA | 66.8 | −47.8 |
| 144 | ER2-714 | CGGTCAGGTGCAGGGCTTCG | 62.3 | −44.0 |
| 145 | ER2-724 | TGCTGGGTGCCGGTCAGGTG | 63.6 | −43.5 |
| 146 | ER2-728 | CATATGCTGGGTGCCGGTCA | 58.8 | −41.4 |
| 147 | ER2-778 | GCAATTTCCGCCATCTCAGG | 56.8 | −41.5 |
| 148 | ER2-796 | TCCTGCTTACACTCTTCGGC | 52.1 | −38.3 |
| 149 | ER2-848 | ATCCGCCCAGTCTTTCTCCT | 54.2 | −40.4 |
| 150 | ER2-857 | GAACAGATAATCCGCCCAGT | 50.7 | −38.1 |
| 151 | ER2-976 | GGGTTGGAGCGCGTCTGGAA | 61.8 | −44.0 |
| 152 | ER2-983 | CGGGATCGGGTTGGAGCCG | 68.1 | −49.1 |
| 153 | ER2-985 | CACGGGATCGGGTTGGAGCG | 64.0 | −45.6 |
| 154 | ER2-1045 | CTGACTTCCACTTCCTGCGG | 54.6 | −39.9 |
| 155 | ER2-1063 | TGCCCGACCAGATAAGAACT | 51.3 | −38.2 |
| 156 | ER2-1076 | TTCCGAGTCAATCTGCCCGA | 57.8 | −41.2 |
| 157 | ER2-1092 | AATCGTCGGTGTCCACTTCC | 53.6 | −38.8 |

TABLE 3

Antisense Sequences that Target *Escherichia coli* SecA

| SEQ ID No.: | Name | Sequence 5'→3' | Tm (° C.) | ΔG (kcal/mol) |
|---|---|---|---|---|
| 158 | ES56 | GACCACTTTGCGCATCCGGC | 62.1 | −44.2 |
| 159 | ES62 | GATGTTGACCACTTTGCGCA | 54.3 | −38.3 |
| 160 | ES85 | ATCTCCGGTTCCATGGCATT | 55.5 | −40.8 |
| 161 | ES92 | TTTTTCCATCTCCGGTTCCA | 54.3 | −40.1 |
| 162 | ES116 | CCCTTTCAGTTCTTCGTCGG | 53.8 | −39.8 |
| 163 | ES124 | GCGGTTTTCCCTTTCAGTTC | 52.9 | −39.9 |
| 164 | ES129 | ACTCTGCGGTTTTCCCTTTC | 52.5 | −39.6 |
| 165 | ES153 | CGCCTTTTTCCAGACGTGCA | 58.4 | −41.9 |
| 166 | ES158 | CACTTCGCCTTTTCCAGAC | 51.5 | −38.4 |
| 167 | ES165 | TTTCCAGCACTTCGCCTTTT | 54.1 | −40.5 |
| 168 | ES170 | CAGATTTTCCAGCACTTCGC | 52.5 | −38.6 |
| 169 | ES206 | ACTTGCCTCACGTACCACGG | 54.9 | −39.5 |
| 170 | ES215 | GACGCGCTTACTTGCCTCAC | 55.0 | −40.1 |
| 171 | ES230 | GTGACGCATACCAAAGACGC | 53.1 | −38.5 |
| 172 | ES264 | TAAGAACCATACCGCCGAGT | 51.5 | −39.1 |
| 173 | ES286 | ATTTCGGCGATGCAGCGTTC | 59.7 | −43.4 |
| 174 | ES303 | TTCCTTCACCGGTACGCATT | 54.5 | −40.3 |
| 175 | ES307 | GTTTTTCCTTCACCGGTACG | 51.4 | −38.9 |
| 176 | ES320 | CGTTGCGGTCAGGGTTTTC | 56.8 | −41.6 |
| 177 | ES336 | TCAGGTAAGCAGGCAGCGTT | 55.0 | −40.2 |
| 178 | ES351 | TACCGGTTAGTGCGTTCAGG | 52.8 | −39.2 |
| 179 | ES392 | TTGCGCCAGGTAGTCGTTGA | 56.5 | −40.4 |
| 180 | ES398 | GTCACGTTGCGCCAGGTAGT | 55.0 | −39.5 |
| 181 | ES418 | AGCGGACGGTTGTTTTCGGC | 60.8 | −44.5 |
| 182 | ES429 | GGAATTCAAACAGCGGACGG | 56.7 | −41.5 |
| 183 | ES436 | AGGCCAAGGAATTCAAACAG | 51.0 | −38.4 |
| 184 | ES448 | ATACCGACAGTCAGGCCAAG | 51.6 | −38.0 |
| 185 | ES485 | TTCGCGCTTTGCCGGTGCTG | 65.8 | −46.9 |
| 186 | ES531 | AGCCGTATTCGTTGTTCGTA | 50.1 | −37.9 |
| 187 | ES544 | CGCAGGTAGTCAAAGCCGTA | 53.1 | −39.5 |
| 188 | ES553 | ATGTTGTCGCGCAGGTAGTC | 52.6 | −38.1 |
| 189 | ES556 | GCCATGTTGTCGCGCAGGTA | 59.2 | −41.7 |
| 190 | ES617 | GTCCACTTCGTCCACCAGCG | 57.7 | −40.4 |
| 191 | ES646 | GGTGTACGCGCTTCATCGAT | 55.0 | −40.0 |
| 192 | ES647 | CGGTGTACGCGCTTCATCGA | 59.3 | −42.1 |
| 193 | ES695 | GCGTTTATACATTTCCGAGC | 49.5 | −38.4 |
| 194 | ES724 | CGGATCAGGTGCGGAATAAT | 53.9 | −40.4 |
| 195 | ES799 | TTCACCTGCCGAGATTTTTC | 51.8 | −38.6 |
| 196 | ES824 | CAGCACCAGACCACGTTCGG | 58.6 | −40.7 |
| 197 | ES851 | GCCCTCTTTCACCAGCAGTT | 53.3 | −39.1 |
| 198 | ES866 | CCCTTCATCCATGATGCCCT | 55.9 | −40.6 |
| 199 | ES889 | TTGGCCGGAGAGTACAGAGA | 52.2 | −38.1 |
| 200 | ES898 | AGCATGATGTTGGCCGGAGA | 57.6 | −40.9 |
| 201 | ES922 | AGCGCCGCCGTTACGTGGTG | 64.6 | −46.5 |
| 202 | ES950 | GTCACGGGTAAACAGCGCAT | 54.9 | −40.0 |
| 203 | ES1068 | CACCTTCTTTCGCTTCCACA | 52.8 | −38.4 |
| 204 | ES1097 | CAGCGTTTGGTTTTCGTTCT | 52.1 | −38.9 |
| 205 | ES1109 | GGTGATCGAAGCCAGCGTTT | 56.5 | −41.2 |
| 206 | ES1128 | GACGGAAGTAGTTCTGGAAG | 45.5 | −35.0 |
| 207 | ES1147 | CCCGCCAGTTTTTCATACAG | 52.3 | −39.2 |
| 208 | ES1152 | TCATCCCGCCAGTTTTTCA | 57.5 | −41.6 |
| 209 | ES1218 | GAACAACGACGGTATCCAGC | 52.0 | −38.2 |
| 210 | ES1328 | GCCTTTCGCAGTACGTTCTT | 51.4 | −38.9 |
| 211 | ES1350 | TAGTACCCACCAGCACCGGC | 57.1 | −41.4 |
| 212 | ES1398 | CGGCTTTGGTCAGTTCGTTT | 54.3 | −40.1 |
| 213 | ES1410 | TGTGCTTAATACCGGCTTTG | 50.8 | −38.6 |
| 214 | ES1439 | GTTGGCGTGGAATTTGGCGT | 59.3 | −43.0 |
| 215 | ES1462 | GCCTGAGCAACAATCGCCGC | 62.4 | −44.5 |
| 216 | ES1515 | CTGTACCACGACCCGCCATA | 55.6 | −40.3 |
| 217 | ES1518 | TATCTGTACCACGACCCGCC | 54.7 | −40.0 |
| 218 | ES1545 | CTGCCTGCCAGCTACCACCG | 60.2 | −42.9 |
| 219 | ES1563 | TTTCCAGCGCGGCAACTTCT | 59.4 | −43.4 |
| 220 | ES1581 | TTTGCTCTGGTCGGATTT | 57.0 | −41.8 |
| 221 | ES1589 | TTTTTCAATTTGCTCTGCGG | 53.2 | −39.8 |
| 222 | ES1624 | ACCGCATCGTGACGTACCTG | 55.7 | −39.6 |
| 223 | ES1629 | CCAGTACCGCATCGTGACGT | 55.7 | −39.6 |
| 224 | ES1633 | GCTTCCAGTACCGCATCGTG | 55.5 | −40.0 |
| 225 | ES1655 | ACCGATGATATGCAGGCCAC | 54.6 | −39.6 |
| 226 | ES1712 | ACGACCAGAACGACCGCGCA | 63.3 | −44.1 |
| 227 | ES1718 | CCCCTGACGACCAGAACGAC | 56.6 | −40.1 |
| 228 | ES1722 | CATCCCCTGACGACCAGAA | 56.9 | −40.4 |
| 229 | ES1739 | GAAACGGGAAGAACCAGCAT | 53.1 | −39.5 |
| 230 | ES1748 | CGACAGGTAGAAACGGGAAG | 51.4 | −38.6 |

TABLE 3-continued

Antisense Sequences that Target *Escherichia coli* SecA

| SEQ ID No.: | Name | Sequence 5'→3' | Tm (° C.) | ΔG (kcal/mol) |
|---|---|---|---|---|
| 231 | ES1781 | GGAAGCAAAAATACGCATCA | 50.6 | −38.2 |
| 232 | ES1785 | GGTCGGAAGCAAAAATACGC | 53.9 | −40.9 |
| 233 | ES1794 | CGGATACTCGGTCGGAAGCA | 57.3 | −41.7 |
| 234 | ES1814 | ACCCAGTTTACGCATCATGC | 52.5 | −38.5 |
| 235 | ES1845 | ACGGGTGTTCAATGGCTTCG | 57.1 | −41.2 |
| 236 | ES1861 | ATCGCTTTAGTCACCCACGG | 54.1 | −40.0 |
| 237 | ES1888 | CTTTCAACTTTACGCTGGGC | 51.9 | −39.3 |
| 238 | ES1892 | ACGGCTTTCAACTTTACGCT | 51.1 | −39.2 |
| 239 | ES2007 | TGGTTTCGCTCACATCGCTG | 57.0 | −40.0 |
| 240 | ES2054 | GTAGGCATCAATGGTCGCTT | 51.7 | −38.5 |
| 241 | ES2084 | CCACATTTCTTCCAGCGACT | 51.7 | −38.0 |
| 242 | ES2087 | ATCCCACATTTCTTCCAGCG | 53.9 | −39.7 |
| 243 | ES2191 | TCACGCAGCGTCTCTTCATG | 54.7 | −38.2 |
| 244 | ES2275 | CCTTTCTCGAAGTGACGCAT | 51.9 | −38.2 |
| 245 | ES2306 | CCACAGGGAGTCAAGCGTTT | 54.1 | −39.3 |
| 246 | ES2325 | TCGCTGCCAGGTGCTCTTTC | 57.7 | −41.1 |
| 247 | ES2330 | GTCCATCGCTGCCAGGTGCT | 59.7 | −41.9 |
| 248 | ES2339 | ACGCAGATAGTCCATCGCTG | 52.7 | −38.4 |
| 249 | ES2381 | CTTCGGATCTTTCTGTGCGT | 51.9 | −38.2 |
| 250 | ES2395 | CGTTTGTATTCCTGCTTCGG | 52.5 | −39.4 |
| 251 | ES2422 | ATCGCTGCAAACATGGAGAA | 53.1 | −38.5 |
| 252 | ES2520 | CCATACGACGCTGTTGTTCC | 52.9 | −38.5 |
| 253 | ES2525 | GGCTTCCATACGACGCTGTT | 54.2 | −40.0 |
| 254 | ES2537 | CGCTAAACGCTCGGCTTCCA | 59.9 | −44.1 |
| 255 | ES2555 | GCTAAGCTGCTGCATTTGCG | 56.2 | −41.3 |
| 256 | ES2619 | CTACTTTGCGCTCTCCGGTT | 53.8 | −40.4 |
| 257 | ES2626 | TTACGTCCTACTTTGCGCTC | 50.0 | −38.0 |
| 258 | ES2646 | AACCGCACGGGCAAGGATCG | 63.6 | −45.9 |
| 259 | ES2651 | ACCAGAACCGCACGGGCAAG | 61.7 | −44.0 |
| 260 | ES2656 | TTTTTACCAGAACCGCACGG | 55.1 | −41.0 |

TABLE 4

Antisense Sequences that Target *E. coli* SecA based on Conserved Sequences

| SEQ ID No.: | Name | Sequence 5'→3' | Tm (° C.) | ΔG (kcal/mol) |
|---|---|---|---|---|
| 261 | ES386 | CAGGTAGTCGTTGACGGTAA | 47.7 | −35.7 |
| 262 | ES388 | CAGGTAGTCGTTGACGGT | 45.0 | −32.9 |
| 263 | ES1126 | CGGAAGTAGTTCTGGAAGGT | 47.6 | −36.5 |
| 264 | ES1702 | CGACCGCGCAACTGGTTATC | 57.8 | −41.9 |
| 265 | ES2644 | CCGCACGGGCAAGGATCGTT | 63.6 | −45.9 |

In Tables 1, 2, 3, and 4, the "Tm" is the melting temperature of an oligonucleotide duplex calculated according to the nearest-neighbor thermodynamic values. At this temperature 50% of nucleic acid molecules are in duplex and 50% are denatured. The "ΔG" is the free energy of the oligonucleotide, which is a measurement of an oligonucleotide duplex stability.

The following sequences have been determined to be conserved among species:

ES386 [SEQ ID NO:261] is conserved among *Escherichia coli* and *Mycobacterium tuberculosis*;

ES388 [SEQ ID NO:262] is conserved among *Escherichia coli; Mycobacterium tuberculosis*; and *Mycobacterium bovis*;

ES553 [SEQ ID NO:188] is conserved among *Escherichia coli, Mycobacterium tuberculosis, Mycobacterium bovis, Streptomyces coelicolor*; and *Streptomyces lividans*;

ES556 [SEQ ID NO:189] is conserved among *Escherichia coli, Mycobacterium tuberculosis, Mycobacterium bovis, Streptomyces coelicolor*; and *Streptomyces lividans*; and *Synechoccus sp.*; and ES646 [SEQ ID NO:191] is conserved among *Escherichia coli* and *Staphylococcus carnosus*;

ES1126 [SEQ ID NO:263] is conserved among *Escherichia coli* and *Rhodobacter capsulatus* SecA genes.

ES2644 [SEQ ID NO:265] is conserved among *Escherichia coli* SecA gene, MutA (A:T to C:G transversion), and tyrosine-specific transport protein (tyrP) gene.

The term "alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, and the like.

The term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "halo" or "halogen" refers to fluoro, chloro, bromo and iodo and preferably is either fluoro or chloro.

The term "thiol" refers to the grou —SH.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically acceptable salt" refers to salts which retain the biological effectiveness and properties of the antisense oligonucleotides of this invention and which are not biologically or otherwise undesirable. In many cases, the antisense oligonucleotides of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "ribonucleotide reductase gene" or the "ribonucleoside diphosphate reductase gene" refers to any gene which encodes a protein that either reduces the four main ribonucleotides to the corresponding deoxyribonucleotides involved in DNA synthesis or encodes a subunit of a multimeric enzyme which reduces the four main ribonucleotides to the corresponding deoxyribonucleotides. Without being limiting, examples of ribonucleotide reductase genes from bacteria include the *E. coli* nrdA, nrdB and nrd D genes; the *S. typhimurium* nrdE and nrdF genes; and the *Lactococcus lactis* nrdEF gene. Examples of the ribonucleotide reductase genes from viruses include the herpes simplex type 1 and 2 ribonucleotide reductases and the bovine and equine herpes simplex ribonucleotide reductases.

The term "secA" refers to an oligonucleotide sequence which encodes a protein having similar properties as those expressed by the *E. coli* secA gene. Without being limiting, examples of secA genes from bacteria include the *Mycobacterium bovis* secA gene; the *Mycobacterium tuberculosis* secA gene, the *Staphylococcus aureus* secA gene and the *Staphylococcus carnosus* secA gene.

The term "microorganism" means a bacteria, fungi or virus having either a ribonucleotide reductase or secA gene. Specifically excluded from this definition is the material parasite, plasmodium.

The term "bacteria" refers to any bacteria encoding either a ribonucleotide reductase gene or a secA gene, including *Escherichi coli, Mycobacterium tuberculosis, Mycobacterium bovis, Mycobacterium smegmatis, Salmonella typhimurium, Thermoplasma acidophilum, Pyrococcusfuriosus, Bacillus subtilis, Bacillus firmus, Lactococcus lactis, Staphylococcus aureus, Staphylococcus carnosus, Listeria monocytogenes, Borrelia burgdorferi, P. sativum, S. griseus*, and Synechoccus sp.

The term "virus" refers to any virus having a ribonucleotide reductase gene. Preferably the virus will be a DNA virus. Examples of suitable viruses include various herpes viruses (such as herpes simplex types 1 and 2, varicella-herpes zoster, cytomegalovirus and Epstein-Barr virus) and the various hepatitis viruses.

The term "complementary to" means that the antisense oligonucleotide sequence is capable of binding to the target sequence, ie the ribonucleotide reductase gene or the secA gene. Preferably the antisense oligonucleotide sequence has at least about 75% identity with the target sequence, preferably at least about 90% identity and most preferably at least about 95% identity with the target sequence allowing for gaps or mismatches of several bases. Identity can be determined, for example, by using the BLASTN program of the University of Wisconsin Computer Group (GCG) software.

The term "inhibiting growth" means a reduction in the growth of the bacteria or viruses of at least 25%, more preferably of at least 50% and most preferably of at least 75%. The reduction in growth can be determined for bacteria by a measuring the optical density of a liquid bacteria culture with a spectrophotometer or by counting the number of colony forming units/ml (CFU/ml) upon plating on culture plates. The reduction in growth can be determined for viruses by measuring the number of plaque forming units/ml upon plating on susceptible cells.

Preparation of the Antisense Oligonucleotides

The antisense oligonucleotides of the present invention may be prepared by conventional and well-known techniques. For example, the oligonucleotides may be prepared using solid-phase synthesis and in particular using commercially available equipment such as the equipment available from Applied Biosystems Canada Inc., Mississauga, Canada. The oligonucleotides may also be prepared by enzymatic digestion of the naturally occurring ribonucleotide reductase or secA gene by methods known in the art.

Isolation and Purification of the Antisense Oligonucleotides

Isolation and purification of the antisense oligonucleotides described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. However, other equivalent separation or isolation procedures could, of course, also be used.

The invention contemplates a method of evaluating if an antisense oligonucleotide inhibits the growth of a microbe having a ribonucleotide reductase or secA gene. The method comprises selecting the microbe/microorganism having a ribonucleotide reductase or secA gene, administering the antisense oligonucleotide; and comparing the growth of the treated microbe with the growth of an untreated microorganism.

In order for the antisense oligonucleotide to effectively interrupt the expression of the ribonucleotide reductase or secA gene, the antisense oligonucleotide enters the microorganism's cell, in the case of fungal or bacterial cells or enter the mammalian cell having the virus target.

Although oligonucleotides are taken up by bacterial cells, some modification of the oligonucleotides may help facilitate or regulate said uptake. Thus, a carier molecule, for example an amino acid, can be linked to the oligonucleotide. For example, bacteria have multiple transport systems for the recognition and uptake of molecules of leucine. The addition of this amino acid to the oligonucleotide may facilitate the uptake of the oligonucleotide in the bacteria and not substantially interfere with the activity of the antisense oligonucleotide in the bacterial cell.

Other methods are contemplated for facilitating the uptake of the antisense oligonucleotide into bacteria. For example, the addition of other amino acids or peptides or primary amines to the 3' or 5' termini of the antisense oligonucleotide may enable utilization of specific transport systems. Addition of lactose to the oligonucleotide by a covalent linkage may also be used to enable transport of the antisense oligonucleotide by lactose permease. Other sugar transport systems are also known to be functional in bacteria and can be utilized in this invention.

With regard to inhibiting the expression of ribonucleotide reductase in DNA viruses, the antisense oligonucleotide is preferably introduced into the cell infected with the DNA virus. The antisense oligonucleotides may be delivered using vectors or liposomes.

An expression vector comprising the antisense oligonucleotide sequence may be constructed having regard to the sequence of the oligonucleotide and using procedures known in the art. The vectors may be selected from plasmids or benign viral vectors depending on the eukaryotic cell and the DNA virus. Phagemids are a specific example of beneficial vectors because they can be used either as plasmids or a bacteriophage vectors. Examples of other vectors include viruses such as bacteriiophages, baculoviruses and retroviruses, DNA viruses, liposomes and other recombination vectors.

Vectors can be constructed by those skilled in the art to contain all the expression elements required to achieve the desired transcription of the antisense oligonucleotide sequences. Therefore, the invention provides vectors comprising a transcription control sequence operatively linked to a sequence which encodes an antisense oligonucleotide. Suitable transcription and translation elements may be derived from a variety of sources, including bacterial, fungal, viral, mammalian or insect genes. Selection of appropriate elements is dependent on the host cell chosen.

Reporter genes may be included in the vector. Suitable reporter genes include β-galactosidase (e.g. lacZ), chloramphenicol, acetyl-transferase, firefly luciferase, or an immunoglobulin or portion thereof. Transcription of the antisense oligonucleotide may be monitored by monitoring for the expression of the reporter gene.

The vectors can be introduced into cells or tissues by any one of a variety of known methods within the art. Such methods can be found generally described in Sambrook et al.[18]; Ausubel et al.[19]; Chang et al.[20]; Vega et al.[21]; and Vectors: A Survey of Molecular Cloning Vectors and Their Uses[22] and include, for example, stable or transient transfection, lipofection, electroporation and infection with recombinant viral vectors.

Introduction of nucleic acids by infection offers several advantages. Higher efficiency and specificity for tissue type can be obtained. Viruses typically infect and propagate in specific cell types. Thus, the virus' specificity may be used to target the vector to specific cell types in vivo or within a tissue or mixed culture of cells. Viral vectors can also be modified with specific receptors or ligands to alter target specificity through receptor mediated events.

Pharmaceutical Formulations

When employed as pharmaceuticals, the antisense oligonucleotides are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the antisense oligonucleotides associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the antisense oligonucleotide is employed at no more than about 20 weight percent of the pharmaceutical composition, more preferably no more than about 15 weight percent, with the balance being pharmaceutically inert carrier(s).

The antisense oligonucleotide is effective over a wide dosage range and is generally administered in a pharmaceutically effective amount. It, will be understood, however, that the amount of the antisense oligonucleotide actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient/antisense oligonucleotide is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A formulation may be prepared as follows:

| Ingredient | Quantity |
|---|---|
| Active Ingredient | 5.0 mg |
| Corn Oil | 1.0 mL |

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the antisense oligonucleotides of the present invention in controlled amounts. The construction and use of transdermal patches for the delivery of pharmaceutical agents is well known in the art. See, for example, U.S. Pat. No. 5,023,252[23], herein incorporated by reference. Such patches may be constructed for continuous, pulsatile, or on demand delivery of pharmaceutical agents.

Another preferred method of delivery involves "shotgun" delivery of the naked antisense oligonucleotides across the dermal layer. The delivery of "naked" antisense oligonucleotides is well known in the art. See, for example, Felgner et al., U.S. Pat. No. 5,580,859[24]. It is contemplated that the antisense oligonucleotides may be packaged in a lipid vesicle before "shotgun" delivery of the antisense oligonucleotide.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472[25] which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*[6].

The antisense oligonucleotides or the pharmaceutical composition comprising the antisense oligonucleotides may be packaged into convenient kits providing the necessary materials packaged into suitable containers.

Utility

The antisense oligonucleotides of the present invention may be used for a variety of purposes. They may be used to inhibit the expression of the ribonucleotide reductase gene in a microorganism, resulting in the inhibition of growth of that microorganism. They may be used to inhibit the expression of the secA gene in a microorganism, resulting in the inhibition of growth of that microorganism. The oligonucleotides may be used as hybridization probes to detect the presence of the ribonucleotide reductase gene or the secA gene in the microorganism. When so used the oligonucleotides may be labeled with a suitable detectable group (a radioisotope, a ligand, another member of a specific binding pair, for example, biotin). The oligonucleotides may also be used to determine the presence of a particular microorganism in a biological sample. Finally, the oligonucleotides may be used as molecular wight markers.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

μM=micromolar
mM=millimolar
M=molar
ml=milliliter
μl=microliter
mg=milligram
μg=microgram
IPTG=isopropyl-β-D-thiogalactoside
PAGE=polyacrylamide gel electrophoresis
PVDF=polyvinylidene difluoride
rpm=revolutions per minute
OD=optical density
CFU=colony forming units
ΔG=free energy, a measurement of oligonucleotide duplex stability
kcal=kilocalories General Methods in Molecular Biology Standard molecular biology techniques known in the art and not specifically described were generally followed as in Sambrook et al.[18]; Ausubel et al.[19]; and Perbal[27].

The antisense oligonucleotides in Tables 1, 2 and 3 were selected from the sequence complementary to the ribonucleotide reductase or secA genes of *E. coli* such that the sequence exhibited the least likelihood of showing one or more of duplex formation, hair-pin formation, and homooligomer/sequence repeats but had a high to moderate potential to bind to the ribonucleotide reductase gene or the secA gene sequence. These properties were determined using the computer modeling program OLIGO Primer Analysis Software, Version 5.0 (distributed by National Biosciences, Inc., Plymouth, Minn.).

The antisense oligonucleotides in Table 4 were selected on the basis that the sequence is highly conserved for the secA genes between two or more microbial species. This property was determined using the BLASTN program (Altschul, et al.[16]) of the University of Wisconsin Computer group (GCG) software (Devereux J. et al.[17]) with the National Center for Biotechnology Information (NCBI) databases.

Phosphorothioate oligonucleotides comprising the desired sequences were specially ordered either from Boston BioSystems, Bedford Mass.; Canadian Life Technologies, Burlington, Canada; Dalton Chemical Laboratories, Inc., North York, Canada; Hybridon, Inc., Milford Mass.; Oligos Etc., or Oligos Therapeutics, Inc., Wilsonvill Oreg.; or TriLink Bio Technologies, San Diego, Calif. Antisense oligonucleotides may also be made by methods known in the art.

Polymerase chain reaction (PCR) was carried out generally as in *PCR Protocols: A Guide To Methods And Applications*[28].

Example 1

Inhibition of Mouse Ribonucleotide Reductase Small Subunit (R2) Expression in *Escherichia coli* by Antisense Oligonucleotide AS-II-626-20

Competent BL21 (DE3) cells carrying a plasmid containing the mouse ribonucleotide reductase R2 gene were used. (Mann et al.[34]) The antisense oligonucleotide, AS-II-626-20, GGCTAAATCGCTCCACCAAG [SEQ ID NO:266] is specifically complementary to the mouse ribonucleotide reductase R2 gene. Approximately $10^{10}$ bacteria/ml were electroporated using a Cell Porator (Gibco BRL, Burlington, Canada) in micro electro-chambers (0.4 cm between the electrodes) at a pulse of 2.4 kV, 4 kΩ with either 20 μM or 200 μM of antisense oligonucleotide AS-II-626-20, following methods described by the manufacturer (Dower W. J.[29]; Neuman et; and Taketo, A.[31]). Control populations were subjected to electroporation but without the antisense oligonucleotide AS-II-626-20.

The bacterial cells were then transferred to Luria-Bertani broth (Miller J. H.[32]) containing 50 μg/ml of ampicillin and 0.4 mM of isopropyl β-D-thiogalactoside (IPTG) (expression inducer) (Horwitz J. P.[33]) to grow at 30° C. on a shaker at 250 rotations per minute (rpm) for 5 hours.

The cells were harvested by centrifugation and treated with 2×sample loading buffer (100 mM Tris

[hydroxymethyl'aminomethane, pH 6.8, 200 mM dithiothrietol, 4% sodium dodecyl sulfate, 20% glycerol and 0.015% bromophenol blue) and sonicated (Olsvik, et al.[35]) for 15 seconds. The supernatants were resolved by polyacrylamide gel electrophoresis (PAGE) (Laemmli U.K.[36]).

The ribonucleotide reductase R2 expression was detected by Western blot. The protein gel was blotted onto polyvinylidene difuoride (PVDF) protein sequencing membrane. (Choy et al.[37]). The presence of the mouse ribonucleotide reductase was detected with a rabbit anti-mouse R2 subunit antibody (Chan et al.[39]). The presence of the antibody bound to the ribonucleotide reducatase was detected using a second goat anti-rabbit immunoglobulin linked with horseradish peroxidase (Amersham Life Sciences, Oakville Canada).

Figure 14:
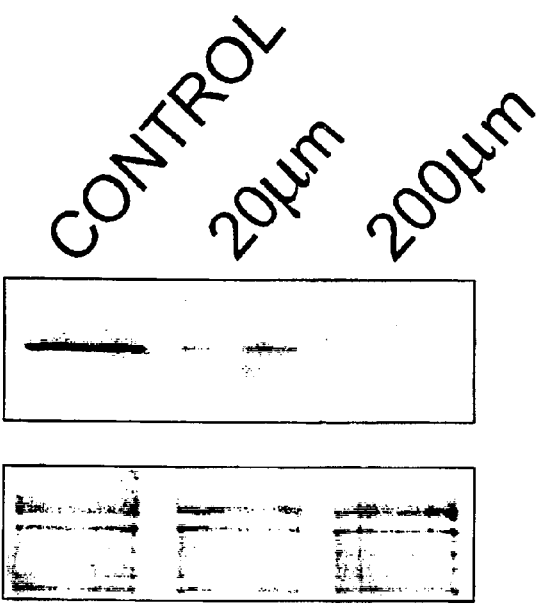
FIG. 14 is a photograph of a Western blot of a polyacrylamide gel of the cellular protein from *E. coli* cells carrying a plasmid containing the mouse ribonucleotide reductase R2 gene after treatment with either 20 $\mu$M or 200 $\mu$M of oligonucleotide AS-II-626-20.

The upper panel of FIG. 14 is a photograph of the Western Blot results. The lower panel of FIG. 14 is a photograph of the membrane stained with India ink to indicate the level of protein loaded in each lane.

It is clear that administration of either 20 µM or 200 µM AS-II-626-20 resulted in a marked reduction of mouse ribonucleotide reductase gene expression in the E. coli cells.

Example 2

Inhibition of Bacteria Escherichia coli K12 Growth by Antisense Oligonucleotides ER1-169 and ER2-724 Targeting E. coli Ribonucleotide Reductase Large Subunit (R1) and Small Subunit (R2)

E. coli cells were electroporated by the method set forth in Example 1 with ER1-169 [SEQ ID NO:22] or ER2-724 [SEQ ID NO:145] at the concentrations shown in FIG. 15, while the control cells received oligonucleotide AS-II-626-20 [SEQ ID NO:266] (targeting mouse ribonucleotide reductase small subunit).

The E. coli cells were then transferred to fresh Luria-Bertani broth (Miller J. H.[32]) to grow at 30° C. on a shaker at 250 rpm for 3 hours. The flasks for the test and the control each contained the same number of bacteria per ml at the start of the experiment. The optical density at 590 nm ($OD_{590}$) of the cultures was measured at the start and at the end of the 3 hours. The inhibition of E. coli growth was calculated by comparing the increase in $OD_{590}$ values at the start and the end of the 3 hours of the oligonucleotide-treated cultures to the increase of the control cultures at the start and at the end of the 3 hours. (Carpentier P.L.[40])

The results indicate that ER1-169 [SEQ ID NO:22] and ER2-724 [SEQ ID NO:145] inhibited the growth of E. coli.

Example 3

Killing of Escherichia coli K12 by Antisense Oligonucleotides Targeting the Ribonucleotide Reductase Large Subunit (R1) or the Small Subunit (R2)

E. coli cells (approximately $2 \times 10^9$ were incubated with 20 µM of each of the phosphorothioate oligonucleotides set forth in FIG. 12 on ice for 45 minutes. A control without oligonucleotides was also incubated for each experiment. Cells were heat shocked by placing them in a 42° C. bath for 45 seconds. (Sambrook J. et al.[18])

Luria-Bertani (LB) broth (Miller J. H.[32]) was added and the samples were incubated at room temperature for 30 minutes. Dilutions of treated and untreated bacteria were incubated overnight at 37° C. on culture plates containing LB medium, and the number of colonies was counted.

Figure 16:
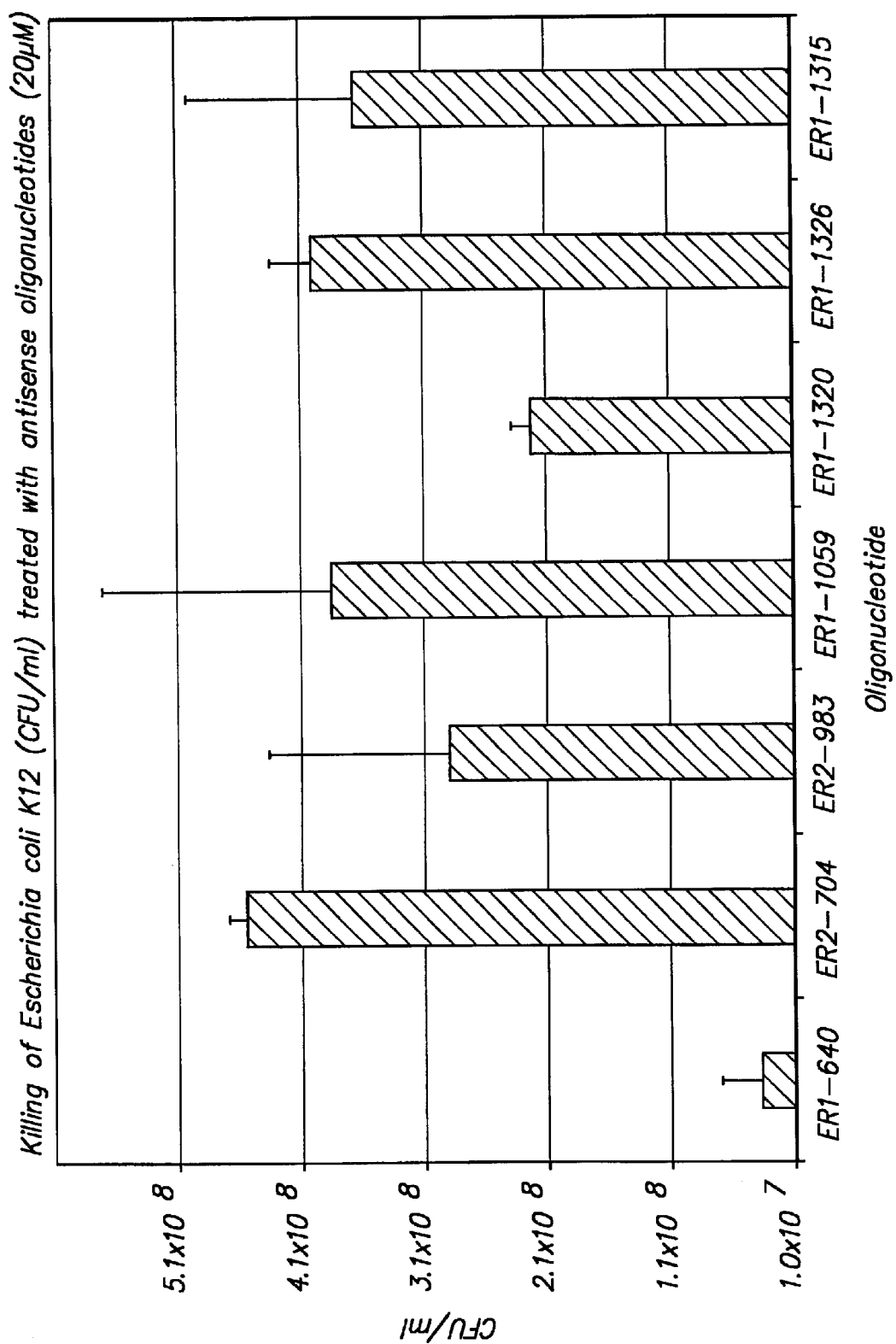
FIG. 16 is a graph of the number of colony forming units/ml of *E. coli* cells after treatment with ribonucleotide reductase antisense oligonucleotides.

The number of killed bacteria was calculated by subtracting the surviving colony forming units (CFU/ml) of the oligonucleotide-treated bacteria from the CFU/ml of the control. FIG. 16 shows the number of bacteria killed by treatment with the antisense sequences: ER1-640 [SEQ ID NO:43]; ER1-1059 [SEQ ID NO:62]; ER1-1320 [SEQ ID NO:75]; ER1-1315 [SEQ ID NO:74]; ER1-1326 [SEQ ID NO:76]; ER2-704 [SEQ ID NO:143] and ER2-983 [SEQ ID NO:152].

The results from FIG. 16 show that antisense oligonucleotides complementary to either the R1 or R2 subunit of ribonucleotide reductase are effective as anti-bacterial agents.

Example 4

Figure 17:
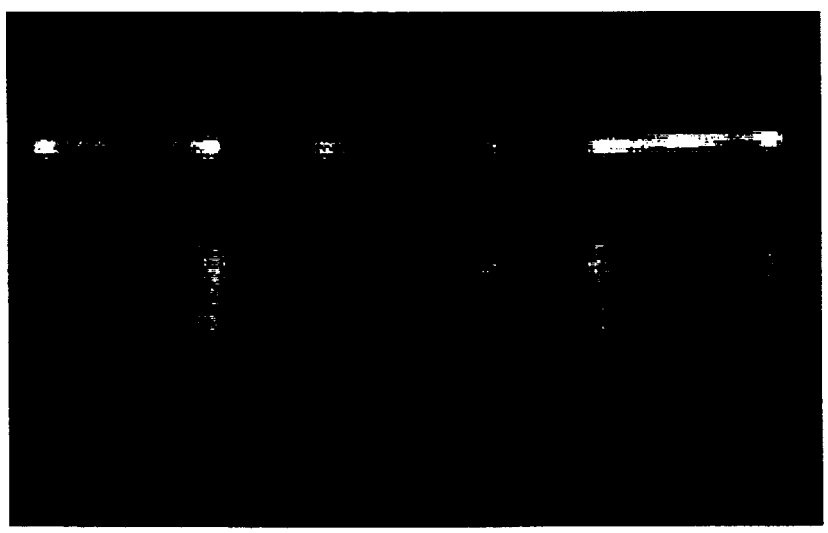
FIG. 17 is a photograph of a Western blot of a polyacrylamide gel of cellular protein from *E. coli* cells after treatment with secA antisense oligonucleotides.

Inhibition of the secA Protein Expression in Escherichia coli Following Treatment with Antisense Phosphorothioate Oligonucleotides E. coli cells were heat shock transformed by the method set forth in Example 3 above with the 80 µM of each of the antisense phosphorothioate oligonucleotides set forth in FIG. 17.

Luria-Bertani broth was then added to the treated E. coli cells and they were allowed to grow at 30° C. on a shaker at 250 rpm for 3 hours.

Approximately the same quantity of treated and untreated bacteria, based on optical density, were washed in phosphate buffered saline, suspended in 2×Laemmli sample buffer (Laemmli U. K.[36]), heated for 5 minutes at 95° C. and subjected to SDS-PAGE (sodium dodecyl sulfate-polyacrylamide gel electrophoresis).

The gel was blotted onto polyvinylidene difluoride protein sequencing membrane by the methods set forth in Example 1. A rabbit polyclonal SecA antiserum (der Blaauwen et al.[6]) was used to detect the expression of the E. coli secA gene. The presence of bound rabbit antibody was detected using a goat anti-rabbit immunoglobulin (Amersham Life Sciences, Oakville, Canada).

FIG. 17 is a photograph of the Western Blot of E. coli cells treated with oligonucleotides ES799 [SEQ ID NO:195] (lane 1); ES1845 [SEQ ID NO:235] (lane 2); and the control (lane 3). When compared to the control, lane 3, the ES799 [SEQ ID NO:195] and ES1845 [SEQ ID NO:235] oligonucleotides clearly decreased the SecA protein levels in the treated E. coli cells. The top band in the FIG. 17 represents SecA. Non-specific background bands appear below the SecA protein band.

It has been found that the antisense oligonucleotides are effective inhibitors of SecA expression in E. coli.

Example 5

Killing of Escherichia coli K12 by Antisense secA Oligonucleotides

Figure 18A:
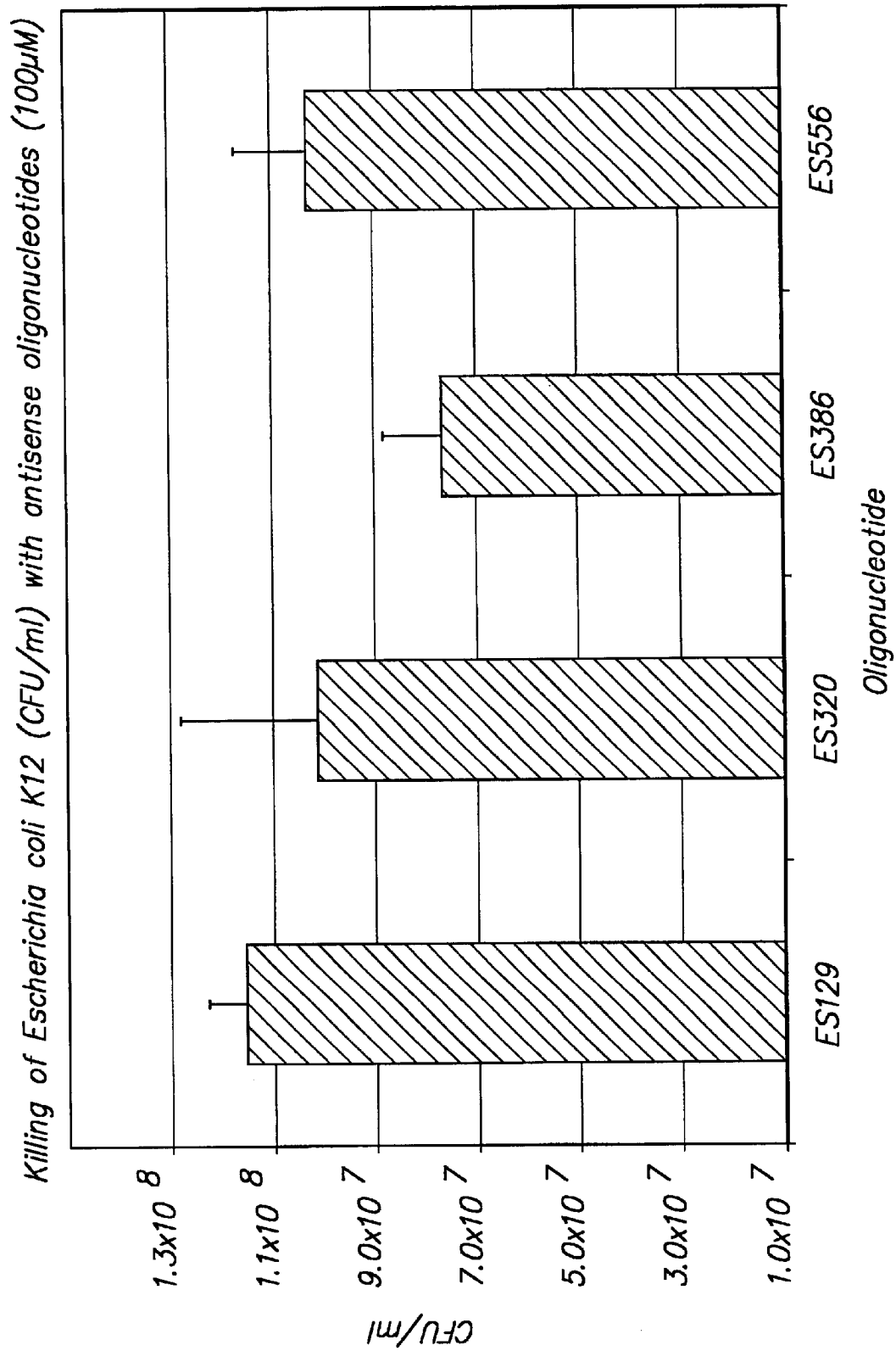
FIGS. 18a and 18b are graphs of the number of colony forming units/ml of *E. coli* cells after treatment with secA antisense oligonucleotides.
Figure 18B:
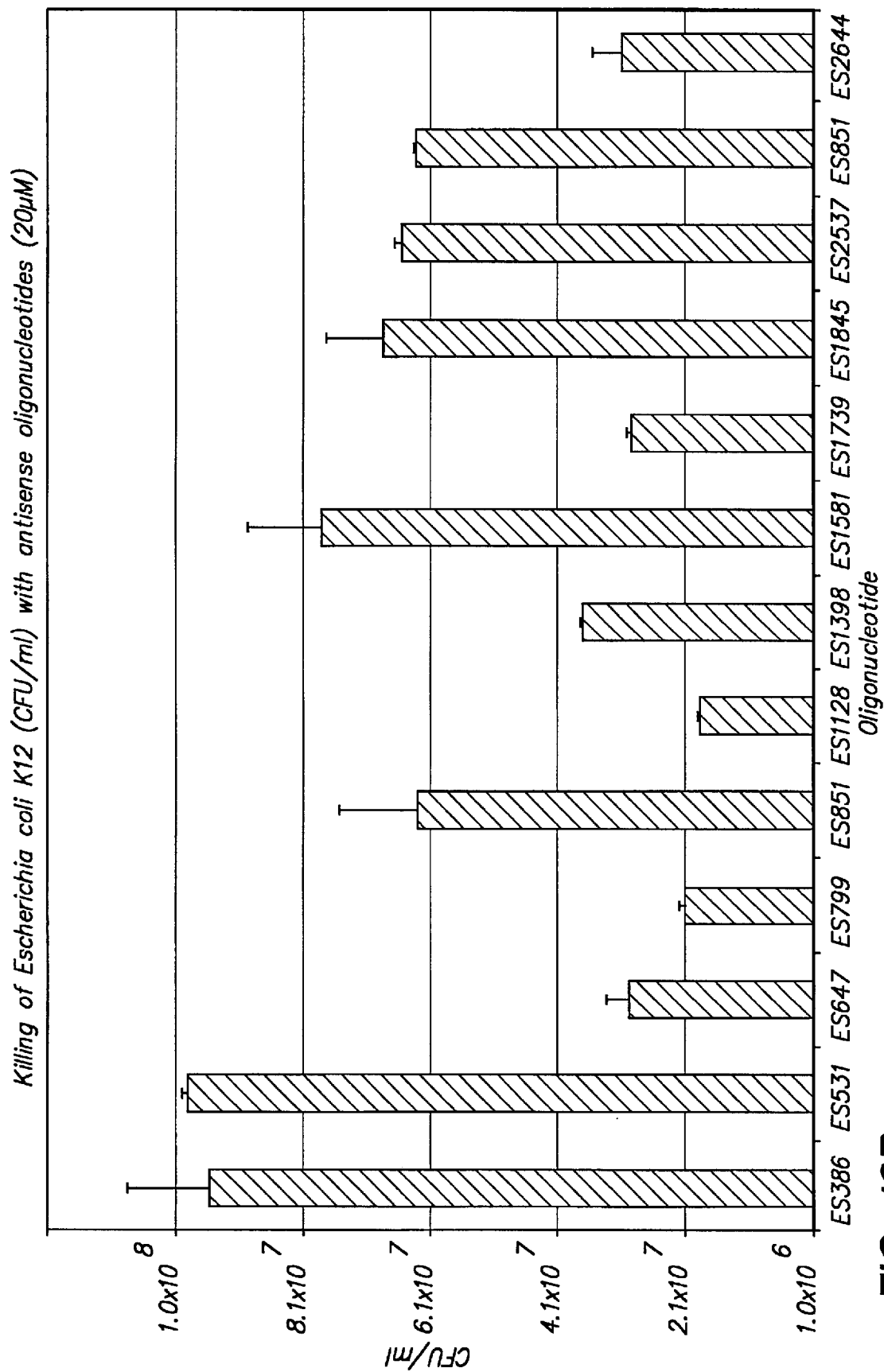
Figure 19A:
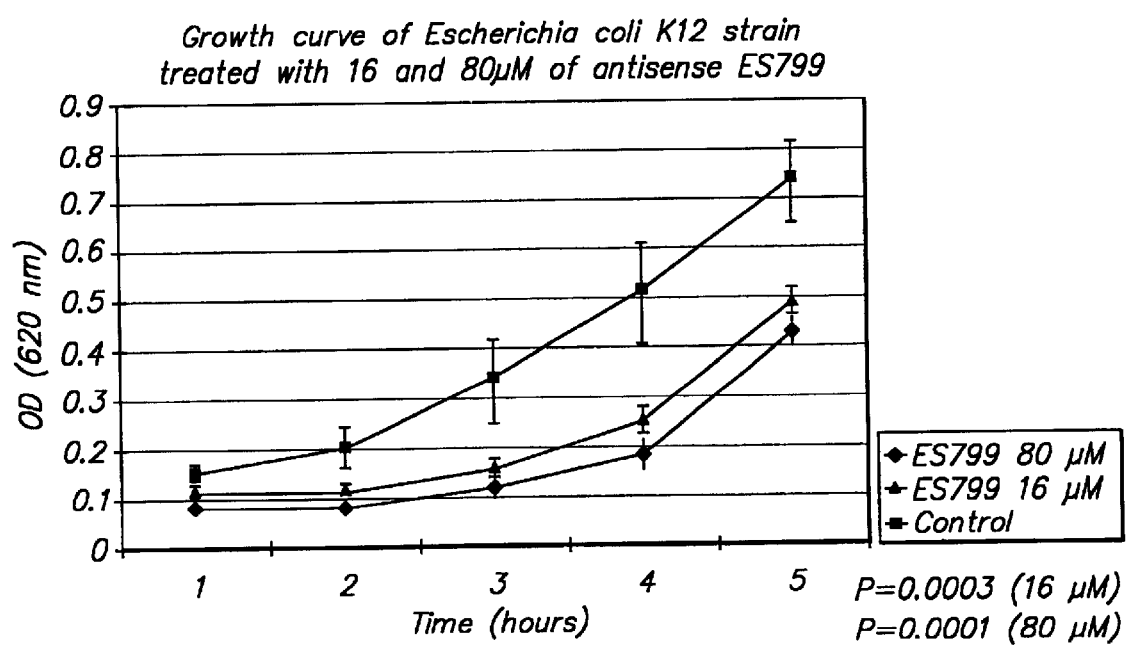
FIGS. 19a–g are graphs of growth curves of *E. coli* K12 after treatment with antisense oligonucleotides.
Figure 19B:
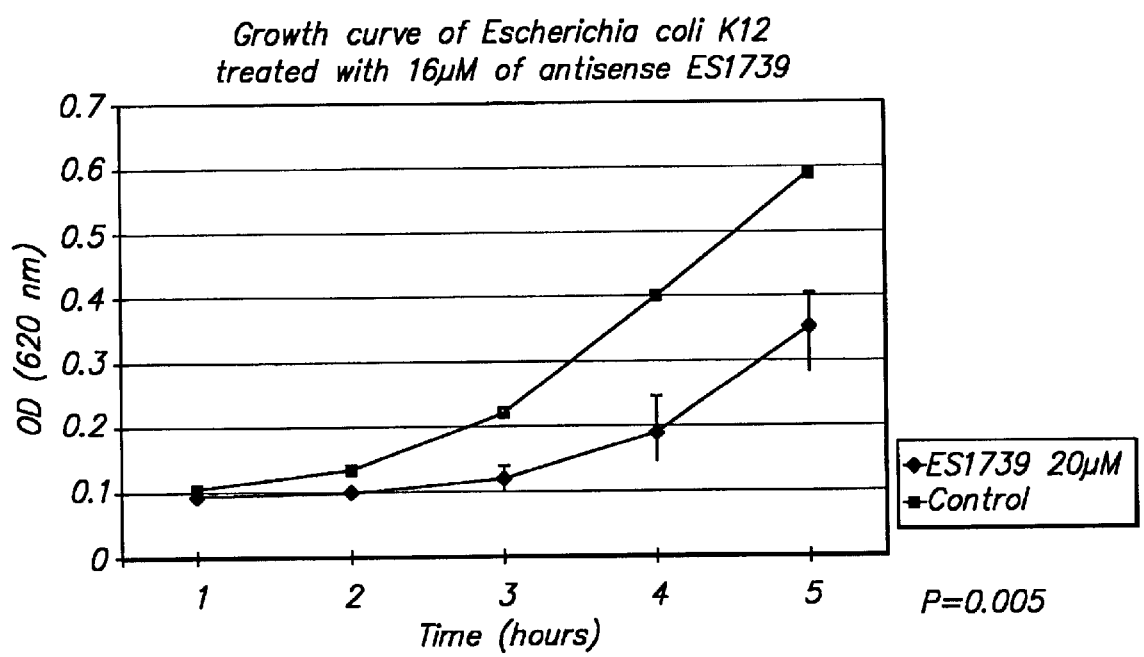
Figure 19C:
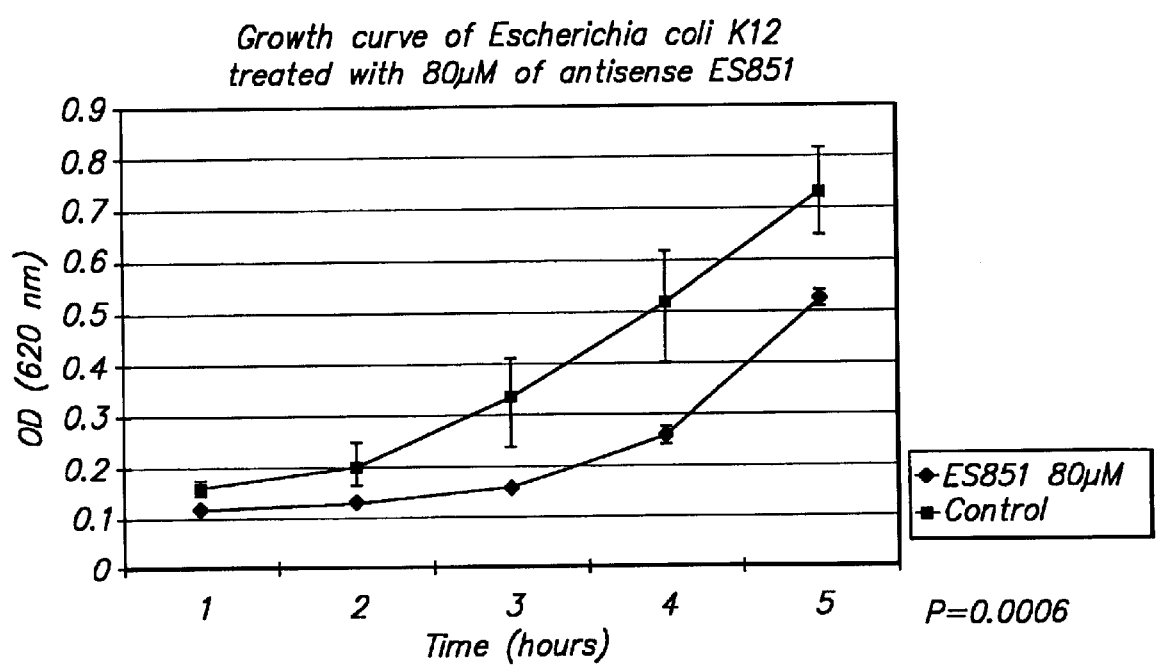
Figure 19D:
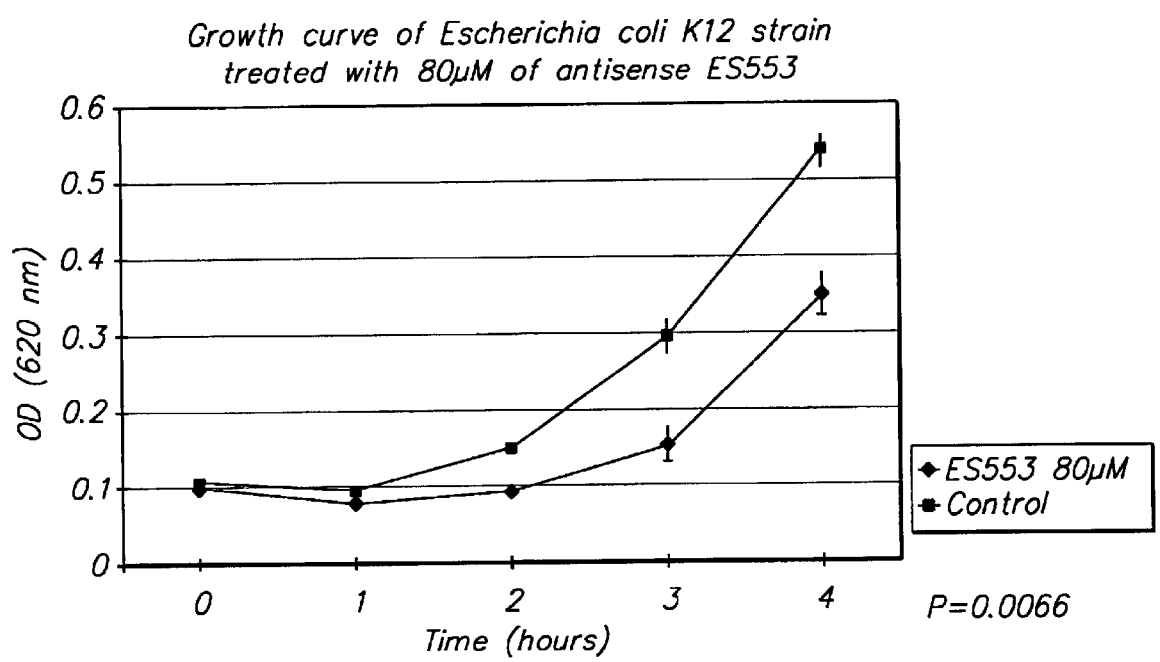
Figure 19E:
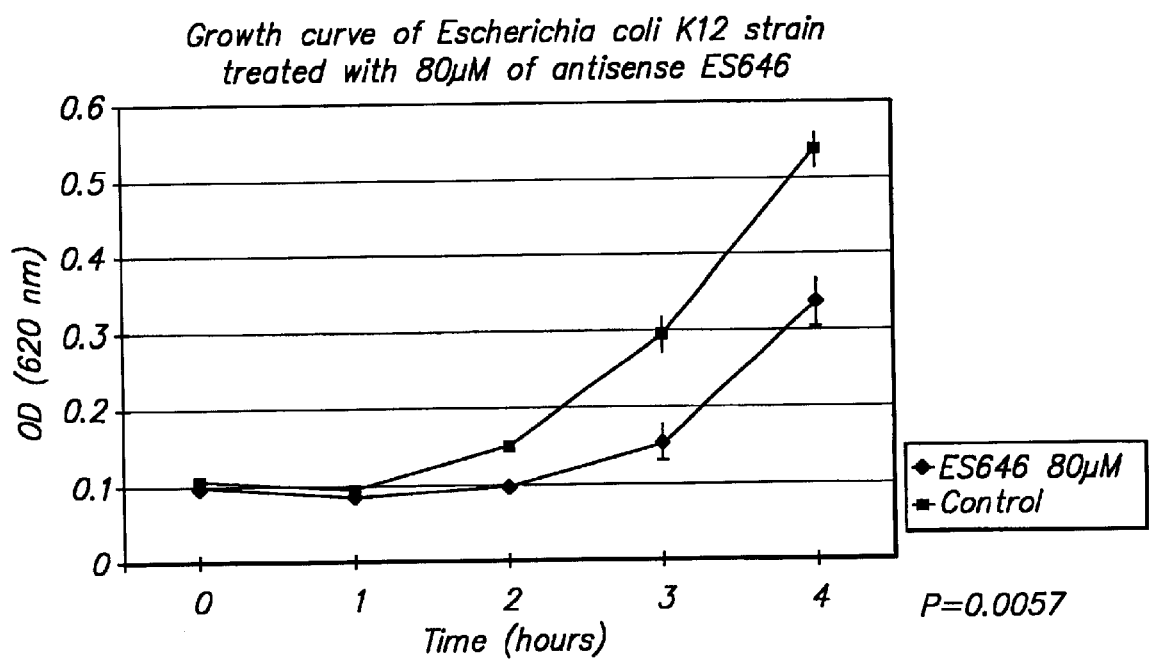
Figure 19F:
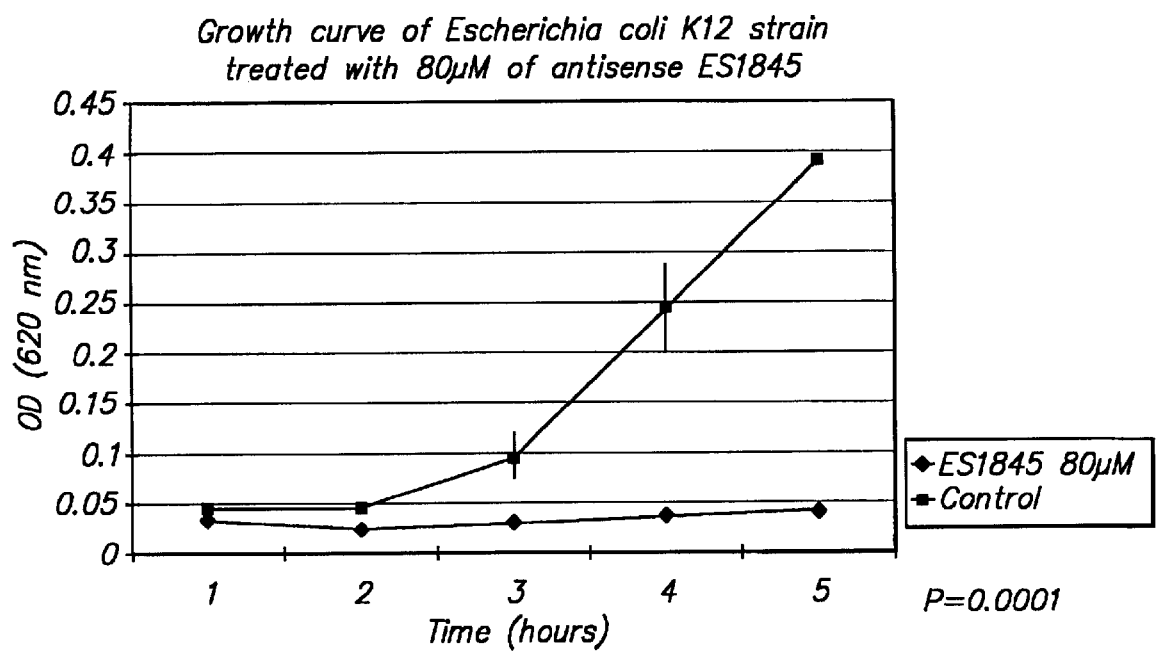
Figure 19G:
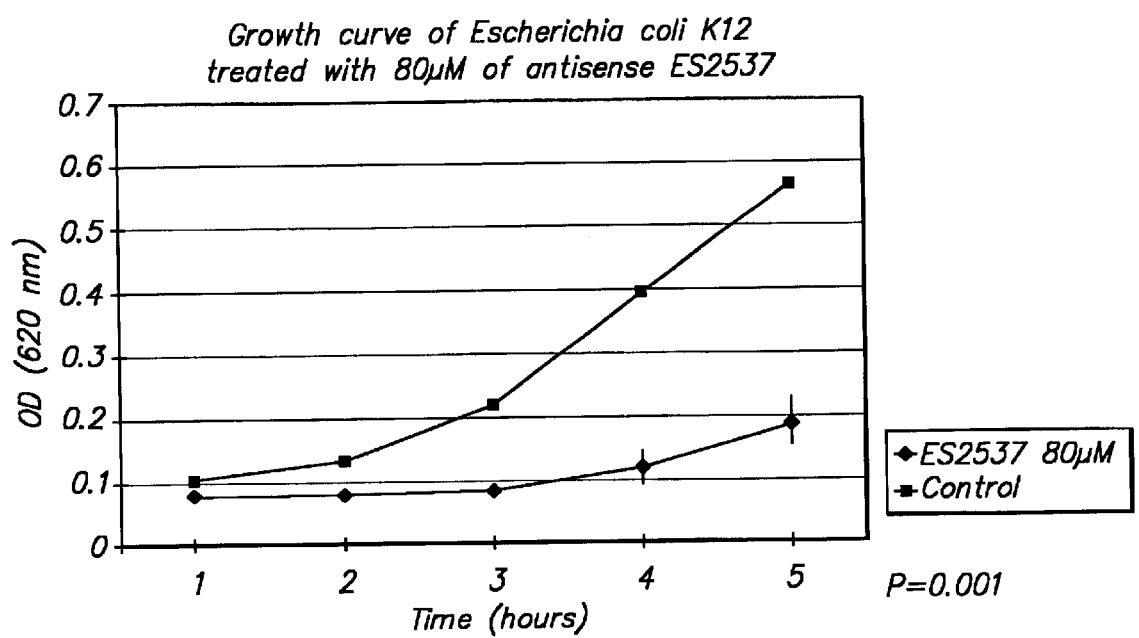

E. coli cells were heat shock transformed by the method described in Example 3 above with either 100 µM or 20 µM of the antisense phosphorothioate oligonucleotides set forth in FIGS. 18a and 18b Luria-Bertani (LB) broth (Miller J. H.[32]) was added and the bacterial samples were incubated at room temperature for 30 minutes. Dilutions of treated and untreated bacteria were incubated overnight at 37° C. on culture plates containing LB medium, and the number of colonies was counted.

The number of killed bacteria was calculated by subtracting the surviving colony forming units (CFU/ml) of the oligonucleotide-treated bacteria from the CFU/ml of the control. FIGS. 18a and 18b show the number of bacteria killed by treatment with the various antisense sequences. Accordingly, antisense oligonucleotides complementary to the secA gene act to inhibit the growth of E. coli.

Example 6

Effect of Antisense Oligonucleotides on Escherichia coli K12 Growth

E. coli cells were heat shock transformed by the method described in Example 3 with either 16 $\mu$M, 20 $\mu$M or 80 $\mu$M of each of the antisense phosphorothioate oligonucleotides set forth in FIGS. 19a–g.

Equal numbers of the treated E. coli cells were then transferred to flasks containing fresh Luria-Bertani broth to grow at 30° C. on a shaker at 250 rpm. The number of bacteria per flask was determined by the turbidity of the cultures at $OD_{620}$ taken each hour (Carpentier P.L.[40]).

FIGS. 19a–g show the rate of growth of the E. coli in each of the flasks after treatment with the various oligonucleotides. When growth curves of the treated and untreated cultures were statistically analyzed, the growth of the antisense treated cultures was found to be significantly inhibited when compared to the control cultures. The statistical p values are found in the FIGURES.

What is claimed is:

1. An antisense oligonucleotide which is nuclease resistant and comprises from about 7 to about 50 nucleotides, which nucleotides are complementary to a ribonucleotide reductase gene or a secA gene of a bacteria and wherein said antisense oligonucleotide has reduced internal duplex formation, reduced hair-pin formation and reduced homooligomer/sequence repeats and comprises at least 7 contiguous nucleotides from a sequence selected from any one of SEQ ID NOs: 14–265.

2. The oligonucleotide of claim 1 comprising one or more phosphorothioate internucleotide linkages.

3. An antisense oligonucleotide which binds to a ribonucleotide reductase gene or a secA gene of a bacteria and comprises from about 20 to about 50 nucleotides and a sequence selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; SEQ ID NO:152; SEQ ID NO:164; SEQ ID NO:176; SEQ ID NO:186; SEQ ID NO:188; SEQ ID NO:189; SEQ ID NO:191; SEQ ID NO:192; SEQ ID NO:195; SEQ ID NO:197; SEQ ID NO:206; SEQ ID NO:212; SEQ ID NO:220; SEQ ID NO:229; SEQ ID NO:235; SEQ ID NO:254; SEQ ID NO:261; SEQ ID NO:262; SEQ ID NO:263; SEQ ID NO:264; and SEQ ID NO:265.

4. A method of inhibiting the expression of a ribonucleotide reductase gene in a bacteria having a ribonucleotide reductase gene, comprising contacting said bacteria with an effective amount of an antisense oligonucleotide comprising at least about 7 nucleotides which are complementary to the ribonucleotide reductase gene of the bacteria and at least 7 contiguous nucleotides from a sequence selected from any one of SEQ ID NOs:14–157, under conditions such that the expression of the ribonucleotide reductase gene is inhibited and wherein said antisense oligonucleotide has reduced internal duplex formation, reduced hair-pin formation and reduced homooligomer/sequence repeats.

5. The method according to claim 4 wherein the antisense oligonucleotide comprises from about 20 to about 50 nucleotides and comprises a sequence selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; and SEQ ID NO:152.

6. A method of inhibiting the expression of the secA gene in a bacteria having a secA gene, comprising contacting said bacteria with an effective amount of an antisense oligonucleotide comprising at least about 7 nucleotides which are complementary to the secA gene of the bacteria and at least 7 contiguous nucleotides from a sequence selected from any one of SEQ ID NOs:158–265, under conditions such that the secA gene is inhibited and wherein said antisense oligonucleotide has reduced internal duplex formation, reduced hair-pin formation and reduced homooligomer/sequence repeats.

7. The method according to claim 6 wherein the antisense oligonucleotide comprises from about 20 to about 50 nucleotides and comprises a sequence selected from the group consisting of SEQ ID NO:164; SEQ ID NO:176; SEQ ID NO:186; SEQ ID NO:188; SEQ ID NO:189; SEQ ID NO:191; SEQ ID NO:192; SEQ ID NO:195; SEQ ID NO:197; SEQ ID NO:206; SEQ ID NO:212; SEQ ID NO:220; SEQ ID NO:229; SEQ ID NO:235; SEQ ID NO:254; SEQ ID NO:261; SEQ ID NO:262; SEQ ID NO:263; SEQ ID NO:264; and SEQ ID NO:265.

8. A method of inhibiting the growth of a bacteria having a ribonucleotide reductase gene or a secA gene, which method comprises identifying the bacteria and contacting said bacteria with an effective amount of an antisense oligonucleotide comprising from at least about 7 nucleotides which are complementary to either the ribonucleotide reductase gene or the secA gene of the bacteria and at least 7 contiguous nucleotides from a sequence selected from any one of SEQ ID NOs:14–265, under conditions whereby the growth of the bacteria is inhibited and wherein said antisense oligonucleotide has reduced internal duplex formation, reduced hair-pin formation and reduced homooligomer/sequence repeats.

9. The method according to claim 8 wherein the antisense oligonucleotide comprises from about 20 to about 50 nucleotides and comprises a sequence selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; SEQ ID NO:152; SEQ ID NO:164; SEQ ID NO:176; SEQ ID NO:186; SEQ ID NO:188; SEQ ID NO:189; SEQ ID NO:191; SEQ ID NO:192; SEQ ID NO:195; SEQ ID NO:197; SEQ ID NO:206; SEQ ID NO:212; SEQ ID NO:220; SEQ ID NO:229; SEQ ID NO:235; SEQ ID NO:254; SEQ ID NO:261; SEQ ID NO:262; SEQ ID NO:263; SEQ ID NO:264; and SEQ ID NO:265.

10. An antisense oligonucleotide which is nuclease resistant and comprises from about 7 to about 50 nucleotides that are complementary to a ribonucleotide reductase gene of a bacteria and at least 7 contiguous nucleotides from a sequence selected from any one of SEQ ID NOs:14–157, with the proviso that the bacteria is not *Mycobacterium tuberculosis*.

11. The antisense oligonucleotide of claim 10 comprising from about 7 to about 35 nucleotides.

12. The antisense oligonucleotide of claim 10, wherein the antisense oligonucleotide comprises from about 20 to about 50 nucleotides and comprises a sequence selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; and SEQ ID NO:152.

13. A method of inhibiting the expression of a ribonucleotide reductase gene in a bacteria having a ribonucleotide reductase gene, comprising contacting said bacteria with an effective amount of an antisense oligonucleotide comprising at least about 7 nucleotides which are complementary to the ribonucleotide reductase gene of the bacteria and at least 7 contiguous nucleotides from a sequence selected from any one of SEQ ID NOs:14–157, under conditions such that the expression of the ribonucleotide reductase gene is inhibited with the proviso that the bacteria is not *Mycobacterium tuberculosis*.

14. The method of claim 13 wherein the oligonucleotide comprises from about 7 to about 35 nucleotides.

15. The method of claim 13 wherein the oligonucleotide comprises from about 20 to about 50 nucleotides and comprises a sequence selected from the group consisting of SEQ ID NO:22; SEQ ID NO:43; SEQ ID NO:62; SEQ ID NO:74; SEQ ID NO:75; SEQ ID NO:76; SEQ ID NO:143; SEQ ID NO:145; and SEQ ID NO:152.

16. An antisense oligonucleotide which is nuclease resistant and comprises from about 7 to about 50 nucleotides that are complementary to a secA gene of a bacteria and at least 7 contiguous nucleotides from a sequence selected from any one of SEQ ID NOs:158–265, with the proviso that the bacteria is not *Staphylococcus aureus* or *Mycobacterium tuberculosis*.

17. The antisense oligonucleotide of claim 16 comprising from about 7 to about 35 nucleotides.

18. The antisense oligonucleotide of claim 16 comprising from about 20 to about 50 nucleotides and a sequence selected from the group consisting of SEQ ID NO:164; SEQ ID NO:176; SEQ ID NO:186; SEQ ID NO:188; SEQ ID NO:189; SEQ ID NO:191; SEQ ID NO:192; SEQ ID NO:195; SEQ ID NO:197; SEQ ID NO:206; SEQ ID NO:212; SEQ ID NO:220; SEQ ID NO:229; SEQ ID NO:235; SEQ ID NO:254; SEQ ID NO:261; SEQ ID NO:262; SEQ ID NO:263; SEQ ID NO:264; and SEQ ID NO:265.

19. A method of inhibiting the expression of the secA gene in a bacteria having a secA gene, comprising contacting said bacteria with an effective amount of an antisense oligonucleotide comprising at least about 7 nucleotides which are complementary to the secA gene of the bacteria and at least 7 contiguous nucleotides from a sequence selected from any one of SEQ ID NOs:158–265, under conditions such that the secA gene is inhibited, with the proviso that the bacteria is not *Staphylococcus aureus* or *Mycobacterium tuberculosis*.

20. A method of inhibiting the growth of a bacteria having a ribonucleotide reductase gene, which method comprises identifying the bacteria and contacting said bacteria with an effective amount of an antisense oligonucleotide comprising at least about 7 nucleotides which are complementary to the ribonucleotide reductase gene of the bacteria and at least 7 contiguous nucleotides from a sequence selected from any one of SEQ ID NOs:14–157, under conditions whereby the growth of the bacteria is inhibited, with the proviso that the bacteria is not *Mycobacterium tuberculosis*.

21. A method of inhibiting the growth of a bacteria having a secA gene, which method comprises identifying the bacteria and contacting said bacteria with an effective amount of an antisense oligonucleotide comprising at least about 7 nucleotides which are complementary to the secA gene of the bacteria and at least 7 contiguous nucleotides from a sequence selected from any one of SEQ ID NOs:158–265, under conditions whereby the growth of the bacteria is inhibited, with the proviso that the bacteria is not *Staphylococcus aureus* or *Mycobacterium tuberculosis*.

* * * * *